United States Patent
Cornen et al.

(10) Patent No.: US 11,083,785 B2
(45) Date of Patent: Aug. 10, 2021

(54) SIGLEC-10 ANTIBODIES

(71) Applicant: INNATE PHARMA, Marseilles (FR)

(72) Inventors: Stephanie Cornen, Marseilles (FR);
Laurent Gauthier, Marseilles (FR);
Benjamin Rossi, Marseilles (FR);
Nicolai Wagtmann, Concord, MA (US)

(73) Assignee: INNATE PHARMA, Marseilles (FR)

(*) Notice: Subject to any disclaimer, the term of this patent is extended or adjusted under 35 U.S.C. 154(b) by 26 days.

(21) Appl. No.: 15/776,452

(22) PCT Filed: Nov. 17, 2016

(86) PCT No.: PCT/EP2016/077955
§ 371 (c)(1),
(2) Date: May 16, 2018

(87) PCT Pub. No.: WO2017/085166
PCT Pub. Date: May 26, 2017

(65) Prior Publication Data
US 2018/0344829 A1    Dec. 6, 2018

Related U.S. Application Data

(60) Provisional application No. 62/256,188, filed on Nov. 17, 2015.

(51) Int. Cl.
*C07K 14/705* (2006.01)
*A61K 39/00* (2006.01)
*C07K 16/28* (2006.01)
*A61P 35/00* (2006.01)

(52) U.S. Cl.
CPC ....... *A61K 39/001113* (2018.08); *A61P 35/00* (2018.01); *C07K 14/705* (2013.01); *C07K 16/2803* (2013.01); *A61K 2039/572* (2013.01); *A61K 2039/58* (2013.01); *C07K 2317/33* (2013.01); *C07K 2317/76* (2013.01); *C07K 2319/30* (2013.01)

(58) Field of Classification Search
CPC .......... C07K 2317/565; C07K 2317/76; C07K 14/705; A61K 39/001113
USPC ..................................................... 424/133.1
See application file for complete search history.

(56) References Cited

U.S. PATENT DOCUMENTS

2017/0306014 A1    10/2017    Cornen et al.

FOREIGN PATENT DOCUMENTS

WO    WO 02/08257    1/2002

OTHER PUBLICATIONS

George et al. ((1998) Circulation 97: 900-906).*
Apantaku et al. (Breast cancer diagnosis and screening, (2000) American Family Physician ).*
Martin et al (Journal of the National Cancer Institute, (Jul. 19, 2000) vol. 92, No. 14: pp. 1126-1135).*
Voskoglou-Nomikos (Clin. Can. Res. (2003) 9:4227-4239 ).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Huang et al. (Appl Microbiol Biotechnol 87:401-410 (2010)).*
Kivi, E. et al. "Human Siglec-10 can bind to vascular adhesion protein-1 and serves as its substrate" *Blood*, Dec. 17, 2009, pp. 5385-5392, vol. 114, No. 26.
Munday, J. et al. "Identification, characterization and leucocyte expression of Siglec-10, a novel human sialic acid-binding receptor" *Biochemical Journal*, Jan. 1, 2001, pp. 489-497, vol. 355, No. 2.
R&D Systems Catalogue, "Human Siglec-10 Antibody" Accession No. Q96LC7, Catalog No. MAB2130, retrieved on Oct. 13, 2015, p. 1.
Written Opinion in International Application No. PCT/EP2016/077955, dated Feb. 6, 2017, pp. 1-6.
Claims pending in U.S. Appl. No. 16/629,588, dated Jan. 9, 2020, pp. 1-4.
Barkal, A. A. et al. "CD24 signalling through macrophage Siglec-10 is a target for cancer immunotherapy" *Nature*, Jul. 31, 2019, pp. 1-22, vol. 572, https://doi.org/10.1038/s41586-019-1456-0.
Lee, J.-H. et al. "CD24 overexpression in cancer development and progression: A meta-analysis" *Oncology Reports*, 2009, pp. 1149-1156, vol. 22.

* cited by examiner

*Primary Examiner* — Lynn A Bristol
(74) *Attorney, Agent, or Firm* — Saliwanchik, Lloyd & Eisenschenk

(57) ABSTRACT

This disclosure relates to agents that bind and neutralize the inhibitory activity of Siglec-10 in lymphocytes, notably by inhibiting the binding of Siglec-10 to its sialic acid ligands on target cells, notably tumor cells. Such agents can be used for the treatment of cancers.

9 Claims, 6 Drawing Sheets

Figure 1:
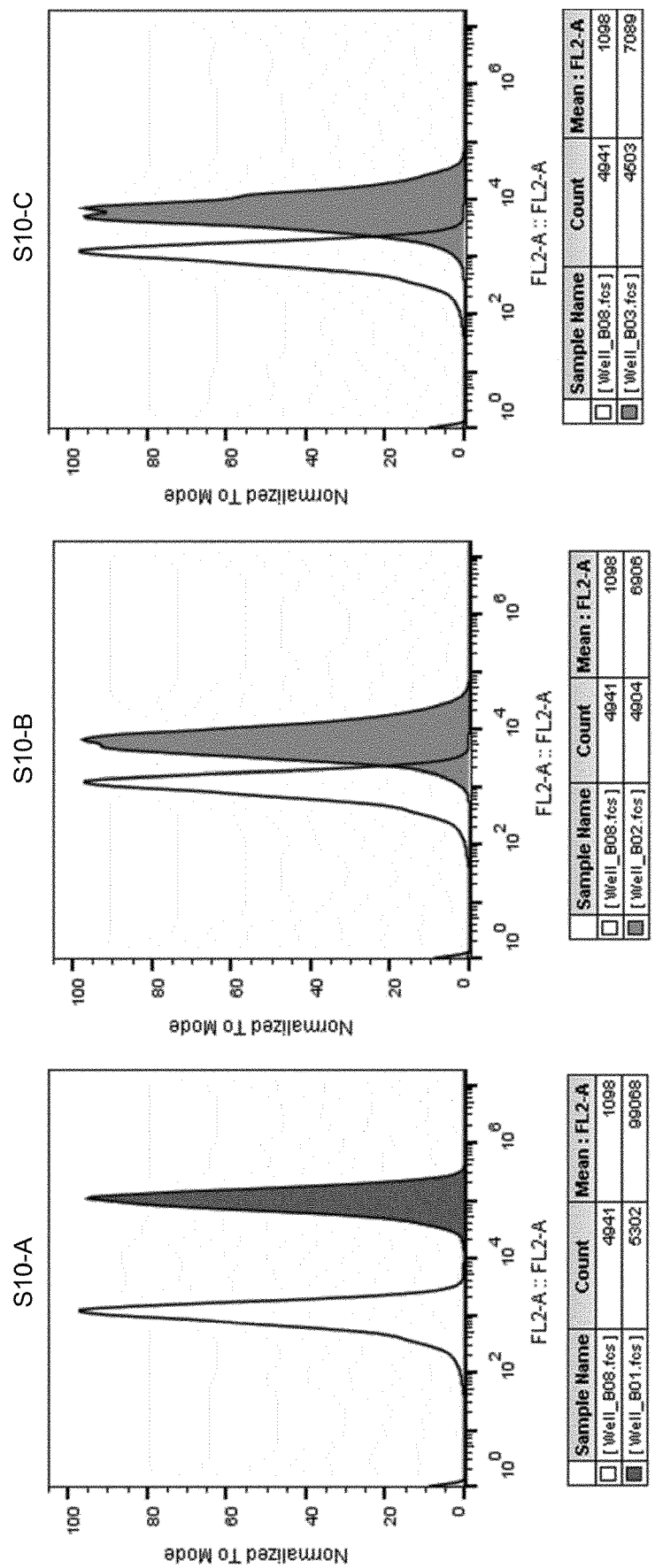
Figure 1:
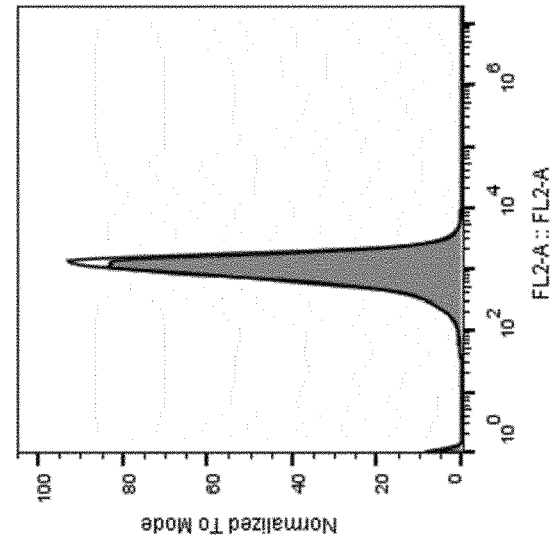
Figure 1:
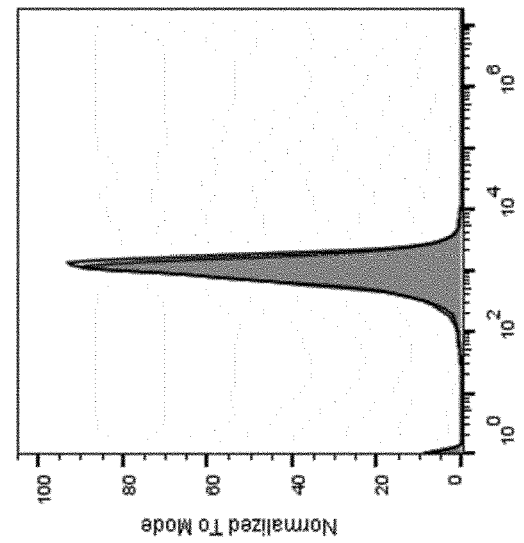
Figure 1:
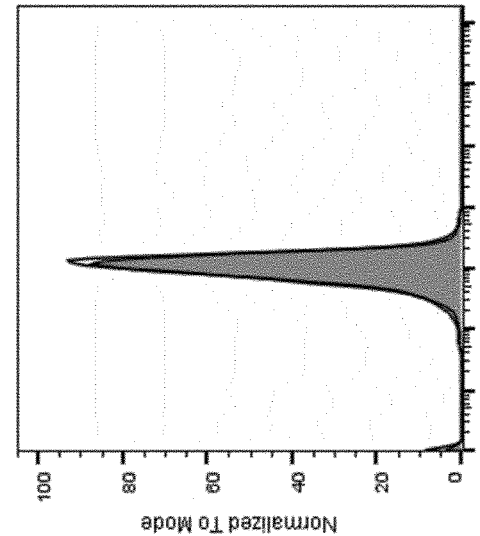

Specification includes a Sequence Listing.

Siglec-7 expressing cells

SEQUENCE LISTING

<160> NUMBER OF SEQ ID NOS: 35

<210> SEQ ID NO 1
<211> LENGTH: 681
<212> TYPE: PRT
<213> ORGANISM: homo sapiens

<400> SEQUENCE: 1

```
Met Asp Gly Arg Phe Trp Ile Arg Val Gln Glu Ser Val Met Val Pro
1               5                   10                  15

Glu Gly Leu Cys Ile Ser Val Pro Cys Ser Phe Ser Tyr Pro Arg Gln
            20                  25                  30

Asp Trp Thr Gly Ser Thr Pro Ala Tyr Gly Tyr Trp Phe Lys Ala Val
        35                  40                  45

Thr Glu Thr Thr Lys Gly Ala Pro Val Ala Thr Asn His Gln Ser Arg
    50                  55                  60

Glu Val Glu Met Ser Thr Arg Gly Arg Phe Gln Leu Thr Gly Asp Pro
65                  70                  75                  80

Ala Lys Gly Asn Cys Ser Leu Val Ile Arg Asp Ala Gln Met Gln Asp
                85                  90                  95

Glu Ser Gln Tyr Phe Phe Arg Val Glu Arg Gly Ser Tyr Val Arg Tyr
            100                 105                 110

Asn Phe Met Asn Asp Gly Phe Phe Leu Lys Val Thr Ala Leu Thr Gln
        115                 120                 125

Lys Pro Asp Val Tyr Ile Pro Glu Thr Leu Glu Pro Gly Gln Pro Val
    130                 135                 140

Thr Val Ile Cys Val Phe Asn Trp Ala Phe Glu Glu Cys Pro Pro Pro
145                 150                 155                 160

Ser Phe Ser Trp Thr Gly Ala Ala Leu Ser Ser Gln Gly Thr Lys Pro
                165                 170                 175

Thr Thr Ser His Phe Ser Val Leu Ser Phe Thr Pro Arg Pro Gln Asp
            180                 185                 190

His Asn Thr Asp Leu Thr Cys His Val Asp Phe Ser Arg Lys Gly Val
        195                 200                 205

Ser Val Gln Arg Thr Val Arg Leu Arg Val Ala Tyr Ala Pro Arg Asp
    210                 215                 220

Leu Val Ile Ser Ile Ser Arg Asp Asn Thr Pro Ala Leu Glu Pro Gln
225                 230                 235                 240

Pro Gln Gly Asn Val Pro Tyr Leu Glu Ala Gln Lys Gly Gln Phe Leu
                245                 250                 255

Arg Leu Leu Cys Ala Ala Asp Ser Gln Pro Pro Ala Thr Leu Ser Trp
            260                 265                 270

Val Leu Gln Asn Arg Val Leu Ser Ser Ser His Pro Trp Gly Pro Arg
        275                 280                 285

Pro Leu Gly Leu Glu Leu Pro Gly Val Lys Ala Gly Asp Ser Gly Arg
    290                 295                 300

Tyr Thr Cys Arg Ala Glu Asn Arg Leu Gly Ser Gln Arg Ala Leu
305                 310                 315                 320

Asp Leu Ser Val Gln Tyr Pro Pro Glu Asn Leu Arg Val Met Val Ser
                325                 330                 335

Gln Ala Asn Arg Thr Val Leu Glu Asn Leu Gly Asn Gly Thr Ser Leu
            340                 345                 350

Pro Val Leu Glu Gly Gln Ser Leu Cys Leu Val Cys Val Thr His Ser
        355                 360                 365
```

Ser Pro Pro Ala Arg Leu Ser Trp Thr Gln Arg Gly Gln Val Leu Ser
370                 375                 380

Pro Ser Gln Pro Ser Asp Pro Gly Val Leu Glu Leu Pro Arg Val Gln
385                 390                 395                 400

Val Glu His Glu Gly Glu Phe Thr Cys His Ala Arg His Pro Leu Gly
                405                 410                 415

Ser Gln His Val Ser Leu Ser Leu Ser Val His Tyr Ser Pro Lys Leu
            420                 425                 430

Leu Gly Pro Ser Cys Ser Trp Glu Ala Glu Gly Leu His Cys Ser Cys
        435                 440                 445

Ser Ser Gln Ala Ser Pro Ala Pro Ser Leu Arg Trp Trp Leu Gly Glu
450                 455                 460

Glu Leu Leu Glu Gly Asn Ser Ser Gln Asp Ser Phe Glu Val Thr Pro
465                 470                 475                 480

Ser Ser Ala Gly Pro Trp Ala Asn Ser Ser Leu Ser Leu His Gly Gly
                485                 490                 495

Leu Ser Ser Gly Leu Arg Leu Arg Cys Glu Ala Trp Asn Val His Gly
            500                 505                 510

Ala Gln Ser Gly Ser Ile Leu Gln Leu Pro Asp Lys Lys Gly Leu Ile
        515                 520                 525

Ser Thr Ala Phe Ser Asn Gly Ala Phe Leu Gly Ile Gly Ile Thr Ala
530                 535                 540

Leu Leu Phe Leu Cys Leu Ala Leu Ile Ile Met Lys Ile Leu Pro Lys
545                 550                 555                 560

Arg Arg Thr Gln Thr Glu Thr Pro Arg Pro Arg Phe Ser Arg His Ser
                565                 570                 575

Thr Ile Leu Asp Tyr Ile Asn Val Val Pro Thr Ala Gly Pro Leu Ala
            580                 585                 590

Gln Lys Arg Asn Gln Lys Ala Thr Pro Asn Ser Pro Arg Thr Pro Leu
        595                 600                 605

Pro Pro Gly Ala Pro Ser Pro Glu Ser Lys Lys Asn Gln Lys Lys Gln
610                 615                 620

Tyr Gln Leu Pro Ser Phe Pro Glu Pro Lys Ser Ser Thr Gln Ala Pro
625                 630                 635                 640

Glu Ser Gln Glu Ser Gln Glu Glu Leu His Tyr Ala Thr Leu Asn Phe
                645                 650                 655

Pro Gly Val Arg Pro Arg Pro Glu Ala Arg Met Pro Lys Gly Thr Gln
            660                 665                 670

Ala Asp Tyr Ala Glu Val Lys Phe Gln
        675                 680

```
<210> SEQ ID NO 2
<211> LENGTH: 3400
<212> TYPE: DNA
<213> ORGANISM: homo sapiens

<400> SEQUENCE: 2
gcccccagga gacccagagg acaactgggc aaggtgggcc ggagagtgtg ggggaaggca      60
aaggagttct gtgagctcag cgtctgaagc tcatttcatg catcaggccc cagggctcag     120
cttccgcctt cggcttcccc ttctgccaag agccctgagc cactcacagc acgaccagag     180
aacaggcctg tctcaggcag gccctgcgcc tcctatgcgg agatgctact gccactgctg     240
ctgtcctcgc tgctgggcgg gtcccaggct atggatggga gattctggat acgagtgcag     300
gagtcagtga tggtgccgga gggcctgtgc atctctgtgc cctgctcttt ctcctacccc     360
```

```
cgacaagact ggacagggtc taccccagct tatggctact ggttcaaagc agtgactgag      420
acaaccaagg gtgctcctgt ggccacaaac caccagagtc gagaggtgga aatgagcacc      480
cggggccgat tccagctcac tgggatccc gccaaggga actgctcctt ggtgatcaga        540
gacgcgcaga tgcaggatga gtcacagtac ttctttcggg tggagagagg aagctatgtg     600
agatataatt tcatgaacga tgggttcttt ctaaaagtaa cagccctgac tcagaagcct     660
gatgtctaca tccccgagac cctggagccc gggcagccgg tgacggtcat ctgtgtgttt     720
aactgggcct ttgaggaatg tccacccct tctttctcct ggacggggc tgccctctcc       780 tcccaaggaa ccaaaccaac gacctcccac ttctcagtgc tcagcttcac gcccagaccc     840
caggaccaca acaccgacct cacctgccat gtggacttct ccagaaaggg tgtgagcgca     900
cagaggaccg tccgactccg tgtggcctat gcccccagag accttgttat cagcatttca     960
cgtgacaaca cgccagccct ggagcccag ccccaggaa atgtcccata cctggaagcc      1020
caaaaaggcc agttcctgcg gctcctctgt gctgctgaca gccagcccccc tgccacactg   1080 agctgggtcc tgcagaacag agtcctctcc tcgtcccatc cctggggccc tagacccctg    1140
gggctggagc tgcccggggt gaaggctggg gattcagggc gctacacctg ccgagcggag    1200
aacaggcttg gctcccagca gcgagccctg gacctctctg tgcagtatcc tccagagaac   1260
ctgagagtga tggttttccca agcaaacagg acagtcctgg aaaaccttgg gaacggcacg   1320
tctctcccag tactggaggg ccaaagcctg tgcctggtct gtgtcacaca cagcagcccc    1380
ccagccaggc tgagctggac ccagagggga caggttctga gcccctccca gccctcagac    1440
cccggggtcc tggagctgcc tcgggttcaa gtggagcacg aaggagagtt cacctgccac    1500
gctcggcacc cactgggctc ccagcacgtc tctctcagcc tctccgtgca ctactccccg    1560
aagctgctgg gcccctcctg ctcctgggag gctgagggtc tgcactgcag ctgctcctcc    1620
caggccagcc cggccccctc tctgcgctgg tggcttgggg aggagctgct ggaggggaac   1680
agcagccagg actccttcga ggtcaccccc agctcagccg ggccctgggc aacagctcc    1740 ctgagcctcc atggagggct cagctccggc ctcaggctcc gctgtgaggc ctggaacgtc    1800
catggggccc agagtggatc catcctgcag ctgccagata agaagggact catctcaacg   1860
gcattctcca acggagcgtt tctgggaatc ggcatcacgg ctcttctttt cctctgcctg    1920
gccctgatca tcatgaagat tctaccgaag agacggactc agacagaaac cccgaggccc    1980
aggttctccc ggcacagcac gatcctggat tacatcaatg tggtcccgac ggctggcccc    2040
ctggctcaga gcggaatca gaaagccaca ccaaacagtc ctcggacccc tcttccacca    2100
ggtgctccct ccccagaatc aaagaagaac cagaaaaagc agtatcagtt gcccagtttc   2160
ccagaaccca atcatccac tcaagcccca gaatccagg agagccaaga ggagctccat    2220
tatgccacgc tcaacttccc aggcgtcaga cccaggcctg aggcccggat gcccaagggc    2280
acccaggcgg attatgcaga agtcaagttc caatgagggt ctcttaggct ttaggactgg   2340
gacttcggct agggaggaag gtagagtaag aggttgaaga taacagagtg caaagtttcc   2400
ttctctccct ctctctctct ctttctctct ctctctctct ttctctctct tttaaaaaaa    2460
catctggcca gggcacagtg gctcacgcct gtaatcccag cactttggga ggttgaggtg    2520
ggcagatcgc ctgaggtcgg gagttcgaga ccagcctggc caacttggtg aaaccccgtc    2580
tctactaaaa atacaaaaat tagctgggca tggtggcagg cgcctgtaat cctacctact    2640
tgggaagctg aggcaggaga atcacttgaa cctgggagac ggaggttgca gtgagccaag    2700
```

| | | |
|---|---|---|
| atcacaccat tgcacgccag cctgggcaac aaagcgagac tccatctcaa aaaaaaaatc | | 2760 |
| ctccaaatgg gttgggtgtc tgtaatccca gcactttggg aggctaaggt gggtggattg | | 2820 |
| cttgagccca ggagttcgag accagcctgg gcaacatggt gaaaccccat ctctacaaaa | | 2880 |
| aatacaaaac atagctgggc ttggtggtgt gtgcctgtag tcccagctgt cagacattta | | 2940 |
| aaccagagca actccatctg aataggagc tgaataaaat gaggctgaga cctactgggc | | 3000 |
| tgcattctca gacagtggag gcattctaag tcacaggatg agacaggagg tccgtacaag | | 3060 |
| atacaggtca taaagacttt gctgataaaa cagattgcag taaagaagcc aaccaaatcc | | 3120 |
| caccaaaacc aagttggcca cgagagtgac ctctggtcgt cctcactgct acactcctga | | 3180 |
| cagcaccatg acagtttaca atgccatgg caacatcagg aagttacccg atatgtccca | | 3240 |
| aaagggggag gaatgaataa tccaccccctt gtttagcaaa taagcaagaa ataaccataa | | 3300 |
| aagtgggcaa ccagcagctc taggcgctgc tcttgtctat ggagtagcca ttcttttgtt | | 3360 |
| cctttacttt cttaataaac ttgctttcac cttaaaaaaa | | 3400 |

<210> SEQ ID NO 3
<211> LENGTH: 449
<212> TYPE: PRT
<213> ORGANISM: Homo sapiens

<400> SEQUENCE: 3

```
Gln Lys Ser Asn Arg Lys Asp Tyr Ser Leu Thr Met Gln Ser Ser Val
1               5                   10                  15

Thr Val Gln Glu Gly Met Cys Val His Val Arg Cys Ser Phe Ser Tyr
            20                  25                  30

Pro Val Asp Ser Gln Thr Asp Ser Asp Pro Val His Gly Tyr Trp Phe
        35                  40                  45

Arg Ala Gly Asn Asp Ile Ser Trp Lys Ala Pro Val Ala Thr Asn Asn
    50                  55                  60

Pro Ala Trp Ala Val Gln Glu Glu Thr Arg Asp Arg Phe His Leu Leu
65                  70                  75                  80

Gly Asp Pro Gln Thr Lys Asn Cys Thr Leu Ser Ile Arg Asp Ala Arg
                85                  90                  95

Met Ser Asp Ala Gly Arg Tyr Phe Phe Arg Met Glu Lys Gly Asn Ile
            100                 105                 110

Lys Trp Asn Tyr Lys Tyr Asp Gln Leu Ser Val Asn Val Thr Ala Leu
        115                 120                 125

Thr His Arg Pro Asn Ile Leu Ile Pro Gly Thr Leu Glu Ser Gly Cys
    130                 135                 140

Phe Gln Asn Leu Thr Cys Ser Val Pro Trp Ala Cys Glu Gln Gly Thr
145                 150                 155                 160

Pro Pro Met Ile Ser Trp Met Gly Thr Ser Val Ser Pro Leu His Pro
                165                 170                 175

Ser Thr Thr Arg Ser Ser Val Leu Thr Leu Ile Pro Gln Pro Gln His
            180                 185                 190

His Gly Thr Ser Leu Thr Cys Gln Val Thr Leu Pro Gly Ala Gly Val
        195                 200                 205

Thr Thr Asn Arg Thr Ile Gln Leu Asn Val Ser Tyr Pro Pro Gln Asn
    210                 215                 220

Leu Thr Val Thr Val Phe Gln Gly Glu Gly Thr Ala Ser Thr Ala Leu
225                 230                 235                 240

Gly Asn Ser Ser Ser Leu Ser Val Leu Glu Gly Gln Ser Leu Arg Leu
                245                 250                 255
```

-continued

```
Val Cys Ala Val Asp Ser Asn Pro Pro Ala Arg Leu Ser Trp Thr Trp
            260                 265                 270

Arg Ser Leu Thr Leu Tyr Pro Ser Gln Pro Ser Asn Pro Leu Val Leu
        275                 280                 285

Glu Leu Gln Val His Leu Gly Asp Glu Gly Phe Thr Cys Arg Ala
290                 295                 300

Gln Asn Ser Leu Gly Ser Gln His Val Ser Leu Asn Leu Ser Leu Gln
305                 310                 315                 320

Gln Glu Tyr Thr Gly Lys Met Arg Pro Val Ser Gly Val Leu Leu Gly
                325                 330                 335

Ala Val Gly Gly Ala Gly Ala Thr Ala Leu Val Phe Leu Ser Phe Cys
                340                 345                 350

Val Ile Phe Ile Val Val Arg Ser Cys Arg Lys Lys Ser Ala Arg Pro
            355                 360                 365

Ala Ala Asp Val Gly Asp Ile Gly Met Lys Asp Ala Asn Thr Ile Arg
370                 375                 380

Gly Ser Ala Ser Gln Gly Asn Leu Thr Glu Ser Trp Ala Asp Asp Asn
385                 390                 395                 400

Pro Arg His His Gly Leu Ala Ala His Ser Ser Gly Glu Glu Arg Glu
                405                 410                 415

Ile Gln Tyr Ala Pro Leu Ser Phe His Lys Gly Glu Pro Gln Asp Leu
                420                 425                 430

Ser Gly Gln Glu Ala Thr Asn Asn Glu Tyr Ser Glu Ile Lys Ile Pro
                435                 440                 445

Lys

<210> SEQ ID NO 4
<211> LENGTH: 446
<212> TYPE: PRT
<213> ORGANISM: homo sapiens

<400> SEQUENCE: 4

Gln Thr Ser Lys Leu Leu Thr Met Gln Ser Ser Val Thr Val Gln Glu
1               5                   10                  15

Gly Leu Cys Val His Val Pro Cys Ser Phe Ser Tyr Pro Ser His Gly
                20                  25                  30

Trp Ile Tyr Pro Gly Pro Val Val His Gly Tyr Trp Phe Arg Glu Gly
            35                  40                  45

Ala Asn Thr Asp Gln Asp Ala Pro Val Ala Thr Asn Asn Pro Ala Arg
        50                  55                  60

Ala Val Trp Glu Glu Thr Arg Asp Arg Phe His Leu Leu Gly Asp Pro
65                  70                  75                  80

His Thr Lys Asn Cys Thr Leu Ser Ile Arg Asp Ala Arg Arg Ser Asp
                85                  90                  95

Ala Gly Arg Tyr Phe Phe Arg Met Glu Lys Gly Ser Ile Lys Trp Asn
                100                 105                 110

Tyr Lys His His Arg Leu Ser Val Asn Val Thr Ala Leu Thr His Arg
            115                 120                 125

Pro Asn Ile Leu Ile Pro Gly Thr Leu Glu Ser Gly Cys Pro Gln Asn
        130                 135                 140

Leu Thr Cys Ser Val Pro Trp Ala Cys Glu Gln Gly Thr Pro Pro Met
145                 150                 155                 160

Ile Ser Trp Ile Gly Thr Ser Val Ser Pro Leu Asp Pro Ser Thr Thr
                165                 170                 175
```

```
Arg Ser Ser Val Leu Thr Leu Ile Pro Gln Pro Gln Asp His Gly Thr
            180                 185                 190

Ser Leu Thr Cys Gln Val Thr Phe Pro Gly Ala Ser Val Thr Thr Asn
            195                 200                 205

Lys Thr Val His Leu Asn Val Ser Tyr Pro Pro Gln Asn Leu Thr Met
            210                 215                 220

Thr Val Phe Gln Gly Asp Gly Thr Val Ser Thr Val Leu Gly Asn Gly
225                 230                 235                 240

Ser Ser Leu Ser Leu Pro Glu Gly Gln Ser Leu Arg Leu Val Cys Ala
            245                 250                 255

Val Asp Ala Val Asp Ser Asn Pro Pro Ala Arg Leu Ser Leu Ser Trp
            260                 265                 270

Arg Gly Leu Thr Leu Cys Pro Ser Gln Pro Ser Asn Pro Gly Val Leu
            275                 280                 285

Glu Leu Pro Trp Val His Leu Arg Asp Ala Ala Glu Phe Thr Cys Arg
            290                 295                 300

Ala Gln Asn Pro Leu Gly Ser Gln Gln Val Tyr Leu Asn Val Ser Leu
305                 310                 315                 320

Gln Ser Lys Ala Thr Ser Gly Val Thr Gln Gly Val Val Gly Gly Ala
            325                 330                 335

Gly Ala Thr Ala Leu Val Phe Leu Ser Phe Cys Val Ile Phe Val Val
            340                 345                 350

Val Arg Ser Cys Arg Lys Lys Ser Ala Arg Pro Ala Ala Gly Val Gly
            355                 360                 365

Asp Thr Gly Ile Glu Asp Ala Asn Ala Val Arg Gly Ser Ala Ser Gln
            370                 375                 380

Gly Pro Leu Thr Glu Pro Trp Ala Glu Asp Ser Pro Pro Asp Gln Pro
385                 390                 395                 400

Pro Pro Ala Ser Ala Arg Ser Ser Val Gly Glu Gly Glu Leu Gln Tyr
            405                 410                 415

Ala Ser Leu Ser Phe Gln Met Val Lys Pro Trp Asp Ser Arg Gly Gln
            420                 425                 430

Glu Ala Thr Asp Thr Glu Tyr Ser Glu Ile Lys Ile His Arg
            435                 440                 445

<210> SEQ ID NO 5
<211> LENGTH: 347
<212> TYPE: PRT
<213> ORGANISM: homo sapiens

<400> SEQUENCE: 5

Asp Pro Asn Phe Trp Leu Gln Val Gln Glu Ser Val Thr Val Gln Glu
1               5                   10                  15

Gly Leu Cys Val Leu Val Pro Cys Thr Phe Phe His Pro Ile Pro Tyr
            20                  25                  30

Tyr Asp Lys Asn Ser Pro Val His Gly Tyr Trp Phe Arg Glu Gly Ala
            35                  40                  45

Ile Ile Ser Gly Asp Ser Pro Val Ala Thr Asn Lys Leu Asp Gln Glu
        50                  55                  60

Val Gln Glu Glu Thr Gln Gly Arg Phe Arg Leu Leu Gly Asp Pro Ser
65                  70                  75                  80

Arg Asn Asn Cys Ser Leu Ser Ile Val Asp Ala Arg Arg Arg Asp Asn
            85                  90                  95

Gly Ser Tyr Phe Phe Arg Met Glu Arg Gly Ser Thr Lys Tyr Ser Tyr
```

```
              100                 105                 110
Lys Ser Pro Gln Leu Ser Val His Val Thr Asp Leu Thr His Arg Pro
            115                 120                 125

Lys Ile Leu Ile Pro Gly Thr Leu Glu Pro Gly His Ser Lys Asn Leu
130                 135                 140

Thr Cys Ser Val Ser Trp Ala Cys Glu Gln Gly Thr Pro Pro Ile Phe
145                 150                 155                 160

Ser Trp Leu Ser Ala Ala Pro Thr Ser Leu Gly Pro Arg Thr Thr His
                165                 170                 175

Ser Ser Val Leu Ile Ile Thr Pro Arg Pro Gln Asp His Gly Thr Asn
            180                 185                 190

Leu Thr Cys Gln Val Lys Phe Ala Gly Ala Gly Val Thr Thr Glu Arg
        195                 200                 205

Thr Ile Gln Leu Asn Val Thr Tyr Val Pro Gln Asn Pro Thr Thr Gly
    210                 215                 220

Ile Phe Pro Gly Asp Gly Ser Gly Lys Gln Glu Thr Arg Ala Gly Val
225                 230                 235                 240

Val His Gly Ala Ile Gly Gly Ala Gly Val Thr Ala Leu Leu Ala Leu
                245                 250                 255

Cys Leu Cys Leu Ile Phe Phe Ile Val Lys Thr His Arg Arg Lys Ala
            260                 265                 270

Ala Arg Thr Ala Val Gly Arg Asn Asp Thr His Pro Thr Thr Gly Ser
        275                 280                 285

Ala Ser Pro Lys His Gln Lys Lys Ser Lys Leu His Gly Pro Thr Glu
    290                 295                 300

Thr Ser Ser Cys Ser Gly Ala Ala Pro Thr Val Glu Met Asp Glu Glu
305                 310                 315                 320

Leu His Tyr Ala Ser Leu Asn Phe His Gly Met Asn Pro Ser Lys Asp
                325                 330                 335

Thr Ser Glu Tyr Ser Glu Val Arg Thr Gln
            340                 345

<210> SEQ ID NO 6
<211> LENGTH: 535
<212> TYPE: PRT
<213> ORGANISM: homo sapiens

<400> SEQUENCE: 6

Glu Lys Pro Val Tyr Glu Leu Gln Val Gln Lys Ser Val Thr Val Gln
1               5                   10                  15

Glu Gly Leu Cys Val Leu Val Pro Cys Ser Phe Ser Tyr Pro Trp Arg
            20                  25                  30

Ser Trp Tyr Ser Ser Pro Pro Leu Tyr Val Tyr Trp Phe Arg Asp Gly
        35                  40                  45

Glu Ile Pro Tyr Tyr Ala Glu Val Val Ala Thr Asn Asn Pro Asp Arg
    50                  55                  60

Arg Val Lys Pro Glu Thr Gln Gly Arg Phe Arg Leu Leu Gly Asp Val
65                  70                  75                  80

Gln Lys Lys Asn Cys Ser Leu Ser Ile Gly Asp Ala Arg Met Glu Asp
                85                  90                  95

Thr Gly Ser Tyr Phe Phe Arg Val Glu Arg Gly Arg Asp Val Lys Tyr
            100                 105                 110

Ser Tyr Gln Gln Asn Lys Leu Asn Leu Glu Val Thr Ala Leu Ile Glu
        115                 120                 125
```

```
Lys Pro Asp Ile His Phe Leu Glu Pro Leu Glu Ser Gly Arg Pro Thr
130                 135                 140

Arg Leu Ser Cys Ser Leu Pro Gly Ser Cys Glu Ala Gly Pro Pro Leu
145                 150                 155                 160

Thr Phe Ser Trp Thr Gly Asn Ala Leu Ser Pro Leu Asp Pro Glu Thr
                165                 170                 175

Thr Arg Ser Ser Glu Leu Thr Leu Thr Pro Arg Pro Glu Asp His Gly
                180                 185                 190

Thr Asn Leu Thr Cys Gln Met Lys Arg Gln Gly Ala Gln Val Thr Thr
                195                 200                 205

Glu Arg Thr Val Gln Leu Asn Val Ser Tyr Ala Pro Gln Thr Ile Thr
210                 215                 220

Ile Phe Arg Asn Gly Ile Ala Leu Glu Ile Leu Gln Asn Thr Ser Tyr
225                 230                 235                 240

Leu Pro Val Leu Glu Gly Gln Ala Leu Arg Leu Leu Cys Asp Ala Pro
                245                 250                 255

Ser Asn Pro Pro Ala His Leu Ser Trp Phe Gln Gly Ser Pro Ala Leu
                260                 265                 270

Asn Ala Thr Pro Ile Ser Asn Thr Gly Ile Leu Glu Leu Arg Arg Val
                275                 280                 285

Arg Ser Ala Glu Glu Gly Gly Phe Thr Cys Arg Ala Gln His Pro Leu
290                 295                 300

Gly Phe Leu Gln Ile Phe Leu Asn Leu Ser Val Tyr Ser Leu Pro Gln
305                 310                 315                 320

Leu Leu Gly Pro Ser Cys Ser Trp Glu Ala Glu Gly Leu His Cys Arg
                325                 330                 335

Cys Ser Phe Arg Ala Arg Pro Ala Pro Ser Leu Cys Trp Arg Leu Glu
                340                 345                 350

Glu Lys Pro Leu Glu Gly Asn Ser Ser Gln Gly Ser Phe Lys Val Asn
                355                 360                 365

Ser Ser Ser Ala Gly Pro Trp Ala Asn Ser Ser Leu Ile Leu His Gly
                370                 375                 380

Gly Leu Ser Ser Asp Leu Lys Val Ser Cys Lys Ala Trp Asn Ile Tyr
385                 390                 395                 400

Gly Ser Gln Ser Gly Ser Val Leu Leu Leu Gln Gly Arg Ser Asn Leu
                405                 410                 415

Gly Thr Gly Val Val Pro Ala Ala Leu Gly Gly Ala Gly Val Met Ala
                420                 425                 430

Leu Leu Cys Ile Cys Leu Cys Leu Ile Phe Phe Leu Ile Val Lys Ala
                435                 440                 445

Arg Arg Lys Gln Ala Ala Gly Arg Pro Glu Lys Met Asp Asp Glu Asp
450                 455                 460

Pro Ile Met Gly Thr Ile Thr Ser Gly Ser Arg Lys Lys Pro Trp Pro
465                 470                 475                 480

Asp Ser Pro Gly Asp Gln Ala Ser Pro Gly Asp Ala Pro Pro Leu
                485                 490                 495

Glu Glu Gln Lys Glu Leu His Tyr Ala Ser Leu Ser Phe Ser Glu Met
                500                 505                 510

Lys Ser Arg Glu Pro Lys Asp Gln Glu Ala Pro Ser Thr Thr Glu Tyr
                515                 520                 525

Ser Glu Ile Lys Thr Ser Lys
530                 535
```

<210> SEQ ID NO 7
<211> LENGTH: 411
<212> TYPE: PRT
<213> ORGANISM: homo sapiens

<400> SEQUENCE: 7

Gln Glu Arg Arg Phe Gln Leu Glu Gly Pro Glu Ser Leu Thr Val Gln
1               5                   10                  15

Glu Gly Leu Cys Val Leu Val Pro Cys Arg Leu Pro Thr Thr Leu Pro
            20                  25                  30

Ala Ser Tyr Tyr Gly Tyr Gly Tyr Trp Phe Leu Glu Gly Ala Asp Val
        35                  40                  45

Pro Val Ala Thr Asn Asp Pro Asp Glu Glu Val Gln Glu Glu Thr Arg
50                  55                  60

Gly Arg Phe His Leu Leu Trp Asp Pro Arg Arg Lys Asn Cys Ser Leu
65                  70                  75                  80

Ser Ile Arg Asp Ala Arg Arg Asp Asn Ala Ala Tyr Phe Phe Arg
                85                  90                  95

Leu Lys Ser Lys Trp Met Lys Tyr Gly Tyr Thr Ser Ser Lys Leu Ser
                100                 105                 110

Val Arg Val Met Ala Leu Thr His Arg Pro Asn Ile Ser Ile Pro Gly
            115                 120                 125

Thr Leu Glu Ser Gly His Pro Ser Asn Leu Thr Cys Ser Val Pro Trp
130                 135                 140

Val Cys Glu Gln Gly Thr Pro Pro Ile Phe Ser Trp Met Ser Ala Ala
145                 150                 155                 160

Pro Thr Ser Leu Gly Pro Arg Thr Thr Gln Ser Ser Val Leu Thr Ile
                165                 170                 175

Thr Pro Arg Pro Gln Asp His Ser Thr Asn Leu Thr Cys Gln Val Thr
            180                 185                 190

Phe Pro Gly Ala Gly Val Thr Met Glu Arg Thr Ile Gln Leu Asn Val
        195                 200                 205

Ser Ser Phe Lys Ile Leu Gln Asn Thr Ser Ser Leu Pro Val Leu Glu
210                 215                 220

Gly Gln Ala Leu Arg Leu Leu Cys Asp Ala Asp Gly Asn Pro Pro Ala
225                 230                 235                 240

His Leu Ser Trp Phe Gln Gly Phe Pro Ala Leu Asn Ala Thr Pro Ile
                245                 250                 255

Ser Asn Thr Gly Val Leu Glu Leu Pro Gln Val Gly Ser Ala Glu Glu
            260                 265                 270

Gly Asp Phe Thr Cys Arg Ala Gln His Pro Leu Gly Ser Leu Gln Ile
        275                 280                 285

Ser Leu Ser Leu Phe Val His Trp Lys Pro Glu Gly Arg Ala Gly Gly
290                 295                 300

Val Leu Gly Ala Val Trp Gly Ala Ser Ile Thr Thr Leu Val Phe Leu
305                 310                 315                 320

Cys Val Cys Phe Ile Phe Arg Val Lys Thr Arg Arg Lys Lys Ala Ala
                325                 330                 335

Gln Pro Val Gln Asn Thr Asp Asp Val Asn Pro Val Met Val Ser Gly
            340                 345                 350

Ser Arg Gly His Gln His Gln Phe Gln Thr Gly Ile Val Ser Asp His
        355                 360                 365

Pro Ala Glu Ala Gly Pro Ile Ser Glu Asp Glu Gln Glu Leu His Tyr
370                 375                 380

```
Ala Val Leu His Phe His Lys Val Gln Pro Gln Glu Pro Lys Val Thr
385                 390                 395                 400

Asp Thr Glu Tyr Ser Glu Ile Lys Ile His Lys
            405                 410
```

<210> SEQ ID NO 8
<211> LENGTH: 483
<212> TYPE: PRT
<213> ORGANISM: homo sapiens

<400> SEQUENCE: 8

```
Met Glu Gly Asp Arg Gln Tyr Gly Asp Gly Tyr Leu Leu Gln Val Gln
1               5                   10                  15

Glu Leu Val Thr Val Gln Glu Gly Leu Cys Val His Val Pro Cys Ser
            20                  25                  30

Phe Ser Tyr Pro Gln Asp Gly Trp Thr Asp Ser Asp Pro Val His Gly
        35                  40                  45

Tyr Trp Phe Arg Ala Gly Asp Arg Pro Tyr Gln Asp Ala Pro Val Ala
    50                  55                  60

Thr Asn Asn Pro Asp Arg Glu Val Gln Ala Glu Thr Gln Gly Arg Phe
65                  70                  75                  80

Gln Leu Leu Gly Asp Ile Trp Ser Asn Asp Cys Ser Leu Ser Ile Arg
                85                  90                  95

Asp Ala Arg Lys Arg Asp Lys Ser Tyr Phe Phe Arg Leu Glu Arg
            100                 105                 110

Gly Ser Met Lys Trp Ser Tyr Lys Ser Gln Leu Asn Tyr Lys Thr Lys
            115                 120                 125

Gln Leu Ser Val Phe Val Thr Ala Leu Thr His Arg Pro Asp Ile Leu
130                 135                 140

Ile Leu Gly Thr Leu Glu Ser Gly His Ser Arg Asn Leu Thr Cys Ser
145                 150                 155                 160

Val Pro Trp Ala Cys Lys Gln Gly Thr Pro Pro Met Ile Ser Trp Ile
                165                 170                 175

Gly Ala Ser Val Ser Ser Pro Gly Pro Thr Thr Ala Arg Ser Ser Val
            180                 185                 190

Leu Thr Leu Thr Pro Lys Pro Gln Asp His Gly Thr Ser Leu Thr Cys
        195                 200                 205

Gln Val Thr Leu Pro Gly Thr Gly Val Thr Thr Thr Ser Thr Val Arg
    210                 215                 220

Leu Asp Val Ser Tyr Pro Pro Trp Asn Leu Thr Met Thr Val Phe Gln
225                 230                 235                 240

Gly Asp Ala Thr Ala Ser Thr Ala Leu Gly Asn Gly Ser Ser Leu Ser
                245                 250                 255

Val Leu Glu Gly Gln Ser Leu Arg Leu Val Cys Ala Val Asn Ser Asn
            260                 265                 270

Pro Pro Ala Arg Leu Ser Trp Thr Arg Gly Ser Leu Thr Leu Cys Pro
        275                 280                 285

Ser Arg Ser Ser Asn Pro Gly Leu Leu Glu Leu Pro Arg Val His Val
    290                 295                 300

Arg Asp Glu Gly Glu Phe Thr Cys Arg Ala Gln Asn Ala Gln Gly Ser
305                 310                 315                 320

Gln His Ile Ser Leu Ser Leu Ser Leu Gln Asn Glu Gly Thr Gly Thr
                325                 330                 335

Ser Arg Pro Val Ser Gln Val Thr Leu Ala Ala Val Gly Gly Ala Gly
            340                 345                 350
```

```
Ala Thr Ala Leu Ala Phe Leu Ser Phe Cys Ile Ile Phe Ile Ile Val
            355                 360                 365

Arg Ser Cys Arg Lys Ser Ala Arg Pro Ala Ala Gly Val Gly Asp
    370                 375                 380

Thr Gly Met Glu Asp Ala Lys Ala Ile Arg Gly Ser Ala Ser Gln Gly
385                 390                 395                 400

Pro Leu Thr Glu Ser Trp Lys Asp Gly Asn Pro Leu Lys Lys Pro Pro
                405                 410                 415

Pro Ala Val Ala Pro Ser Ser Gly Glu Gly Glu Leu His Tyr Ala
            420                 425                 430

Thr Leu Ser Phe His Lys Val Lys Pro Gln Asp Pro Gln Gly Gln Glu
                435                 440                 445

Ala Thr Asp Ser Glu Tyr Ser Glu Ile Lys Ile His Lys Arg Glu Thr
            450                 455                 460

Ala Glu Thr Gln Ala Cys Leu Arg Asn His Asn Pro Ser Ser Lys Glu
465                 470                 475                 480

Val Arg Gly

<210> SEQ ID NO 9
<211> LENGTH: 670
<212> TYPE: PRT
<213> ORGANISM: homo sapiens

<400> SEQUENCE: 9

Asn Lys Asp Pro Ser Tyr Ser Leu Gln Val Gln Arg Gln Val Pro Val
1               5                   10                  15

Pro Glu Gly Leu Cys Val Ile Val Ser Cys Asn Leu Ser Tyr Pro Arg
            20                  25                  30

Asp Gly Trp Asp Glu Ser Thr Ala Ala Tyr Gly Tyr Trp Phe Lys Gly
        35                  40                  45

Arg Thr Ser Pro Lys Thr Gly Ala Pro Val Ala Thr Asn Asn Gln Ser
50                  55                  60

Arg Glu Val Glu Met Ser Thr Arg Asp Arg Phe Gln Leu Thr Gly Asp
65                  70                  75                  80

Pro Gly Lys Gly Ser Cys Ser Leu Val Ile Arg Asp Ala Gln Arg Glu
                85                  90                  95

Asp Glu Ala Trp Tyr Phe Phe Arg Val Glu Arg Gly Ser Arg Val Arg
            100                 105                 110

His Ser Phe Leu Ser Asn Ala Phe Phe Leu Lys Val Thr Ala Leu Thr
        115                 120                 125

Lys Lys Pro Asp Val Tyr Ile Pro Glu Thr Leu Glu Pro Gly Gln Pro
130                 135                 140

Val Thr Val Ile Cys Val Phe Asn Trp Ala Phe Lys Lys Cys Pro Ala
145                 150                 155                 160

Pro Ser Phe Ser Trp Thr Gly Ala Ala Leu Ser Pro Arg Arg Thr Arg
                165                 170                 175

Pro Ser Thr Ser His Phe Ser Val Leu Ser Phe Thr Pro Ser Pro Gln
            180                 185                 190

Asp His Asp Thr Asp Leu Thr Cys His Val Asp Phe Ser Arg Lys Gly
        195                 200                 205

Val Ser Ala Gln Arg Thr Val Arg Leu Arg Val Ala Tyr Ala Pro Lys
210                 215                 220

Asp Leu Ile Ile Ser Ile Ser His Asp Asn Thr Ser Ala Leu Glu Leu
225                 230                 235                 240
```

```
Gln Gly Asn Val Ile Tyr Leu Glu Val Gln Lys Gly Gln Phe Leu Arg
            245                 250                 255

Leu Leu Cys Ala Ala Asp Ser Gln Pro Ala Thr Leu Ser Trp Val
        260                 265                 270

Leu Gln Asp Arg Val Leu Ser Ser His Pro Trp Gly Pro Arg Thr
    275                 280                 285

Leu Gly Leu Glu Leu Arg Gly Val Arg Ala Gly Asp Ser Gly Arg Tyr
    290                 295                 300

Thr Cys Arg Ala Glu Asn Arg Leu Gly Ser Gln Gln Gln Ala Leu Asp
305                 310                 315                 320

Leu Ser Val Gln Tyr Pro Pro Glu Asn Leu Arg Val Met Val Ser Gln
            325                 330                 335

Ala Asn Arg Thr Val Leu Glu Asn Leu Gly Asn Gly Thr Ser Leu Pro
            340                 345                 350

Val Leu Glu Gly Gln Ser Leu Arg Leu Val Cys Val Thr His Ser Ser
            355                 360                 365

Pro Pro Ala Arg Leu Ser Trp Thr Arg Trp Gly Gln Thr Val Gly Pro
370                 375                 380

Ser Gln Pro Ser Asp Pro Gly Val Leu Glu Leu Pro Pro Ile Gln Met
385                 390                 395                 400

Glu His Glu Gly Glu Phe Thr Cys His Ala Gln His Pro Leu Gly Ser
                405                 410                 415

Gln His Val Ser Leu Ser Leu Ser Val His Tyr Pro Pro Gln Leu Leu
            420                 425                 430

Gly Pro Ser Cys Ser Trp Glu Ala Glu Gly Leu His Cys Ser Cys Ser
            435                 440                 445

Ser Gln Ala Ser Pro Ala Pro Ser Leu Arg Trp Trp Leu Gly Glu Glu
    450                 455                 460

Leu Leu Glu Gly Asn Ser Ser Gln Gly Ser Phe Glu Val Thr Pro Ser
465                 470                 475                 480

Ser Ala Gly Pro Trp Ala Asn Ser Ser Leu Ser Leu His Gly Gly Leu
                485                 490                 495

Ser Ser Gly Leu Arg Leu Arg Cys Lys Ala Trp Asn Val His Gly Ala
            500                 505                 510

Gln Ser Gly Ser Val Phe Gln Leu Leu Pro Gly Lys Leu Glu His Gly
            515                 520                 525

Gly Gly Leu Gly Leu Gly Ala Ala Leu Gly Ala Gly Val Ala Ala Leu
    530                 535                 540

Leu Ala Phe Cys Ser Cys Leu Val Val Phe Arg Val Lys Ile Cys Arg
545                 550                 555                 560

Lys Glu Ala Arg Lys Arg Ala Ala Ala Glu Gln Asp Val Pro Ser Thr
                565                 570                 575

Leu Gly Pro Ile Ser Gln Gly His Gln His Glu Cys Ser Ala Gly Ser
            580                 585                 590

Ser Gln Asp His Pro Pro Pro Gly Ala Ala Thr Tyr Thr Pro Gly Lys
            595                 600                 605

Gly Glu Glu Gln Glu Leu His Tyr Ala Ser Leu Ser Phe Gln Gly Leu
    610                 615                 620

Arg Leu Trp Glu Pro Ala Asp Gln Glu Ala Pro Ser Thr Thr Glu Tyr
625                 630                 635                 640

Ser Glu Ile Lys Ile His Thr Gly Gln Pro Leu Arg Gly Pro Gly Phe
                645                 650                 655
```

Gly Leu Gln Leu Glu Arg Glu Met Ser Gly Met Val Pro Lys
                660                 665                 670

<210> SEQ ID NO 10
<211> LENGTH: 577
<212> TYPE: PRT
<213> ORGANISM: homo sapiens

<400> SEQUENCE: 10

Lys Glu Gln Lys Asp Tyr Leu Leu Thr Met Gln Lys Ser Val Thr Val
1               5                   10                  15

Gln Glu Gly Leu Cys Val Ser Val Leu Cys Ser Phe Ser Tyr Pro Gln
                20                  25                  30

Asn Gly Trp Thr Ala Ser Asp Pro Val His Gly Tyr Trp Phe Arg Ala
            35                  40                  45

Gly Asp His Val Ser Arg Asn Ile Pro Val Ala Thr Asn Asn Pro Ala
50                  55                  60

Arg Ala Val Gln Glu Glu Thr Arg Asp Arg Phe His Leu Leu Gly Asp
65                  70                  75                  80

Pro Gln Asn Lys Asp Cys Thr Leu Ser Ile Arg Asp Thr Arg Glu Ser
                85                  90                  95

Asp Ala Gly Thr Tyr Val Phe Cys Val Glu Arg Gly Asn Met Lys Trp
            100                 105                 110

Asn Tyr Lys Tyr Asp Gln Leu Ser Val Asn Val Thr Ala Ser Gln Asp
        115                 120                 125

Leu Leu Ser Arg Tyr Arg Leu Glu Val Pro Glu Ser Val Thr Val Gln
130                 135                 140

Glu Gly Leu Cys Val Ser Val Pro Cys Ser Val Leu Tyr Pro His Tyr
145                 150                 155                 160

Asn Trp Thr Ala Ser Ser Pro Val Tyr Gly Ser Trp Phe Lys Glu Gly
                165                 170                 175

Ala Asp Ile Pro Trp Asp Ile Pro Val Ala Thr Asn Thr Pro Ser Gly
            180                 185                 190

Lys Val Gln Glu Asp Thr His Gly Arg Phe Leu Leu Leu Gly Asp Pro
        195                 200                 205

Gln Thr Asn Asn Cys Ser Leu Ser Ile Arg Asp Ala Arg Lys Gly Asp
210                 215                 220

Ser Gly Lys Tyr Tyr Phe Gln Val Glu Arg Gly Ser Arg Lys Trp Asn
225                 230                 235                 240

Tyr Ile Tyr Asp Lys Leu Ser Val His Val Thr Ala Leu Thr His Met
                245                 250                 255

Pro Thr Phe Ser Ile Pro Gly Thr Leu Glu Ser Gly His Pro Arg Asn
            260                 265                 270

Leu Thr Cys Ser Val Pro Trp Ala Cys Glu Gln Gly Thr Pro Pro Thr
        275                 280                 285

Ile Thr Trp Met Gly Ala Ser Val Ser Ser Leu Asp Pro Thr Ile Thr
290                 295                 300

Arg Ser Ser Met Leu Ser Leu Ile Pro Gln Pro Gln Asp His Gly Thr
305                 310                 315                 320

Ser Leu Thr Cys Gln Val Thr Leu Pro Gly Ala Gly Val Thr Met Thr
                325                 330                 335

Arg Ala Val Arg Leu Asn Ile Ser Tyr Pro Pro Gln Asn Leu Thr Met
            340                 345                 350

Thr Val Phe Gln Gly Asp Gly Thr Ala Ser Thr Thr Leu Arg Asn Gly
        355                 360                 365

```
Ser Ala Leu Ser Val Leu Glu Gly Gln Ser Leu His Leu Val Cys Ala
        370                 375                 380

Val Asp Ser Asn Pro Pro Ala Arg Leu Ser Trp Thr Trp Gly Ser Leu
385                 390                 395                 400

Thr Leu Ser Pro Ser Gln Ser Ser Asn Leu Gly Val Leu Glu Leu Pro
                405                 410                 415

Arg Val His Val Lys Asp Glu Gly Phe Thr Cys Arg Ala Gln Asn
            420                 425                 430

Pro Leu Gly Ser Gln His Ile Ser Leu Ser Leu Ser Leu Gln Asn Glu
            435                 440                 445

Tyr Thr Gly Lys Met Arg Pro Ile Ser Gly Val Thr Leu Gly Ala Phe
    450                 455                 460

Gly Gly Ala Gly Ala Thr Ala Leu Val Phe Leu Tyr Phe Cys Ile Ile
465                 470                 475                 480

Phe Val Val Val Arg Ser Cys Arg Lys Lys Ser Ala Arg Pro Ala Val
                485                 490                 495

Gly Val Gly Asp Thr Gly Met Glu Asp Ala Asn Ala Val Arg Gly Ser
                500                 505                 510

Ala Ser Gln Gly Pro Leu Ile Glu Ser Pro Ala Asp Asp Ser Pro Pro
            515                 520                 525

His His Ala Pro Pro Ala Leu Ala Thr Pro Ser Pro Glu Glu Gly Glu
            530                 535                 540

Ile Gln Tyr Ala Ser Leu Ser Phe His Lys Ala Arg Pro Gln Tyr Pro
545                 550                 555                 560

Gln Glu Gln Glu Ala Ile Gly Tyr Glu Tyr Ser Glu Ile Asn Ile Pro
                565                 570                 575

Lys

<210> SEQ ID NO 11
<211> LENGTH: 481
<212> TYPE: PRT
<213> ORGANISM: homo sapiens

<400> SEQUENCE: 11

Met Leu Leu Leu Pro Leu Leu Leu Pro Val Leu Gly Ala Gly Ser Leu
1               5                   10                  15

Asn Lys Asp Pro Ser Tyr Ser Leu Gln Val Gln Arg Gln Val Pro Val
            20                  25                  30

Pro Glu Gly Leu Cys Val Ile Val Ser Cys Asn Leu Ser Tyr Pro Arg
        35                  40                  45

Asp Gly Trp Asp Glu Ser Thr Ala Ala Tyr Gly Tyr Trp Phe Lys Gly
    50                  55                  60

Arg Thr Ser Pro Lys Thr Gly Ala Pro Val Ala Thr Asn Asn Gln Ser
65                  70                  75                  80

Arg Glu Val Ala Met Ser Thr Arg Asp Arg Phe Gln Leu Thr Gly Asp
                85                  90                  95

Pro Gly Lys Gly Ser Cys Ser Leu Val Ile Arg Asp Ala Gln Arg Glu
            100                 105                 110

Asp Glu Ala Trp Tyr Phe Phe Arg Val Glu Arg Gly Ser Arg Val Arg
        115                 120                 125

His Ser Phe Leu Ser Asn Ala Phe Phe Leu Lys Val Thr Ala Leu Thr
    130                 135                 140

Gln Lys Pro Asp Val Tyr Ile Pro Glu Thr Leu Glu Pro Gly Gln Pro
145                 150                 155                 160
```

```
Val Thr Val Ile Cys Val Phe Asn Trp Ala Phe Lys Lys Cys Pro Ala
                165                 170                 175

Pro Ser Phe Ser Trp Thr Gly Ala Ala Leu Ser Pro Arg Arg Thr Arg
            180                 185                 190

Pro Ser Thr Ser His Phe Ser Val Leu Ser Phe Thr Pro Ser Pro Gln
            195                 200                 205

Asp His Asp Thr Asp Leu Thr Cys His Val Asp Phe Ser Arg Lys Gly
        210                 215                 220

Val Ser Ala Gln Arg Thr Val Arg Leu Arg Val Ala Ser Leu Glu Leu
225                 230                 235                 240

Gln Gly Asn Val Ile Tyr Leu Glu Val Gln Lys Gly Gln Phe Leu Arg
                245                 250                 255

Leu Leu Cys Ala Ala Asp Ser Gln Pro Pro Ala Thr Leu Ser Trp Val
            260                 265                 270

Leu Gln Asp Arg Val Leu Ser Ser His Pro Trp Gly Pro Arg Thr
            275                 280                 285

Leu Gly Leu Glu Leu Pro Gly Val Lys Ala Gly Asp Ser Gly Arg Tyr
            290                 295                 300

Thr Cys Arg Ala Glu Asn Arg Leu Gly Ser Gln Gln Arg Ala Leu Asp
305                 310                 315                 320

Leu Ser Val Gln Tyr Pro Pro Glu Asn Leu Arg Val Met Val Ser Gln
                325                 330                 335

Ala Asn Arg Thr Val Leu Glu Asn Leu Arg Asn Gly Thr Ser Leu Arg
            340                 345                 350

Val Leu Glu Gly Gln Ser Leu Arg Leu Val Cys Val Thr His Ser Ser
            355                 360                 365

Pro Pro Ala Arg Leu Ser Trp Thr Trp Gly Glu Gln Thr Val Gly Pro
            370                 375                 380

Ser Gln Pro Ser Asp Pro Gly Val Leu Gln Leu Pro Arg Val Gln Met
385                 390                 395                 400

Glu His Glu Gly Glu Phe Thr Cys His Ala Arg His Pro Leu Gly Ser
                405                 410                 415

Gln Arg Val Ser Leu Ser Phe Ser Val His Cys Lys Ser Gly Pro Met
            420                 425                 430

Thr Gly Val Val Leu Val Ala Val Gly Glu Val Ala Met Lys Ile Leu
            435                 440                 445

Leu Leu Cys Leu Cys Leu Ile Leu Leu Arg Val Arg Ser Cys Arg Arg
450                 455                 460

Lys Ala Ala Arg Ala Ala Leu Gly Met Glu Ala Ala Asp Ala Val Thr
465                 470                 475                 480

Asp

<210> SEQ ID NO 12
<211> LENGTH: 127
<212> TYPE: PRT
<213> ORGANISM: mus musculus

<400> SEQUENCE: 12

Gln Ile Gln Leu Gln Gln Ser Gly Ala Glu Leu Glu Lys Pro Gly Ala
1               5                   10                  15

Ser Val Lys Met Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45
```

Gly Tyr Ile Asn Pro Asp Thr Asp Ser Thr Glu Tyr Asn Gln Lys Phe
            50                  55                  60

Arg Asp Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                    85                  90                  95

Ala Arg Pro Tyr Tyr Arg Tyr Ala Gly Tyr Ala Met Asp Tyr Trp Gly
                100                 105                 110

Gln Gly Thr Ser Val Thr Val Ser Ser Ala Ser Thr Lys Gly Pro
            115                 120                 125

<210> SEQ ID NO 13
<211> LENGTH: 113
<212> TYPE: PRT
<213> ORGANISM: mus musculus

<400> SEQUENCE: 13

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Val Tyr Ser Leu Thr Ile Ser Ser Leu Glu Tyr
65                  70                  75                  80

Glu Asp Leu Gly Ile Tyr Tyr Cys Leu Gln Tyr Asp Glu Phe Pro Trp
                85                  90                  95

Thr Phe Gly Gly Gly Thr Lys Leu Glu Ile Lys Arg Thr Val Ala Ala
                100                 105                 110

Pro

<210> SEQ ID NO 14
<211> LENGTH: 5
<212> TYPE: PRT
<213> ORGANISM: mus musculus

<400> SEQUENCE: 14

Ser Tyr Trp Met His
1               5

<210> SEQ ID NO 15
<211> LENGTH: 17
<212> TYPE: PRT
<213> ORGANISM: mus musculus

<400> SEQUENCE: 15

Tyr Ile Asn Pro Asp Thr Asp Ser Thr Glu Tyr Asn Gln Lys Phe Arg
1               5                   10                  15

Asp

<210> SEQ ID NO 16
<211> LENGTH: 12
<212> TYPE: PRT
<213> ORGANISM: mus musculus

<400> SEQUENCE: 16

```
Pro Tyr Tyr Arg Tyr Ala Gly Tyr Ala Met Asp Tyr
1               5                   10
```

<210> SEQ ID NO 17
<211> LENGTH: 11
<212> TYPE: PRT
<213> ORGANISM: mus musculus

<400> SEQUENCE: 17

```
Lys Ala Ser Gln Asp Ile Asn Ser Tyr Leu Ser
1               5                   10
```

<210> SEQ ID NO 18
<211> LENGTH: 7
<212> TYPE: PRT
<213> ORGANISM: mus musculus

<400> SEQUENCE: 18

```
Arg Ala Asn Arg Leu Val Asp
1               5
```

<210> SEQ ID NO 19
<211> LENGTH: 9
<212> TYPE: PRT
<213> ORGANISM: mus musculus

<400> SEQUENCE: 19

```
Leu Gln Tyr Asp Glu Phe Pro Trp Thr
1               5
```

<210> SEQ ID NO 20
<211> LENGTH: 131
<212> TYPE: PRT
<213> ORGANISM: mus musculus

<400> SEQUENCE: 20

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Asp Val Asn Trp Val Arg Gln Pro Pro Gly Lys Gly Leu Glu Trp Leu
        35                  40                  45

Gly Met Ile Trp Gly Asp Gly Ile Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Glu Met Asn Ser Leu Gln Thr Asp Asp Thr Ala Arg Tyr Tyr Cys Ala
                85                  90                  95

Arg Gly Gly Ile Tyr Tyr Phe Gly Asn Thr Tyr Gly Tyr Trp Phe Phe
            100                 105                 110

Asp Val Trp Gly Ala Gly Thr Thr Val Thr Val Ser Ser Ala Ser Thr
        115                 120                 125

Lys Gly Pro
    130
```

<210> SEQ ID NO 21
<211> LENGTH: 118
<212> TYPE: PRT
<213> ORGANISM: mus musculus

<400> SEQUENCE: 21

-continued

```
Asp Ile Val Met Thr Gln Ser Pro Ser Ser Leu Ala Val Ser Thr Gly
1               5                   10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
            100                 105                 110

Arg Thr Val Ala Ala Pro
            115
```

<210> SEQ ID NO 22
<211> LENGTH: 5
<212> TYPE: PRT
<213> ORGANISM: mus musculus

<400> SEQUENCE: 22

```
Asp Tyr Asp Val Asn
1               5
```

<210> SEQ ID NO 23
<211> LENGTH: 16
<212> TYPE: PRT
<213> ORGANISM: Mus musculus

<400> SEQUENCE: 23

```
Met Ile Trp Gly Asp Gly Ile Thr Asp Tyr Asn Ser Ala Leu Lys Ser
1               5                   10                  15
```

<210> SEQ ID NO 24
<211> LENGTH: 17
<212> TYPE: PRT
<213> ORGANISM: Mus musculus

<400> SEQUENCE: 24

```
Gly Gly Ile Tyr Tyr Phe Gly Asn Thr Tyr Gly Tyr Trp Phe Phe Asp
1               5                   10                  15

Val
```

<210> SEQ ID NO 25
<211> LENGTH: 17
<212> TYPE: PRT
<213> ORGANISM: Mus musculus

<400> SEQUENCE: 25

```
Lys Ser Ser Gln Ser Leu Leu Asn Ser Arg Thr Arg Lys Asn Tyr Leu
1               5                   10                  15

Ala
```

<210> SEQ ID NO 26
<211> LENGTH: 7
<212> TYPE: PRT
<213> ORGANISM: Mus musculus

<400> SEQUENCE: 26

```
<210> SEQ ID NO 27
<211> LENGTH: 7
<212> TYPE: PRT
<213> ORGANISM: Mus musculus

<400> SEQUENCE: 27

Gln Ser Tyr Asn Leu Arg Thr
1               5

<210> SEQ ID NO 28
<211> LENGTH: 131
<212> TYPE: PRT
<213> ORGANISM: Mus musculus

<400> SEQUENCE: 28

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Asp Val Asn Trp Val Arg Gln Pro Pro Gly Lys Gly Leu Glu Trp Leu
        35                  40                  45

Gly Met Ile Trp Gly Asp Gly Ile Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Glu Met Asn Ser Leu Gln Thr Asp Asp Thr Ala Arg Tyr Tyr Cys Ala
                85                  90                  95

Arg Gly Gly Ile Tyr Tyr Phe Gly Asn Thr Tyr Gly Tyr Trp Phe Phe
            100                 105                 110

Asp Val Trp Gly Ala Gly Thr Thr Val Thr Val Ser Ser Ala Ser Thr
        115                 120                 125

Lys Gly Pro
    130

<210> SEQ ID NO 29
<211> LENGTH: 118
<212> TYPE: PRT
<213> ORGANISM: Mus musculus

<400> SEQUENCE: 29

Glu Ile Leu Leu Thr Gln Ser Pro Ser Ser Leu Ala Val Ser Thr Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Arg Thr Phe Gly Gly Gly Thr Lys Leu Glu Ile Lys
            100                 105                 110
```

(Trp Ala Ser Thr Arg Glu Ser appears at top of page:)

```
Trp Ala Ser Thr Arg Glu Ser
1               5
```

Arg Thr Val Ala Ala Pro
        115

<210> SEQ ID NO 30
<211> LENGTH: 5
<212> TYPE: PRT
<213> ORGANISM: Mus musculus

<400> SEQUENCE: 30

Asp Tyr Asp Val Asn
1               5

<210> SEQ ID NO 31
<211> LENGTH: 16
<212> TYPE: PRT
<213> ORGANISM: Mus musculus

<400> SEQUENCE: 31

Met Ile Trp Gly Asp Gly Ile Thr Asp Tyr Asn Ser Ala Leu Lys Ser
1               5                   10                  15

<210> SEQ ID NO 32
<211> LENGTH: 17
<212> TYPE: PRT
<213> ORGANISM: Mus musculus

<400> SEQUENCE: 32

Gly Gly Ile Tyr Tyr Phe Gly Asn Thr Tyr Gly Tyr Trp Phe Phe Asp
1               5                   10                  15

Val

<210> SEQ ID NO 33
<211> LENGTH: 17
<212> TYPE: PRT
<213> ORGANISM: Mus musculus

<400> SEQUENCE: 33

Lys Ser Ser Gln Ser Leu Leu Asn Ser Arg Thr Arg Lys Asn Tyr Leu
1               5                   10                  15

Ala

<210> SEQ ID NO 34
<211> LENGTH: 7
<212> TYPE: PRT
<213> ORGANISM: Mus musculus

<400> SEQUENCE: 34

Trp Ala Ser Thr Arg Glu Ser
1               5

<210> SEQ ID NO 35
<211> LENGTH: 8
<212> TYPE: PRT
<213> ORGANISM: Mus musculus

<400> SEQUENCE: 35

Lys Gln Ser Tyr Asn Leu Arg Thr
1               5

SIGLEC-10 ANTIBODIES

CROSS-REFERENCE TO RELATED APPLICATIONS

This application is the U.S. national stage application of International Patent Application No. PCT/EP2016/077955, filed Nov. 17, 2016, which claims the benefit of U.S. Provisional Patent Application No. 62/256,188, filed 17 Nov. 2015, the disclosures of which are hereby incorporated by reference in their entirety.

REFERENCE TO SEQUENCE LISTING

The present application is being filed along with a Sequence Listing in electronic format. The Sequence Listing is provided as a file entitled "Siglec10_ST25", created 17 Nov. 2016, which is 58 KB in size. The information in the electronic format of the Sequence Listing is incorporated herein by reference in its entirety.

FIELD OF THE INVENTION

This invention relates to agents that bind human Siglec-10, including antibodies that neutralize the inhibitory activity of human Siglec-10 in lymphocytes. Such agents can be used for the treatment of cancers or infectious disease.

BACKGROUND OF THE INVENTION

NK cells are mononuclear cell that develop in the bone marrow from lymphoid progenitors, and morphological features and biological properties typically include the expression of the cluster determinants (CDs) CD16, CD56, and/or CD57; the absence of the alpha/beta or gamma/delta TCR complex on the cell surface; the ability to bind to and kill target cells that fail to express "self" major histocompatibility complex (MHC)/human leukocyte antigen (HLA) proteins; and the ability to kill tumor cells or other diseased cells that express ligands for activating NK receptors. NK cells are characterized by their ability to bind and kill several types of tumor cell lines without the need for prior immunization or activation. NK cells can also release soluble proteins and cytokines that exert a regulatory effect on the immune system; and can undergo multiple rounds of cell division and produce daughter cells with similar biologic properties as the parent cell. Normal, healthy cells are protected from lysis by NK cells.

Based on their biological properties, various therapeutic and vaccine strategies have been proposed in the art that rely on a modulation of NK cells. However, NK cell activity is regulated by a complex mechanism that involves both stimulating and inhibitory signals. Briefly, the lytic activity of NK cells is regulated by various cell surface receptors that transduce either positive or negative intracellular signals upon interaction with ligands on the target cell. The balance between positive and negative signals transmitted via these receptors determines whether or not a target cell is lysed (killed) by a NK cell. NK cell stimulatory signals can be mediated by Natural Cytotoxicity Receptors (NCR) such as NKp30, NKp44, and NKp46; as well as NKG2C receptors, NKG2D receptors, certain activating Killer Ig-like Receptors (KIRs), and other activating NK receptors (Lanier, Annual Review of Immunology 2005; 23:225-74). NK cell inhibitory signals can be mediated by receptors like Ly49, CD94/NKG2-A, as well as certain inhibitory KIRs, which recognize major histocompatibility complex (MHC) class I-molecules (Karre et al., Nature 1986; 319:675-8; Öhlén et al, Science 1989; 246:666-8). These inhibitory receptors bind to polymorphic determinants of MHC class I molecules (including HLA class I) present on other cells and inhibit NK cell-mediated lysis.

The lytic activity of NK cells can also be regulated by siglec polypeptides. Siglecs (sialic-acid-binding immunoglobulin-like lectins) are a subset of I-type lectins that bind to sialoglycans and are predominantly expressed on cells of the hematopoietic system in a manner dependent on cell type and differentiation. Whereas sialic acid is ubiquitously expressed, typically at the terminal position of glycoproteins and lipids, only very specific, distinct sialoglycan structures are recognized by individual Siglec receptors, depending on identity and linkage to subterminal carbohydrate moieties. Siglecs have only low general affinity to the common mammalian sialoside structures containing the N-acetylneuraminic acid (Neu5Ac) α2-6 and α2-3 linkages.

Siglecs are generally divided into two groups, a first subset made up of Siglec-1, -2, -4 and -15, and the CD33-related group of Siglecs which includes Siglec-3, -5, -6, -7, -8, -9, 10, -11, -12, -14 and -16. The CD33-related group of Siglecs have been known to undergo rapid internalization. Although the rapid internalization of unmodified siglec antibodies reduces their suitability as tools for induction of antibody-dependent cellular cytotoxicity (ADCC) or complement-mediated cytotoxicity (CDC), antibody binding of Siglecs (e.g. Siglec-8 and CD22) have been reported to induce apoptosis of eosinophils, neutrophils, and depletion of B cells, respectively. One therapeutic agent targeting a CD33-related Siglec has been developed, an anti-CD33 (Siglec3) antibody-drug conjugate known as Mylotarg™ that is rapidly internalized and leads to death of malignant cells. Other Siglecs reported to be expressed by malignant cells include Siglec-9 in acute myeloid leukemia. Reports have proposed that Siglec-10 may function as an inhibitory receptor as it comprises a short cytoplasmic domain that bears two ITIM (inhibitory) signaling motifs (Whitney et al (2001) Eur. J. Biochem. 268:6083-6096). Chen et al. (Nat Biotechnol. 2011 May; 29(5):428-35) report that sialidase mediated disruption of the Siglec-10/CD24 interaction can exacerbate sepsis. Siglec-10 has recently been found expressed on immune effector cells such as NK and T cells. Zhang et al (J Surg Res. 2015 March; 194(1):107-13) reports that Siglec-10 was expressed on tumor infiltrated NK cells in human hepatocellular carcinoma (HCC) and negatively associated with patient survival.

Bandala-Sanchez et al. (2013) Nature Immunol. 14(7): 741-748 reported that soluble CD52 interacts with Siglec-10 to regulate T cells. Chen et al. (Science. 2009 Mar. 27; 323(5922):1722-5.) reported that Siglec-10, but not Siglec-5, -7 or -11, interacts with CD24, a small glycosyl-phophoinositol-anchored protein. This interaction selectively represses tissue damage-caused immune responses.

Despite the interest in Siglec-10, to date, however, no candidate therapeutic agents that neutralize Siglec-10 have been reported. One possible reason for the lack of therapeutic agents directed to human Siglec-10 is that it may not be possible to block the interaction of Siglec-10 with its various sialic acid ligands using a single molecule such as a monoclonal antibody. Furthermore, even if it were possible to block sialic ligand binding sites it may be difficult to block only Siglec-10 and not other closely related Siglecs. To date only polyclonal antibodies have been reported to have the ability to partially block the interaction of Siglec-10 with sialic acid (antibody AF2130, Antigen Affinity-purified Polyclonal Goat IgG, available from RD Systems, Inc.).

However, the interaction concerned a single, and moreover non-cell surface expressed, sialic acid (6'-SialyllactosePoly-acrylamide), and the antibodies are described as partially cross-reactive with Siglec-5. In view of the only example being a polyclonal antibody, binding to multiple sites on Siglec-10 may be required in order to block binding to sialic acids and/or cause steric hindrance that blocks sialic acid binding. Another possibility for the lack of anti-Siglec-10 therapeutic agents is that the sialylation of proteins such as CD52 that have been reported to interact with Siglec-10 may not be representative of the range of sialylation on human tumor cells ( ), such that antibodies that might inhibit CD52/Siglec-10 interactions will not be effective to inhibit Siglec-10 signaling induced by tumor cells nor potentiate cytotoxicity by Siglec-10 expressing effector cells against target (e.g. tumor) cells.

One therapeutic approach that may modulate Siglec-10, although not intended as antagonists nor aimed specifically at Siglec-10, has been to use of a recombinant CD24 IgG1 Fc fusion proteins (see, e.g., Toubai et al. (2014) Blood 123(22):3512-3523). These proteins have been proposed to induce Siglec agonism as potential treatments for autoimmune disease such as multiple sclerosis or GvHD. However, CD24 proteins are promiscuous for Siglec binding and are expected to bind Siglecs other than Siglec-10. Insofar different Siglecs can have differing expression profiles and moreover may have opposing activity, such an approach may imply a risk of toxicities or side effects.

Consequently, there remains a need for an agent capable of inhibiting human Siglec-10 with selectivity.

SUMMARY OF THE INVENTION

The present invention provides agents capable of binding human Siglec-10 with specificity and inhibiting the binding between Siglec-10 and its sialic acid ligands on tumor cells, including human carcinoma cells that express high levels of Siglec-10 ligands. The exemplary agents (antibodies) can be useful to neutralize the inhibitory activity of Siglec-10 in a lymphocyte (e.g. NK cell, T cell) and, in turn, enhance the activity (e.g. cytotoxicity) of a Siglec-10 expressing lymphocyte towards a tumor target cell. The agents can, in particular, inhibit Siglec-10 binding to high sialic-acid expressing tumor cells. Furthermore, unlike CD24 agents, the present agents (e.g. antibodies) offer the advantage of selectivity over other CD33-related Siglecs, notably Siglec-11 which possesses a variable sialic acid binding domain that is identical to Siglec-16 which in turn may be an activating receptor with a positive charge in the transmembrane region, e.g., enabling DAP12 recruitment (see Cao et al. (2008) Eur. J. Immunol. 38:2303-2315).

In one aspect, the present disclosure provides an antigen binding domain or protein comprising such, e.g. a monoclonal antibody or antibody fragment, that specifically binds and inhibits the activity of a human Siglec-10 polypeptide. The Siglec-10 polypeptide can be a membrane-bound Siglec-10 polypeptide expressed at the surface of a cell, e.g. a recombinant host cell expressing Siglec-10, a leukocyte, a lymphocyte, a B lymphocyte, a tumor-infiltrating lymphocyte, a circulating or tumor-infiltrating T or NK cell, an eosinophil and/or a dendritic cell.

In one embodiment, provided is an antigen binding domain or protein comprising such, e.g. a monoclonal antibody or antibody fragment, capable of blocking the interactions between a Siglec-10 polypeptide and a human target cell bearing a sialic acid ligand of Siglec-10 (e.g., a sialic acid-bearing human cell selected from MDA-MB-231 (breast adenocarcinoma), A375 (malignant melanoma), HCT 116 (epithelial; colon carcinoma) and WiDr (colorectal adenocarcinoma) cells).

In one embodiment, the antibody or antibody fragment potentiates the cytotoxic activity of a Siglec-10 expressing T or NK cell towards a human tumor cell.

The present invention arises, inter alia, from the discovery that human tumor cells can vary widely in their expression and/or decoration with sialic acid ligands of Siglec-10, of certain human tumor cell lines with particularly extensive cell surface expression of Siglec-10 ligands, and that antibodies to a single epitope on Siglec-10 (exemplified by monoclonal antibodies) can inhibit the interaction between Siglec-10 and the sialic acid on such cells. The resulting antibodies that inhibit interaction of Siglec-10 with sialic acids in these high-expressing cells can thus be used to treat a wide variety of tumors, moreover without any prior need to assess the nature or quantity of sialic acid decoration on the surface of tumor cells.

In one aspect, the present disclosure provides an antibody or an antibody fragment that binds to a Siglec-10 polypeptide expressed by a NK or T cell, and which reduces, neutralizes or reverses inhibition of NK or T cell cytotoxicity mediated by the Siglec-10 polypeptide.

In one aspect, the present disclosure provides a protein (e.g. an antibody) that is capable of binding to a Siglec-10 polypeptide expressed by a NK or T cell, and which protein potentiates the lytic activity of the NK or T cell against a sialylated human cancer cell. Optionally, the protein is a monoclonal antibody. Optionally, the antibody comprises two antigen binding domains (e.g. two VH-VL pairs) each capable of binding to a Siglec-10 polypeptide. Optionally, the antibody comprises one antigen binding domain (e.g. a VH-VL pair, an scFV) capable of binding to a Siglec-10 polypeptide (and optionally further a second antigen binding domain (e.g. a second VH-VL pair, a second scFV) capable of binding to a polypeptide other than Siglec-10).

In one embodiment, the antibody is capable of neutralizing the inhibitory activity of a Siglec-10 polypeptide on a leukocyte, by blocking the sialic acid ligand-induced inhibitory activity of such Siglec-10 polypeptide, without itself inducing substantial pro-apoptotic signalling by the Siglec-10 polypeptide (or, for example, apoptosis of the Siglec-10-expressing cell).

In one embodiment, the antibody is capable of blocking the interactions between a Siglec-10 polypeptide (e.g. as a soluble Siglec-10 polypeptide) and a human target cell bearing a sialic acid ligand of Siglec-10 (e.g., a sialic acid-bearing human cell selected from MDAMB-231, HCT116, WiDr and A375 cells lines).

In any of the embodiments herein, upon binding to Siglec-10 on a human lymphocyte, the monoclonal antibody has the ability to enhance or reconstitute lysis of a target human cell bearing a sialic acid ligand of Siglec-10 (e.g., a sialic acid-bearing human cell selected from MDA-MB-231, HCT116, WiDr and A375 cells lines.

In one aspect, the present disclosure provides a monoclonal antibody or an antigen binding fragment thereof (or a protein comprising such fragment) that specifically binds a human Siglec-10 polypeptide and is capable of inhibiting the interactions between a Siglec-10 polypeptide and a human target cell bearing a sialic acid ligand of Siglec-10 (e.g., a sialic acid-bearing human cell selected from MDA-MB-231, HCT116, WiDr and A375 cells lines).

Advantageously, the antibodies can be used as pure Siglec-10 blocking antibodies, e.g., they inhibit the activity of a membrane-bound Siglec-10 protein expressed at the surface of cells without inducing agonism at cell surface Siglec-10, without substantially binding Fcγ receptors and/or mediating Fcγ receptor-mediated crosslinking of Siglec-10, without inducing apoptosis of Siglec-10-expressing cells, and/or without substantially directing ADCC toward a Siglec-10-expressing cell. In one embodiment, the antibody substantially lacks binding, via its Fc domain, to a human CD16A, CD16B, CD32A, CD32B and/or CD64 polypeptide. In one embodiment, the antibody lacks an Fc domain or comprises a human Fc domain that is modified to reduce binding to a human FcγR (e.g. CD16A, CD16B, CD32A, CD32B and/or CD64).

In one embodiment, the antibodies retain at least a portion of an Fc domain and retain binding to human FcRn.

In some embodiments, the antibody is capable of neutralizing the inhibitory activity of a Siglec-10 polypeptide (e.g. by interfering with the Siglec-10 interaction with sialic acid ligands on a target cell) without a requirement for and/or dependence on the ability to cause the intracellular internalization of Siglec-10 (e.g. in an NK or T cell). Thus, in some embodiments, the antibody is capable of neutralizing the inhibitory activity of a Siglec-10 polypeptide without substantially inducing and/or increasing down-modulation and/or internalization of Siglec-10 at the surface of a cell (e.g. not causing the intracellular internalization of the antibody-Siglec-10 complex). In other embodiments, the antibody is capable of neutralizing the inhibitory activity of a Siglec-10 polypeptide and additionally is capable of inducing and/or increasing the down-modulation and/or internalization of Siglec-10 at the surface of a cell (e.g. causing the intracellular internalization of the antibody-Siglec-10 complex).

Optionally, in any embodiment herein, the ability of an antibody to neutralize the inhibitory activity of Siglec-10 is independent of the ability of the antibody to induce or increase down-modulation and/or internalization of Siglec-10 at the surface of a cell. In one embodiment, the antibody is capable of neutralizing the inhibitory activity of a Siglec-10 polypeptide (a neutralizing antibody), notably by blocking the ligand-induced inhibitory activity of such Siglec-10 polypeptide, and notably without substantially inducing and/or increasing intracellular signalling by the Siglec-10 polypeptide, e.g. without agonist activity at Siglec-10 expressed by NK cells, B cells, T cells and/or in other leukocytes.

In one embodiment, the antibody furthermore does not substantially bind to a CD33-related Siglec polypeptide other than Siglec-10. In one embodiment, the antibody furthermore does not substantially bind to a human Siglec-5 polypeptide, e.g. the antibody does not bind a cell made to express a Siglec-5 polypeptide, and the antibody does not bind to a recombinant soluble Siglec-5-Fc fusion protein. In one embodiment, the antibody furthermore does not substantially bind to a human Siglec-7 polypeptide, e.g. the antibody does not bind a cell made to express a Siglec-7 polypeptide, and the antibody does not bind to a recombinant soluble Siglec-7-Fc fusion protein. In one embodiment, the antibody furthermore does not substantially bind to a human Siglec-11 polypeptide, e.g. the antibody does not bind a cell made to express a Siglec-11 polypeptide, and the antibody does not bind to a recombinant soluble Siglec-11-Fc fusion protein. In one embodiment, the antibody does not substantially bind to a human Siglec-3, -5, -6, -8, -7, -9, -11 and/or -12 protein.

In one embodiment, the antibody does not substantially bind to a human Siglec-16 protein, e.g. the antibody does not bind a cell made to express a Siglec-16 polypeptide, and the antibody does not bind to a recombinant soluble Siglec-16-Fc fusion protein.

In one embodiment, an antibody is characterized by an $EC_{50}$ for binding to a cell made to express a human Siglec-10 polypeptide, as determined by flow cytometry, that is at least 1-log lower, optionally at least 10-log lower, optionally at least 100-log lower, than the $EC_{50}$ for binding to a cell made to express a human Siglec-5 polypeptide. Optionally, the cells made to express the Siglec-10 or Siglec-5 polypeptide are CHO cells. Optionally, a cell made to express a Siglec-10 polypeptide does not express Siglec-5 polypeptide and/or other human CD33-related Siglec polypeptides. The cells expressing at their surface Siglec-10 or Siglec-5 can be characterized as expressing the respective Siglec polypeptides at comparable levels of expression.

In one embodiment, an antibody is characterized by an $EC_{50}$ for binding to a cell made to express a human Siglec-10 polypeptide, as determined by flow cytometry, that is at least 1-log lower, optionally at least 10-log lower, optionally at least 100-log lower, than the $EC_{50}$ for binding to a cell made to express a human Siglec-7 polypeptide. Optionally, the cells made to express the Siglec-10 or Siglec-7 polypeptide are CHO cells. Optionally, a cell made to express a Siglec-10 polypeptide does not express Siglec-7 polypeptide and/or other human CD33-related Siglec polypeptides. The cells expressing at their surface Siglec-10 or Siglec-7 can be characterized as expressing the respective Siglec polypeptides at comparable levels of expression.

In one embodiment, an antibody is characterized by an $EC_{50}$ for binding to a cell made to express a human Siglec-10 polypeptide, as determined by flow cytometry, that is at least 1-log lower, optionally at least 10-log lower, optionally at least 100-log lower, than the $EC_{50}$ for binding to a cell made to express a human Siglec-11 polypeptide. Optionally, the cells made to express a Siglec-10 or Siglec-11 polypeptide are CHO cells. Optionally, a cell made to express a Siglec-10 polypeptide does not express Siglec-11 polypeptide and/or other human CD33-related Siglec polypeptides. The cells expressing at their surface Siglec-10 or Siglec-11 can be characterized as expressing the respective Siglec polypeptides at comparable levels of expression.

In any of the embodiments herein, tan anti-Siglec-10 antibody can be characterized by binding to human Siglec-10 polypeptides expressed on the surface of a cell (e.g., an NK cell, a T cell (e.g. a CD8 T cell), a cell made to express Siglec-10 (e.g., a recombinant CHO host cell made to express Siglec-10 at its surface, as exemplified in Example 2), and optionally further wherein the antibody binds with high affinity as determined by flow cytometry. For example, an antibody can be characterized by an $EC_{50}$, as determined by flow cytometry (e.g. according to the methods of Example 2, herein), of no more than 2 μg/ml, optionally no more than 1 μg/ml, optionally no more than 0.5 μg/ml, optionally no more than 0.2 μg/ml, or optionally no more than 0.1 μg/ml, optionally between 0.01 and 1 μg/ml, optionally between 0.05 and 0.5 μg/ml or optionally about 0.1 μg/ml, for binding to cells that express at their surface a Siglec-10 polypeptide (e.g. CHO cells that express Siglec-10, exemplified in Example 2 herein).

In any of the embodiments herein, an anti-Siglec-10 antibody can be characterized by binding to a Siglec-10 expressing cell with a binding affinity (e.g. as determined by flow cytometry) that is higher than the binding affinity of a human CD24 protein (e.g. as an Fc fusion protein) for a Siglec-10 expressing cell. In one embodiment, an antibody is characterized by an $EC_{50}$ for binding to a cell made to express a human Siglec-10 polypeptide, as determined by flow cytometry, that is at least 0.1-log lower, 0.5-log lower or 1-log lower, than the $EC_{50}$ for binding of a human CD24 protein (e.g. a soluble CD24-Fc protein) to a cell made to express a human Siglec-10 polypeptide. Optionally, the cells made to express a Siglec-10 polypeptide is a Chinese Hamster Ovary (CHO) cell.

In any of the embodiments herein, the anti-Siglec-10 antibodies can be characterized by binding to a Siglec-10 expressing cell with a binding affinity (e.g. as determined by flow cytometry) that is higher than the binding affinity of a human CD52 protein (e.g. as an Fc fusion protein) for a Siglec-10 expressing cell. In one embodiment, an antibody is characterized by an $EC_{50}$ for binding to a cell made to express a human Siglec-10 polypeptide, as determined by flow cytometry, that is at least 0.1-log lower, 0.5-log lower or 1-log lower, than the $EC_{50}$ for binding of a human CD52 protein (e.g. a soluble CD52-Fc protein) to a cell made to express a human Siglec-10 polypeptide. Optionally, the cells made to express a Siglec-10 polypeptide is a Chinese Hamster Ovary (CHO) cell.

In any embodiment herein, the antibodies can be characterized by the ability to block or inhibit the interaction between Siglec-10 (e.g. a human Siglec-10 protein expressed at the surface of a cell, a recombinant soluble human Siglec-10-Fc fusion protein) and a sialoside-containing ligand(s) thereof (e.g., a natural ligand) and/or block the Siglec-10 activity (transmission of an inhibitory signal) induced by a sialoside-containing ligand thereof.

In any embodiment herein, the antibodies block the interaction between a Siglec-10 polypeptide (e.g. a Siglec-10 polypeptide expressed at the surface of a cells and/or a soluble Siglec-10 polypeptide) and a cell bearing sialic acid ligands of Siglec-10 at its surface, e.g. a human tumor cell. In one embodiment, the cancer cell is a cell from a B cell lymphoma, renal cell carcinoma, small cell and non-small cell lung carcinoma, nasopharyngeal carcinoma, hepatocellular carcinoma and breast cancer.

In any embodiment herein, the antibodies inhibit the intracellular signalling activity of a Siglec-10 polypeptide mediated by the ITAM-signalling motif, e.g. the Siglec-10 intracellular signalling induced by the interaction with a natural ligand such as a sialic acid expressed at the surface of a human tumor cell.

In one embodiment, the antibody increases NK cell, B cell and/or T (or more generally leukocyte) cell activation. In one embodiment, neutralization of an inhibitory activity of Siglec-10 is assessed by increase in a marker of cellular activation, optionally a marker of cytotoxicity/cytotoxic potential, e.g. CD107 and/or CD137 expression (mobilization). The Siglec-10 may comprise an amino acid sequence of SEQ ID NO: 1.

In one aspect of any of the embodiments herein, the antibody is a tetrameric (e.g., full length, F(ab)'2 fragment) antibody, is capable of binding an epitope present on the extra-cellular domain of Siglec-10 polypeptides expressed by a cell in bivalent fashion (the antibody has two antigen binding domains, each capable of binding to a Siglec-10 polypeptide) and lacks agonist activity at such Siglec-10. In another aspect of any of the embodiments herein, the antibody binds to a Siglec-10 polypeptide expressed by a cell in monovalent manner and lacks agonist activity at such Siglec-10. In one embodiment, the antibody that binds Siglec-10 in monovalent manner is a Fab fragment. In any of the embodiments herein, the antibody binds to Siglec-10 in monovalent or bivalent manner is free of agonist activity at Siglec-10. For therapeutic use, an antibody is preferably a non-depleting antibody. Optionally the antibody comprises and Fc domain capable of be bound by the human neonatal Fc receptor (FcRn) but which substantially lacks binding, via its Fc domain, to a human FcγR (e.g. CD16A, CD16B, CD32A, CD32B and/or CD64).

In any of the embodiments herein, upon binding to Siglec-10 on a human lymphocyte, the monoclonal antibody has the ability to enhance or reconstitute lysis of a target human cell bearing a sialic acid ligand of Siglec-10 (e.g., a sialic acid-bearing human tumor cell, a cell selected from the MDA-MB-231 and A375 cells) on the target cell surface, and/or has the ability to increase lymphocyte activation (e.g., as determined by an increase in CD107 and/or CD137 expression on a lymphocyte), when said target cell comes into contact with said lymphocyte (e.g. an effector lymphocyte, an NK or a T cell).

In one aspect, provided is an antibody that is a monoclonal antibody or a fragment thereof characterized by:
 a) specifically binding to Siglec-10, and when bound to the Siglec-10 on a human leukocyte, neutralizing Siglec-10-mediated inhibition of lymphocyte activation or cytotoxicity when the human leukocyte is brought into contact with a target cell bearing a ligand of Siglec-10 on the target cell surface (e.g., a sialic acid-bearing human tumor cell, a cell selected from MDA-MB-231, HCT116, WiDr and A375 cells); and
 b) not substantially binding (e.g. via an Fc domain of the antibody) to a human Fcγ receptor (e.g. CD16). In one embodiment, the antibody is a full length antibody comprising a human Fc domain. In one embodiment, the leukocyte is an NK cell. In one embodiment, the lymphocyte is a T cell. In one embodiment, the lymphocyte is a B cell. In one embodiment, the ligand of Siglec-10 is a sialic acid or molecule comprising a sialic acid (e.g. a sialic acid-bearing human cell selected from MDA-MB-231, HCT116 and A375 cells lines)).

Optionally, the neutralization of Siglec-10-mediated inhibition of lymphocyte activation or cytotoxicity is independent of the ability of the antibody to induce or increase down-modulation and/or internalization of Siglec-10 at the surface of a cell. Optionally, the antibody is further characterized by (c): not substantially inducing or increasing down-modulation and/or internalization of Siglec-10 at the surface of a cell (e.g. not causing the intracellular internalization of the antibody-Siglec-10 complex).

In one aspect, provided is an antibody that is a monoclonal antibody or a fragment thereof characterized by being capable of:
 a) specifically binding to Siglec-10 polypeptide on the surface of a lymphocyte;
 b) inhibiting the interactions between a Siglec-10 polypeptide and a human target cell bearing a sialic acid ligand of Siglec-10 (e.g., a sialic acid-bearing human cell selected from MDA-MB-231, HCT116 and A375 cells); and
 c) not substantially binding (e.g. via an Fc domain of the antibody) to a human Fcγreceptor (e.g. CD16). In one embodiment, the antibody is a full length antibody comprising a human Fc domain. In one embodiment, the lymphocyte is an NK cell. In one embodiment, the lymphocyte is a T cell. In one embodiment, the human target cell is a tumor cell.

In one aspect, provided is an antibody that is a monoclonal antibody or a fragment thereof characterized by:
 a) specifically binding to Siglec-10, and when bound to Siglec-10 on a human lymphocyte, causing (e.g. increasing the ability of) said lymphocyte to lyse a target human cell bearing a ligand of Siglec-10 on the target cell surface, when said target cell is brought into contact with said lymphocyte; and b) not substantially binding (e.g. via an Fc domain of the antibody) to a human Fcγ receptor (e.g. CD16). In one embodiment, the antibody is a full length antibody comprising a human Fc domain. In one embodiment, the lymphocyte is an NK cell. In one embodiment, the lymphocyte is a T cell.

Optionally, the neutralization of Siglec-10-mediated inhibition of lymphocyte activation or cytotoxicity is independent of the ability of the antibody to induce or increase down-modulation and/or internalization of Siglec-10 at the surface of a cell. Optionally, the antibody is further characterized by (c): not substantially inducing or increasing down-modulation and/or internalization of Siglec-10 at the surface of a cell (e.g. not causing the intracellular internalization of the antibody-Siglec-10 complex).

In any of the embodiments herein, the antibody blocks the inhibitory signalling by Siglec-10 triggered by a sialoside ligand of the Siglec-10, wherein the antibody binds Siglec-10 without causing signalling by Siglec-10.

In one aspect of any of the embodiments herein, the antibody is capable of blocking binding of Siglec-10 to a sialoside ligand of Siglec-10.

In any of the embodiments herein, the sialic acid ligand of Siglec-10 is a natural ligand, e.g. a naturally occurring sialic acid ligand (a ligand comprising a sialic acid). Sialic acids, a family of nine-carbon acidic monosaccharides, are typically found to be terminating branches of N-glycans, O-glycans, and glycolipids. Siglecs are believed to recognize many aspects of the sialic acid molecule, like the acid sialic linkage from the 2-position, the arrangements of sialic acids and their way of presentation. In any of the embodiments herein, the ligand of a Siglec comprises a 5-N-acetylneuraminic acid (Neu5Ac) derivative, and can optionally comprise other sialic acid derivatives, like 5-N-glycolylneuraminic acid (Neu5Gc) derivatives. In one embodiment, the ligand of Siglec-10 is a sialic acid present on a glycoprotein (e.g. a mucin) or a glycolipid. In one embodiment, the ligand of Siglec-10 comprises a sialic acid presented on a human tumor cell, e.g. a MDA-MB-231 cell, a HCT116 cell, a WiDr cell or an A375 cell.

In any of the embodiments herein, upon binding to a Siglec on a human lymphocyte (e.g. NK cell), the monoclonal antibody has the ability to reconstitute lysis of a target human cell bearing a sialic acid ligand of the Siglec on the target cell surface, when said target cell comes into contact with said lymphocyte.

In any of the embodiments herein, the antibody has a $K_D$ of less than $10^{-8}$ M, preferably less than $10^{-9}$ M for binding to each of the human Siglec-10 polypeptide.

Also provided is a human or humanized antibody or antibody fragment, or a derivative thereof, which has any of the foregoing properties, alone or in any suitable combination.

In one embodiment, the antibody is a monoclonal antibody. In one embodiment, the antibody is an IgG1, IgG2, IgG3, or IgG4 antibody. For example, the antibody may be an antibody comprising an Fc domain of human IgG4 isotype or an antibody comprising an Fc domain of any human IgG isotype (e.g. IgG1, IgG2, IgG3, or IgG4) modified to reduce binding between the Fc domain and an Fcγ receptor (e.g. CD16). In one embodiment, an antibody that binds to Siglec-10 expressed by a leukocyte (e.g. NK or T cell) does not lead, directly or indirectly, to the depletion of such cells expressing Siglec-10 (e.g. do not lead to a 5%, 10%, 20%, 30% or greater elimination or decrease in number of Siglec10+ leukocytes). Preferably, the antigen-binding compound does not comprise an Fc domain capable of inducing antibody mediated cellular cytotoxicity (ADCC) and/or complement-dependent cytotoxicity (CDC); optionally the antigen-binding compound does not comprise an Fc domain capable of substantially binding to a FcγRIII (CD16) polypeptide, or comprises an Fc domain not capable of substantially binding to a FcγRIII (CD16) polypeptide; preferably the antigen-binding compound lacks an Fc domain (e.g. lacks a CH2 and/or CH3 domain) or comprises an Fc domain of IgG2 or IgG4 isotype, optionally an Fc domain of IgG4 isotype comprising a stabilizing mutation to decrease formation of half-antibodies such as a S241 P mutation; optionally the antigen-binding compound consists of or comprises a Fab, Fab', Fab'-SH, F (ab') 2, Fv, a diabody, single-chain antibody fragment, or a multispecific antibody comprising multiple different antibody fragments. Preferably the antigen-binding compound is not linked to a toxic moiety. Preferably the antibody does not act as an agonist of the Siglec-10 polypeptides, e.g. the antibody is optionally not capable of causing sufficient cross-linking, in vivo, of Siglec-10 polypeptide on an NK cell so as to cause signalling by Siglec-10.

In one aspect of any of the embodiments herein, binding of an antibody or antibody fragment to a Siglec-10 polypeptide can be specified as being cellular Siglec-10 polypeptide, where the Siglec-10 polypeptide is expressed at the surface of a cell, for example a native or modified cellular Siglec-10 polypeptide, a Siglec-10 polypeptide expressed by a recombinant host cell, a Siglec-10 polypeptide expressed by a leukocyte, a B cell, an NK cell, a CD8 T cell, etc.

In one aspect of any of the embodiments herein, provided is an antigen-binding compound that binds the same epitope and/or competes for binding to a Siglec-10 polypeptide with monoclonal antibodies S10-A, S10-B or S10-C (e.g., that competes for binding to a Siglec-10 polypeptide expressed by a cell with an antibody having the heavy and light chain CDRs or variable regions of any of S10-A, S10-B or S10-C). In one embodiment, provided is antigen-binding compound binds the same epitope and/or competes for binding to a Siglec10 polypeptide with an antibody selected from the group consisting of:

(a) an antibody having respectively a VH and VL region of SEQ ID NOS: 12 and 13 (S10-A);

(b) an antibody having respectively a VH and VL region of SEQ ID NOS: 20 and 21 (S10-B); and (c) an antibody having respectively a VH and VL region of SEQ ID NOS: 28 and 29 (S10-C).

In one aspect of any of the embodiments herein, the antibody may have a heavy and/or light chain having one, two or three CDRs of the respective heavy and/or light chain of an antibody selected from the group consisting of antibody S10-A, S10-B and S10-C.

In one aspect of any of the embodiments herein, provided is an antigen-binding compound (e.g. an antibody) comprising (i) an immunoglobulin heavy chain variable domain comprising the CDR 1, 2 and 3 of the heavy chain variable region of SEQ ID NO: 12 and (ii) an immunoglobulin light chain variable domain comprising the CDR 1, 2 and 3 of the light chain variable region of SEQ ID NO: 13.

In one aspect of any of the embodiments herein, provided is an antigen-binding compound (e.g. an antibody) comprising (i) an immunoglobulin heavy chain variable domain comprising the CDR 1, 2 and 3 of the heavy chain variable region of SEQ ID NO: 20 and (ii) an immunoglobulin light chain variable domain comprising the CDR 1, 2 and 3 of the light chain variable region of SEQ ID NO: 21.

In one aspect of any of the embodiments herein, provided is an antigen-binding compound (e.g. an antibody) comprising (i) an immunoglobulin heavy chain variable domain comprising the CDR 1, 2 and 3 of the heavy chain variable region of SEQ ID NO: 28 and (ii) an immunoglobulin light chain variable domain comprising the CDR 1, 2 and 3 of the light chain variable region of SEQ ID NO: 29.

Also provided is a nucleic acid encoding the human or humanized antibody or antibody fragment (e.g. a heavy and/or light chain thereof) having any of the foregoing properties, a vector comprising such a nucleic acid, a cell comprising such a vector, and a method of producing a human anti-Siglec-10 antibody, comprising culturing such a cell under conditions suitable for expression of the anti-Siglec-10 antibody. The disclosure also relates to compositions, such as pharmaceutically acceptable compositions and kits, comprising such proteins, nucleic acids, vectors, and/or cells and typically one or more additional ingredients that can be active ingredients or inactive ingredients that promote formulation, delivery, stability, or other characteristics of the composition (e.g., various carriers). The disclosure further relates various new and useful methods making and using such antibodies, nucleic acids, vectors, cells, organisms, and/or compositions, such as in the modulation of Siglec-10-mediated biological activities, for example in the treatment of diseases related thereto, notably cancers and infectious disease.

Also provided are methods of producing an antibody which binds Siglec-10 and which neutralizes the inhibitory activity Siglec-10, said method comprising the steps of:
  (a) providing a plurality of antibodies that bind a Siglec-10 polypeptide,
  (b) selecting an antibody (e.g. among those of step of (a)) that neutralizes the inhibitory activity Siglec-10, and
  (c) optionally, selecting an antibody (e.g. among those of step (b)) that does not substantially induce or increase down-modulation and/or internalization of Siglec-10 at the surface of a cell. Optionally, the step (b) comprises selecting an antibody that blocks the interaction between a Siglec-10 polypeptide and a respective sialic acid ligand thereof (e.g., a human tumor cell, e.g. MDA-MB-231 cells, HCT116 cells, WiDr cells and/or A375 cells).

Also provided are methods of producing an antibody which binds Siglec-10 and which neutralizes the inhibitory activity Siglec-10, said method comprising the steps of:
  (a) providing a plurality of antibodies that bind a Siglec-10 polypeptide,
  (b) selecting an antibody (e.g. among those of step of (a)) that does not substantially cause down-modulation and/or internalization of Siglec-10 at the surface of a cell, and
  (c) selecting an antibody (e.g. among those of step (b)) that does not substantially induce or increase down-modulation and/or internalization of Siglec-10 at the surface of a cell.

It will be appreciated that steps (a), (b) and (c) in any of the above methods can be carried out in any desired order.

In one embodiment, determining whether an antibody neutralizes the inhibitory activity of Siglec-10 comprises assessing whether the antibody blocks the interaction between a Siglec-10 polypeptide and a respective sialic acid ligand thereof.

In one embodiment, determining whether an antibody neutralizes the inhibitory activity of Siglec-10 comprises assessing whether the antibody causes an increase in a marker of activation, optionally cytotoxicity, optionally an increase in expression of CD107 and/or CD137, when lymphocytes expressing the Siglec-10 are brought into contact with target cells (e.g. that express ligands of the Siglec-10). An increase in a marker of activation or cytotoxicity (e.g. an increase in expression of CD107 and/or CD137) indicates that the antibody is capable of neutralizing the inhibitory activity of Siglec-10.

In one embodiment, the antibodies are monoclonal antibodies.

In one embodiment, providing a plurality of antibodies in step (a) comprises immunizing a non-human mammal with an immunogen comprising a CD33-related Siglec polypeptide (e.g., Siglec-10), and preparing antibodies from said immunized mammal, wherein said antibodies bind Siglec-10. The term "preparing antibodies from said immunized animal," as used herein, includes obtaining B-cells from an immunized animal and using those B cells to produce a hybridoma that expresses antibodies, as well as obtaining antibodies directly from the serum of an immunized animal. In one embodiment, providing a plurality of antibodies in step (a) comprises producing a library of antibodies, e.g. by phage display.

Also provided is an in vitro method for modulating the activity of Siglec-10-expressing leukocytes, optionally NK cells, B cells, and/or T cells, the method comprising bringing leukocytes expressing at their surface Siglec-10 into contact with an antibody that neutralizes the inhibitory activity of Siglec-10.

Also provided is a method of potentiating and/or modulating the activity of leukocytes (e.g., NK cells, B cells, T cells) activity in a subject in need thereof, which method comprises administering to the subject an effective amount of any of the foregoing compositions. In one embodiment, the subject is a patient suffering from a cancer or an infectious disease. For example, the patient may be suffering from a hematopoietic cancer, e.g., acute myeloid leukaemia, chronic myeloid leukaemia, multiple myeloma, or non-Hodgkin's lymphoma. Alternatively, the patient may be suffering from a solid tumor, e.g. a carcinoma, colorectal cancer, renal cancer, ovarian cancer, lung cancer, breast cancer or malignant melanoma.

In one embodiment, provided is a method for treating an individual having a cancer, optionally a carcinoma, optionally a breast carcinoma, a colon carcinoma or a malignant melanoma, the method comprising administering to the individual (e.g. an individual having a cancer) a therapeutically active amount of any of the anti-Siglec-10 antigen binding compounds described herein. In one embodiment, the anti-Siglec-10 antigen binding compound (e.g. antibody) is administered to an individual in combination with an antibody that neutralizes the inhibitory activity of human PD-1, optionally an anti-PD-1 antibody, optionally an anti-PD-L1 antibody. In one embodiment, the anti-Siglec-10 antigen binding compound (e.g. antibody) is administered to an individual having a cancer and who has a poor response, or prognostic for response, to treatment with an agent that neutralizes the inhibitory activity of human PD-1.

These aspects are more fully described in, and additional aspects, features, and advantages will be apparent from, the description of the invention provided herein.

DETAILED DESCRIPTION OF THE DRAWINGS

FIG. 1 shows binding of three antibodies S10A, S10-B and S10-C to cell lines transfected with one or another Siglec, illustrated by Siglec-7 and Siglec-10, as assessed by flow cytometry on CHO cells transfected with human Siglec-10. The antibodies bound human Siglec-10 transfectants and not the control Siglec-7 transfectants.

Figure 2A:
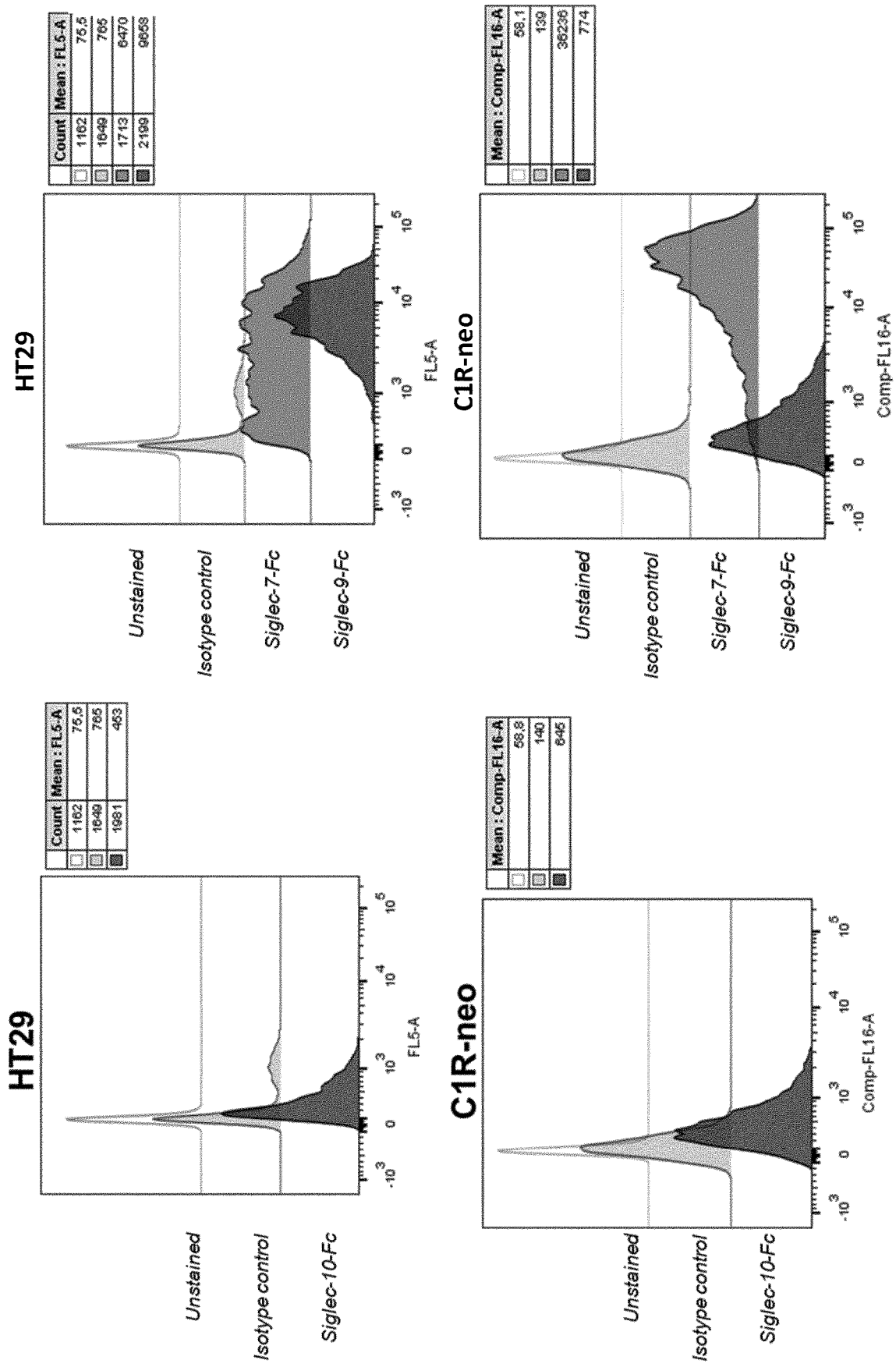
Figure 2B:
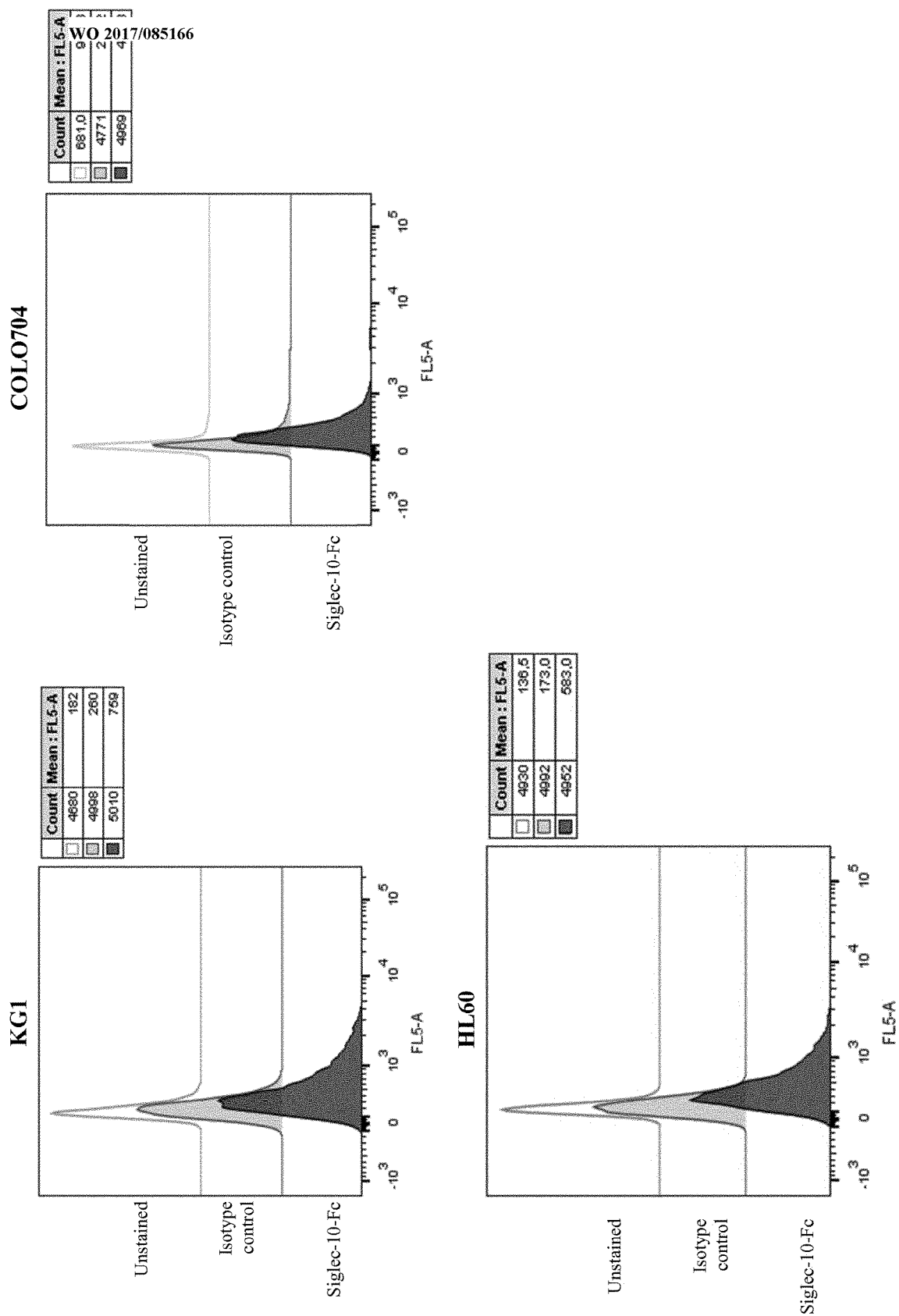

FIG. 2A shows binding of soluble Siglec-Fc polypeptides (Siglec-7-Fc, Siglec-9-Fc and Siglec-10-Fc) to HT29 tumor cell which has been reported to bear sialic acid ligands of Siglec-9, as assessed by flow cytometry. While soluble Siglec-9 and Siglec-7 bound to HT29 cells, Siglec-10 Fc proteins show no or only minimal level of binding. FIG. 2B shows binding of soluble Siglec-10-Fc polypeptide to KG1, COLO704 and HL60 tumor cell lines, as assessed by flow cytometry. Siglec-10 Fc proteins show no or only minimal level of binding.

Figure 3:
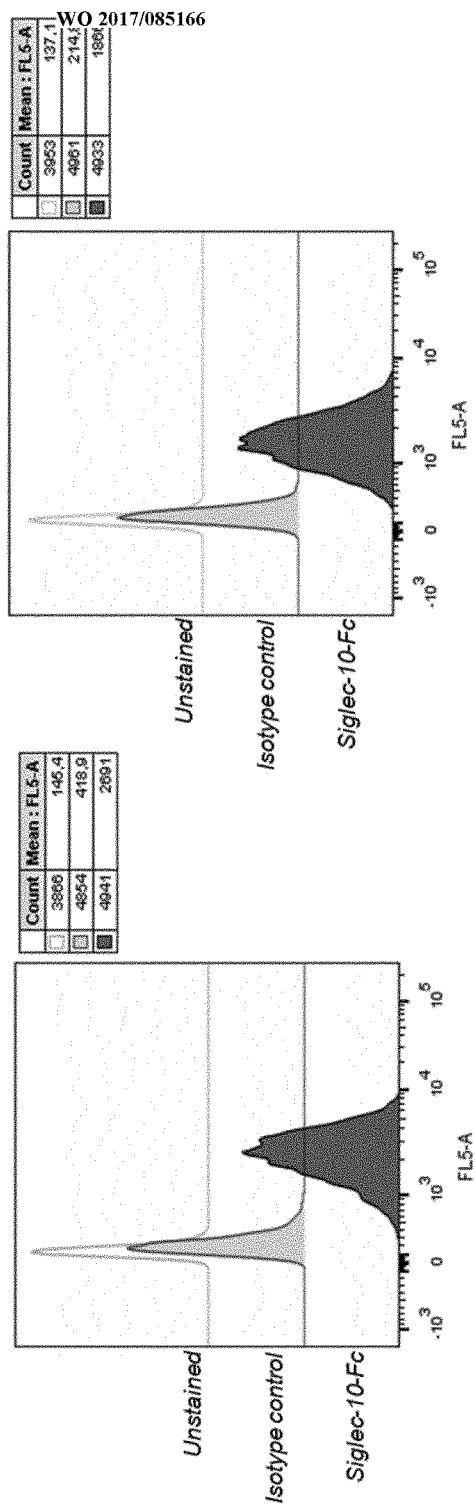
Figure 3:
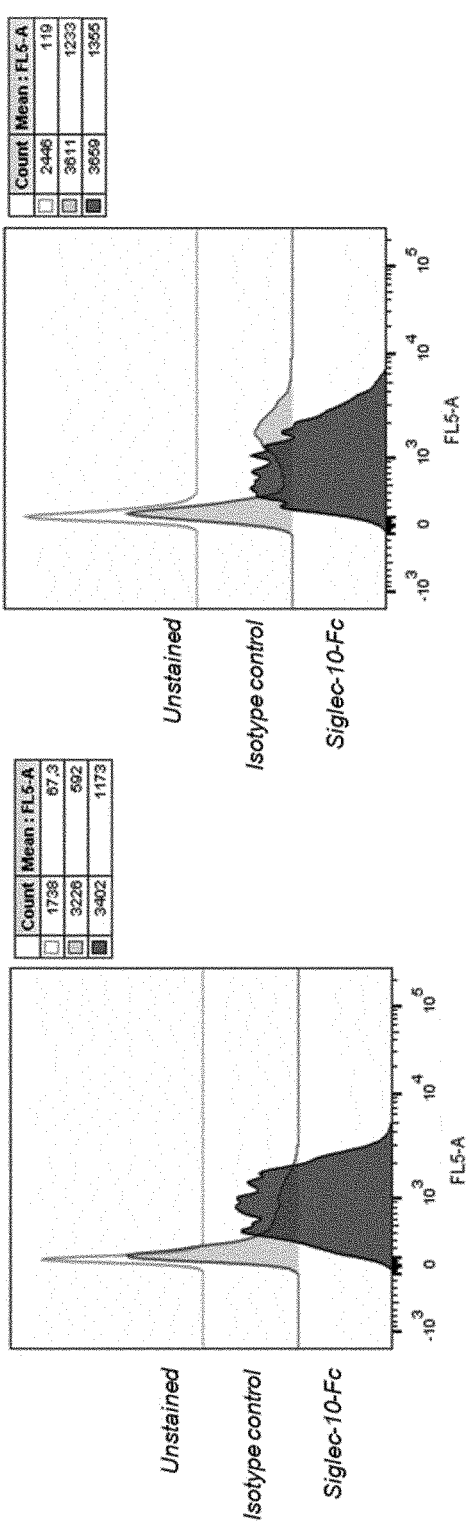

FIG. 3 shows binding of soluble Siglec-10-Fc polypeptide to human MDA-MB-231 (breast adenocarcinoma), A375 (malignant melanoma), HCT 116 (epithelial; colon carcinoma) and WiDr (colorectal adenocarcinoma) tumor cell lines, as assessed by flow cytometry. Siglec-10 Fc proteins show strong binding to these cells.

Figure 4:
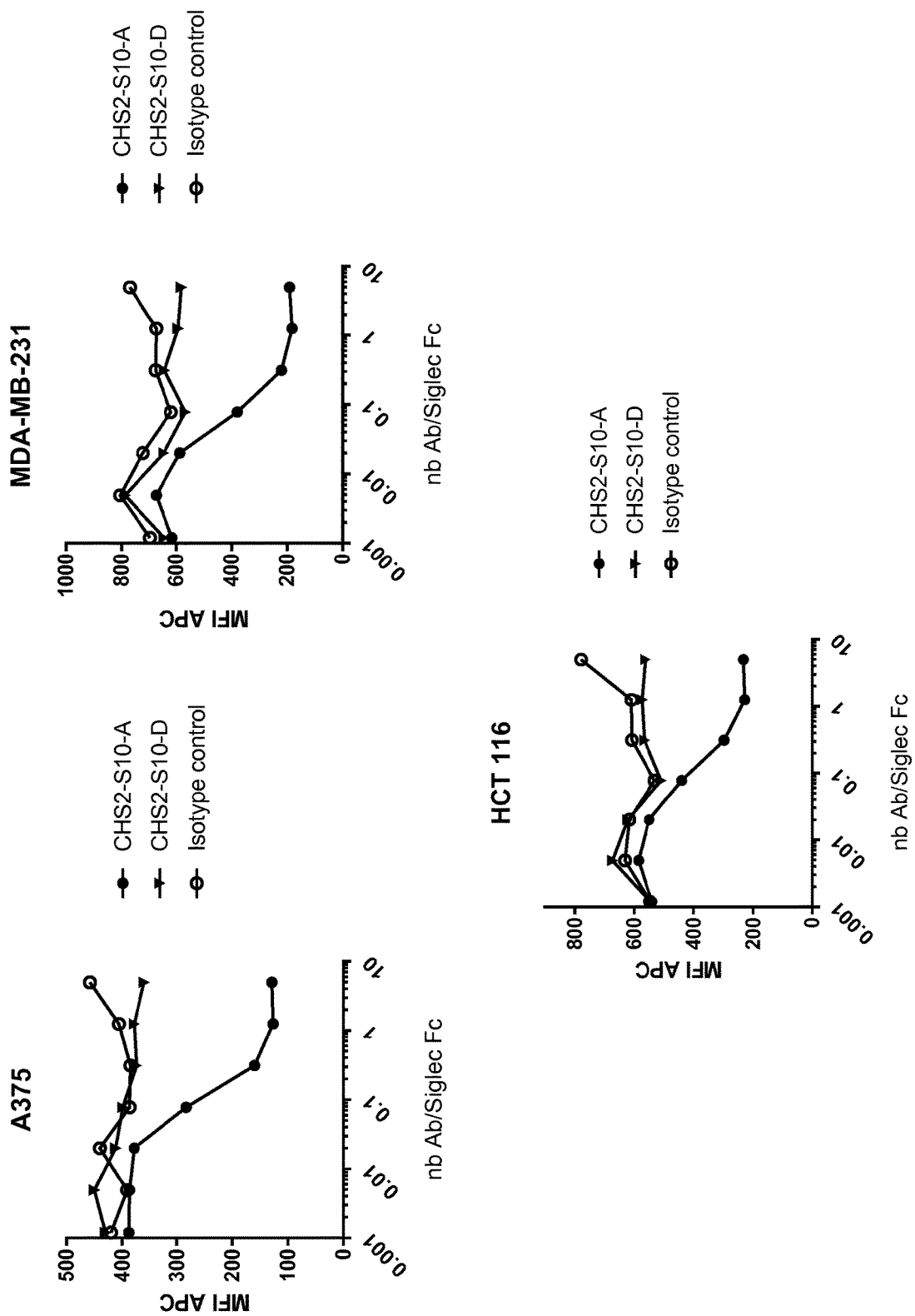

FIG. 4 shows blocking activity of the anti-Siglec-10 antibodies as evaluated by cytometry. Siglec-10 Fc (Mouse IgFc) at 10 µg/ml was incubated with anti-Siglec-10 antibodies and the Siglec-10Fc/antibody complexes were incubated with tumor cell lines and then washed. Selected antibodies blocked the binding of Siglec-10 Fc to the tumor cell lines.

DETAILED DESCRIPTION

Definitions

As used in the specification, "a" or "an" may mean one or more. As used in the claim(s), when used in conjunction with the word "comprising", the words "a" or "an" may mean one or more than one. As used herein "another" may mean at least a second or more.

Where "comprising" is used, this can optionally be replaced by "consisting essentially of" or by "consisting of".

The amino acid sequence of human Siglec-10 is shown in Genbank accession number NP_149121 (the entire disclosure of which is incorporated herein by reference), as well as in SEQ ID NO: 1 (see also Table 2). The nucleic acid sequence encoding Siglec-10 is shown in Genbank accession number NM_033130.4 and in SEQ ID NO: 2. Amino acid sequences of Siglec-3, -5, -6, -7, -8, -9, -11, -12 and 16 are shown in Table 2.

As used herein, "neutralize the inhibitory activity of Siglec-10", or "neutralize Siglec10-mediated inhibition of cytotoxicity" or the like refers to a process in which Siglec-10 is inhibited in its capacity to negatively affect intracellular processes leading to lymphocyte responses such as cytokine release and cytotoxic responses. This can be measured for example in a standard NK- or T-cell based cytotoxicity assay, in which the capacity of a therapeutic compound to enhance the activation of Siglec-10 positive lymphocytes in the presence of sialic-acid ligand positive target cells is measured. In one embodiment, an antibody preparation causes at least a 10% augmentation in the activation or cytotoxicity of a Siglec-10-restricted lymphocyte, optionally at least a 40% or 50% augmentation in lymphocyte activation or cytotoxicity, or optionally at least a 70% augmentation in activation or cytotoxicity. In one embodiment, an antibody preparation causes at least a 10% augmentation in cytokine release by a Siglec-10 restricted lymphocyte, optionally at least a 40% or 50% augmentation in cytokine release, or optionally at least a 70% augmentation in cytokine release, and referring to the cytotoxicity assays described herein. In one embodiment, an antibody preparation causes at least a 10% augmentation in cell surface expression of a marker of cytotoxicity (e.g. CD107 and/or CD137) by a Siglec-10-restricted lymphocyte, optionally at least a 40% or 50% augmentation, or optionally at least a 70% augmentation in cell surface expression of a marker of cytotoxicity (e.g. CD107 and/or CD137).

The ability of an anti-Siglec-10 antibody to "block" the binding of a Siglec-10 molecule to a sialic acid ligand (e.g. as may be present at the surface of a cell) means that the antibody, in an assay using soluble or cell-surface associated Siglec-10 and sialic acid molecules, can detectably reduce the binding of a Siglec-10 molecule to a sialic acid molecule (or to cell bearing such sialic acid molecule) in a dose-dependent fashion, where the Siglec-10 molecule detectably binds to the sialic acid molecule or to cell bearing such sialic acid molecule in the absence of the antibody. Optionally, an antibody may cause a reduction of at least a 40% or 50%, or optionally at least a 70%, in binding of a Siglec-10 molecule to a sialic acid molecule or to cell bearing such sialic acid molecule.

The term "internalization", used interchangeably with "intracellular internalization", refers to the molecular, biochemical and cellular events associated with the process of translocating a molecule from the extracellular surface of a cell to the intracellular surface of a cell. The processes responsible for intracellular internalization of molecules are well-known and can involve, inter alia, the internalization of extracellular molecules (such as hormones, antibodies, and small organic molecules); membrane-associated molecules (such as cell-surface receptors); and complexes of membrane-associated molecules bound to extracellular molecules (for example, a ligand bound to a transmembrane receptor or an antibody bound to a membrane-associated molecule). Thus, "inducing and/or increasing internalization" comprises events wherein intracellular internalization is initiated and/or the rate and/or extent of intracellular internalization is increased.

Whenever within this whole specification "treatment of cancer" or the like is mentioned with reference to anti-Siglec-10 binding agent (e.g. antibody), there is meant: (a) method of treatment of cancer, said method comprising the step of administering (for at least one treatment) an anti-Siglec-10 binding agent, (preferably in a pharmaceutically acceptable carrier material) to an individual, a mammal, especially a human, in need of such treatment, in a dose that allows for the treatment of cancer, (a therapeutically effective amount), preferably in a dose (amount) as specified herein; (b) the use of an anti-Siglec-10 binding agent for the treatment of cancer, or an anti-Siglec-10 binding agent, for use in said treatment (especially in a human); (c) the use of an anti-Siglec-10 binding agent for the manufacture of a pharmaceutical preparation for the treatment of cancer, a method of using an anti-Siglec-10 binding agent for the manufacture of a pharmaceutical preparation for the treatment of cancer, comprising admixing an anti-Siglec-10 binding agent with a pharmaceutically acceptable carrier, or a pharmaceutical preparation comprising an effective dose of an anti-Siglec-10 binding agent that is appropriate for the treatment of cancer; or (d) any combination of a), b), and c), in accordance with the subject matter allowable for patenting in a country where this application is filed.

As used herein, the term "antigen binding domain" refers to a domain comprising a three-dimensional structure capable of immunospecifically binding to an epitope. Thus, in one embodiment, said domain can comprise a hypervariable region, optionally a VH and/or VL domain of an antibody chain, optionally at least a VH domain. In another embodiment, the binding domain may comprise at least one complementarity determining region (CDR) of an antibody chain. In another embodiment, the binding domain may comprise a polypeptide domain from a non-immunoglobulin scaffold.

The term "antibody," as used herein, refers to polyclonal and monoclonal antibodies. Depending on the type of constant domain in the heavy chains, antibodies are assigned to one of five major classes: IgA, IgD, IgE, IgG, and IgM. Several of these are further divided into subclasses or isotypes, such as IgG1, IgG2, IgG3, IgG4, and the like. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids that is primarily responsible for antigen recognition. The terms variable light chain ($V_L$) and variable heavy chain ($V_H$) refer to these light and heavy chains respectively. The heavy-chain constant domains that correspond to the different classes of immunoglobulins are termed "alpha," "delta," "epsilon," "gamma" and "mu," respectively. The subunit structures and three-dimensional configurations of different classes of immunoglobulins are well known. IgG are the exemplary classes of antibodies employed herein because they are the most common antibodies in the physiological situation and because they are most easily made in a laboratory setting. Optionally the antibody is a monoclonal antibody. Particular examples of antibodies are humanized, chimeric, human, or otherwise-human-suitable antibodies. "Antibodies" also includes any fragment or derivative of any of the herein described antibodies.

The term "specifically binds to" means that an antibody can bind preferably in a competitive binding assay to the binding partner, e.g. Siglec-10, as assessed using either recombinant forms of the proteins, epitopes therein, or native proteins present on the surface of isolated target cells. Competitive binding assays and other methods for determining specific binding are further described below and are well known in the art.

When an antibody is said to "compete with" a particular monoclonal antibody, it means that the antibody competes with the monoclonal antibody in a binding assay using either recombinant Siglec-10 molecules or surface expressed Siglec-10 molecules. For example, if a test antibody reduces the binding of a reference antibody to a Siglec-10 polypeptide or Siglec-10-expressing cell in a binding assay, the antibody is said to "compete" respectively with the reference antibody.

The term "affinity", as used herein, means the strength of the binding of an antibody to an epitope. The affinity of an antibody is given by the dissociation constant Kd, defined as [Ab]×[Ag]/[Ab-Ag], where [Ab-Ag] is the molar concentration of the antibody-antigen complex, [Ab] is the molar concentration of the unbound antibody and [Ag] is the molar concentration of the unbound antigen. The affinity constant $K_a$ is defined by 1/Kd. Methods for determining the affinity of mAbs can be found in Harlow, et al., Antibodies: A Laboratory Manual, Cold Spring Harbor Laboratory Press, Cold Spring Harbor, N.Y., 1988), Coligan et al., eds., Current Protocols in Immunology, Greene Publishing Assoc. and Wiley Interscience, N.Y., (1992, 1993), and Muller, Meth. Enzymol. 92:589-601 (1983), which references are entirely incorporated herein by reference. One standard method well known in the art for determining the affinity of mAbs is the use of surface plasmon resonance (SPR) screening (such as by analysis with a BIAcore™ SPR analytical device).

The term "epitope" refers to an antigenic determinant, and is the area or region on an antigen to which an antibody binds. A protein epitope may comprise amino acid residues directly involved in the binding as well as amino acid residues which are effectively blocked by the specific antigen binding antibody or peptide, i.e., amino acid residues within the "footprint" of the antibody. It is the simplest form or smallest structural area on a complex antigen molecule that can combine with e.g., an antibody or a receptor. Epitopes can be linear or conformational/structural. The term "linear epitope" is defined as an epitope composed of amino acid residues that are contiguous on the linear sequence of amino acids (primary structure). The term "conformational or structural epitope" is defined as an epitope composed of amino acid residues that are not all contiguous and thus represent separated parts of the linear sequence of amino acids that are brought into proximity to one another by folding of the molecule (secondary, tertiary and/or quaternary structures). A conformational epitope is dependent on the 3-dimensional structure. The term 'conformational' is therefore often used interchangeably with 'structural'.

The term "deplete" or "depleting", with respect to Siglec-10-expressing cells (e.g. Siglec-10 expressing lymphocytes) means a process, method, or compound that results in killing, elimination, lysis or induction of such killing, elimination or lysis, so as to negatively affect the number of such Siglec-10-expressing cells present in a sample or in a subject. "Non-depleting", with reference to a process, method, or compound means that the process, method, or compound is not depleting.

The term "agent" is used herein to denote a chemical compound, a mixture of chemical compounds, a biological macromolecule, or an extract made from biological materials. The term "therapeutic agent" refers to an agent that has biological activity.

For the purposes herein, a "humanized" or "human" antibody refers to an antibody in which the constant and variable framework region of one or more human immunoglobulins is fused with the binding region, e.g. the CDR, of an animal immunoglobulin. Such antibodies are designed to maintain the binding specificity of the non-human antibody from which the binding regions are derived, but to avoid an immune reaction against the non-human antibody. Such antibodies can be obtained from transgenic mice or other animals that have been "engineered" to produce specific human antibodies in response to antigenic challenge (see, e.g., Green et al. (1994) Nature Genet 7:13; Lonberg et al. (1994) Nature 368:856; Taylor et al. (1994) Int Immun 6:579, the entire teachings of which are herein incorporated by reference). A fully human antibody also can be constructed by genetic or chromosomal transfection methods, as well as phage display technology, all of which are known in the art (see, e.g., McCafferty et al. (1990) Nature 348:552-553). Human antibodies may also be generated by in vitro activated B cells (see, e.g., U.S. Pat. Nos. 5,567,610 and 5,229,275, which are incorporated in their entirety by reference).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "hypervariable region" when used herein refers to the amino acid residues of an antibody that are responsible for antigen binding. The hypervariable region generally comprises amino acid residues from a "complementarity-determining region" or "CDR" (e.g. residues 24-34 (L1), 50-56 (L2) and 89-97 (L3) in the light-chain variable domain and 31-35 (H1), 50-65 (H2) and 95-102 (H3) in the heavy-chain variable domain; Kabat et al. 1991) and/or those residues from a "hypervariable loop" (e.g. residues 26-32 (L1), 50-52 (L2) and 91-96 (L3) in the light-chain variable domain and 26-32 (H1), 53-55 (H2) and 96-101 (H3) in the heavy-chain variable domain; Chothia and Lesk, J. Mol. Biol 1987; 196:901-917), or a similar system for determining essential amino acids responsible for antigen binding. Typically, the numbering of amino acid residues in this region is performed by the method described in Kabat et al., supra. Phrases such as "Kabat position", "variable domain residue numbering as in Kabat" and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

By "framework" or "FR" residues as used herein is meant the region of an antibody variable domain exclusive of those regions defined as CDRs. Each antibody variable domain framework can be further subdivided into the contiguous regions separated by the CDRs (FR1, FR2, FR3 and FR4).

The terms "Fc domain," "Fc portion," and "Fc region" refer to a C-terminal fragment of an antibody heavy chain, e.g., from about amino acid (aa) 230 to about aa 450 of human γ (gamma) heavy chain or its counterpart sequence in other types of antibody heavy chains (e.g., α, δ, ε and μ for human antibodies), or a naturally occurring allotype thereof. Unless otherwise specified, the commonly accepted Kabat amino acid numbering for immunoglobulins is used throughout this disclosure (see Kabat et al. (1991) Sequences of Protein of Immunological Interest, 5th ed., United States Public Health Service, National Institute of Health, Bethesda, Md.).

The terms "isolated", "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

Within the context herein, the term antibody that "binds" a polypeptide or epitope designates an antibody that binds said determinant with specificity and/or affinity.

The term "identity" or "identical", when used in a relationship between the sequences of two or more polypeptides, refers to the degree of sequence relatedness between polypeptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988).

Methods for determining identity are designed to give the largest match between the sequences tested. Methods of determining identity are described in publicly available computer programs. Computer program methods for determining identity between two sequences include the GCG program package, including GAP (Devereux et al., Nucl. Acid. Res. 12, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

Production of Antibodies

The anti-Siglec-10 antigen binding domain or protein that comprises such (e.g. antibody, Fc-protein, etc.) that can be used for the treatment of disease (e.g. cancers, infectious disease) binds an extra-cellular portion of human Siglec-10 receptor and reduces the inhibitory activity of human Siglec-10 receptor expressed on the surface of a Siglec-10 positive lymphocyte. In one embodiment an -Siglec-10 antigen binding domain or protein that comprises such inhibits the ability of a sialic acid molecule to cause inhibitory signalling by a Siglec-10 in a lymphocyte, e.g. an NK cell, a B cell, a T cell. In one embodiment the anti-Siglec10 antigen binding domain or protein that comprises such competes with an antibody of the disclosure in binding to a Siglec-10. In one embodiment the anti-Siglec-10 antigen binding domain or protein that comprises such blocks the interaction between a soluble Siglec-10 protein and a tumor cell bearing ligands of Siglec-10, e.g. an MDA-MB-231 cell, a HCT116 cell and/or a A375 cell.

In one aspect, an anti-Siglec-10 antigen binding domain or protein that comprises such is an antibody selected from a full-length antibody, an antibody fragment, and a synthetic or semi-synthetic antibody-derived molecule.

In one aspect, an anti-Siglec-10 antibody is an antibody selected from a fully human antibody, a humanized antibody, and a chimeric antibody.

In one aspect, an anti-Siglec-10 antibody is a fragment of an antibody selected from IgA, an IgD, an IgG, an IgE and an IgM antibody.

In one aspect, an anti-Siglec-10 antibody is a fragment of an antibody comprising a constant or Fc domain selected from IgG1, IgG2, IgG3 and IgG4, optionally modified compared to a naturally occurring constant or Fc domain.

In one aspect, an anti-Siglec-10 antibody is an antibody fragment selected from a Fab fragment, a Fab' fragment, a Fab'-SH fragment, a F(ab)2 fragment, a F(ab')2 fragment, an Fv fragment, a Heavy chain Ig (a llama or camel Ig), a $V_{HH}$ fragment, a single domain FV, and a single-chain antibody fragment.

In one aspect, the antibody is a synthetic or semisynthetic antibody-derived molecule selected from a scFV, a dsFV, a minibody, a diabody, a triabody, a kappa body, an IgNAR; and a multispecific antibody. In one aspect, the antibody is a multispecific antigen binding protein (e.g. a bi-specific or tri-specific antibody) that comprises a first antigen binding domain that binds Siglec-10 and a second antigen binding domain that binds a protein of interest other than Siglec-10.

In one aspect, an antibody or antigen binding domain binds to Siglec-10 with a binding affinity (e.g. $K_D$) at least 10-fold lower, optionally at least 100-fold lower, than to a further human Siglec protein, e.g., Siglec-3, -5, -6, -7, -8, -9, -11 and/or -12.

In one aspect, the antibody is in at least partially purified form.

In one aspect, the antibody is in essentially isolated form.

An antibody or antigen binding domain may be produced by a variety of techniques known in the art. Typically, they are produced by immunization of a non-human animal, preferably a mouse, with an immunogen comprising a Siglec polypeptide, e.g., a human Siglec-10 polypeptide. The Siglec polypeptide may comprise the full length sequence of a human Siglec-10 polypeptide, or a fragment or derivative thereof, typically an immunogenic fragment, i.e., a portion of the polypeptide comprising an epitope exposed on the surface of cells expressing a Siglec-10 polypeptide. Such fragments typically contain at least about 7 consecutive amino acids of the mature polypeptide sequence, even more preferably at least about 10 consecutive amino acids thereof. Fragments typically are essentially derived from the extracellular domain of the receptor. In one embodiment, the immunogen comprises a wild-type human Siglec-10 polypeptide in a lipid membrane, typically at the surface of a cell. In a specific embodiment, the immunogen comprises intact cells, particularly intact human cells, optionally treated or lysed. In another embodiment, the polypeptide is a recombinant Siglec-10 polypeptide.

The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, N.Y. (1988), the entire disclosure of which is herein incorporated by reference). The immunogen is suspended or dissolved in a buffer, optionally with an adjuvant, such as complete or incomplete Freund's adjuvant. Methods for determining the amount of immunogen, types of buffers and amounts of adjuvant are well known to those of skill in the art and are not limiting in any way. These parameters may be different for different immunogens, but are easily elucidated.

Similarly, the location and frequency of immunization sufficient to stimulate the production of antibodies is also well known in the art. In a typical immunization protocol, the non-human animals are injected intraperitoneally with antigen on day 1 and again about a week later. This is followed by recall injections of the antigen around day 20, optionally with an adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be used as long as they result in the production of B cells expressing an antibody directed to the antigen used in immunization.

In an alternate embodiment, lymphocytes from a non-immunized non-human mammal are isolated, grown in vitro, and then exposed to the immunogen in cell culture. The lymphocytes are then harvested and the fusion step described below is carried out.

For monoclonal antibodies, the next step is the isolation of splenocytes from the immunized non-human mammal and the subsequent fusion of those splenocytes with an immortalized cell in order to form an antibody-producing hybridoma. The isolation of splenocytes from a non-human mammal is well-known in the art and typically involves removing the spleen from an anesthetized non-human mammal, cutting it into small pieces and squeezing the splenocytes from the splenic capsule through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the lymphocytes can be fused to an immortal cell line. This is typically a mouse myeloma cell line, although many other immortal cell lines useful for creating hybridomas are known in the art. Murine myeloma lines include, but are not limited to, those derived from MOPC-21 and MPC-11 mouse tumors available from the Salk Institute Cell Distribution Center, San Diego, U.S.A, X63 Ag8653 and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Hybridomas are typically grown on a feeder layer of macrophages. The macrophages are preferably from littermates of the non-human mammal used to isolate splenocytes and are typically primed with incomplete Freund's adjuvant or the like several days before plating the hybridomas. Fusion methods are described in Goding, "Monoclonal Antibodies: Principles and Practice," pp. 59-103 (Academic Press, 1986), the disclosure of which is herein incorporated by reference.

The cells are allowed to grow in the selection media for sufficient time for colony formation and antibody production. This is usually between about 7 and about 14 days.

The hybridoma colonies are then assayed for the production of antibodies that specifically bind to Siglec polypeptide gene products. The assay is typically a colorimetric ELISA-type assay, although any assay may be employed that can be adapted to the wells that the hybridomas are grown in. Other assays include radioimmunoassays or fluorescence activated cell sorting. The wells positive for the desired antibody production are examined to determine if one or more distinct colonies are present. If more than one colony is present, the cells may be re-cloned and grown to ensure that only a single cell has given rise to the colony producing the desired antibody. Typically, the antibodies will also be tested for the ability to bind to Siglec-10 polypeptides, e.g., Siglec-10-expressing cells.

Hybridomas that are confirmed to produce a monoclonal antibody can be grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by gel electrophoresis, dialysis, chromatography using protein A or protein G-Sepharose, or an anti-mouse Ig linked to a solid support such as agarose or Sepharose beads (all described, for example, in the Antibody Purification Handbook, Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

Positive wells with a single apparent colony are typically re-cloned and re-assayed to insure only one monoclonal antibody is being detected and produced.

Antibodies may also be produced by selection of combinatorial libraries of immunoglobulins, as disclosed for instance in (Ward et al. Nature, 341 (1989) p. 544, the entire disclosure of which is herein incorporated by reference).

Once antibodies are identified that are capable of binding Siglec and/or having other desired properties, they will also typically be assessed, using standard methods including those described herein, for their ability to bind to other polypeptides, including other Siglec polypeptides and/or unrelated polypeptides. Ideally, the antibodies only bind with substantial affinity to Siglec-10, and do not bind at a significant level to unrelated polypeptides, notably polypeptides other than CD33-related Siglecs, or Siglecs other than the desired Siglec-10. However, it will be appreciated that, as long as the affinity for Siglec-10 is substantially greater (e.g., 5×, 10×, 50×, 100×, 500×, 1000×, 10,000×, or more) than it is for other Siglecs and/or other, unrelated polypeptides), then the antibodies are suitable for use in the present methods.

Upon immunization and production of antibodies in a vertebrate or cell, particular selection steps may be performed to isolate antibodies as claimed. In this regard, the disclosure also relates to methods of producing such antibodies, comprising: (a) providing a plurality of antibodies that bind Siglec-10; and (b) selecting antibodies from step (a) that are capable of inhibiting the Siglec-10, optionally that are capable inhibiting the interactions between a Siglec-10 polypeptide and a human MDA-MB-231 cell, an A375 cell or a HCT 116 cell, and optionally further (c) selecting antibodies from step (a) or (b) whose inhibitory activity is independent of the ability to cause down-modulation (e.g., internalization) of cell surface Siglec10 in a cell, optionally selecting antibodies that do or do not substantially cause down-modulation (e.g., internalization) of cell surface Siglec-10 in a cell. In one embodiment a non-human animal is used to produce the antibodies, such as a rodent, bovine, porcine, fowl, horse, rabbit, goat, or sheep.

The anti-Siglec-10 antibodies can be prepared as non-depleting antibodies such that they have reduced, or substantially lack specific binding to human Fcγ receptors. Such antibodies may comprise constant regions of various heavy chains that are known not to bind, or to have low binding affinity for, Fcγ receptors. One such example is a human IgG4 constant region. Alternatively, antibody fragments that do not comprise constant regions, such as Fab or F(ab')2 fragments, can be used to avoid Fc receptor binding. Fc receptor binding can be assessed according to methods known in the art, including for example testing binding of an antibody to Fc receptor protein in a BIACORE assay. Also, any antibody isotype can be used in which the Fc portion is modified to minimize or eliminate binding to Fc receptors (see, e.g., WO03101485, the disclosure of which is herein incorporated by reference). Assays such as, e.g., cell based assays, to assess Fc receptor binding are well known in the art, and are described in, e.g., WO03101485.

The DNA encoding an antibody that binds an epitope present on Siglec polypeptides is isolated from the hybridoma and placed in an appropriate expression vector for transfection into an appropriate host. The host is then used for the recombinant production of the antibody, or variants thereof, such as a humanized version of that monoclonal antibody, active fragments of the antibody, chimeric antibodies comprising the antigen recognition portion of the antibody, or versions comprising a detectable moiety.

DNA encoding a monoclonal antibodies can be readily isolated and sequenced using conventional procedures (e.g., by using oligonucleotide probes that are capable of binding specifically to genes encoding the heavy and light chains of murine antibodies). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. As described elsewhere in the present specification, such DNA sequences can be modified for any of a large number of purposes, e.g., for humanizing antibodies, producing fragments or derivatives, or for modifying the sequence of the antibody, e.g., in the antigen binding site in order to optimize the binding specificity of the antibody. Recombinant expression in bacteria of DNA encoding the antibody is well known in the art (see, for example, Skerra et al., Curr. Opinion in Immunol., 5, pp. 256 (1993); and Pluckthun, Immunol. 130, p. 151 (1992).

In order to direct the identification to antibodies that bind Siglec-10 towards those that bind substantially or essentially the same region or epitope on Siglec-10 as monoclonal antibody S10-A, S10-B or S10-C, any one of a variety of immunological screening assays in which antibody competition is assessed can be used. Many such assays are routinely practiced and are well known in the art (see, e.g., U.S. Pat. No. 5,660,827, issued Aug. 26, 1997, which is specifically incorporated herein by reference).

For example, where the test antibodies to be examined are obtained from different source animals, or are even of a different Ig isotype, a simple competition assay may be employed in which the control (S10-A, S10-B or S10-C, for example) and test antibodies are admixed (or pre-adsorbed) and applied to a sample containing Siglec-10 polypeptides. Protocols based upon western blotting and the use of BIACORE analysis are suitable for use in such competition studies.

In certain embodiments, one pre-mixes the control antibodies (S10-A, S10-B or S10-C, for example) with varying amounts of the test antibodies (e.g., about 1:10 or about 1:100) for a period of time prior to applying to the Siglec-10 antigen sample. In other embodiments, the control and varying amounts of test antibodies can simply be admixed during exposure to the Siglec-10 antigen sample. As long as one can distinguish bound from free antibodies (e.g., by using separation or washing techniques to eliminate unbound antibodies) and S10-A, S10-B or S10-C) from the test antibodies (e.g., by using species-specific or isotype-specific secondary antibodies or by specifically labeling S10-A, S10-B or S10-C with a detectable label) one can determine if the test antibodies reduce the binding of S10-A, S10-B or S10-C to the antigens. The binding of the (labeled) control antibodies in the absence of a completely irrelevant antibody can serve as the control high value. The control low value can be obtained by incubating the labeled (e.g., S10-A) antibodies with unlabelled antibodies of exactly the same type (e.g., S10-A), where competition would occur and reduce binding of the labeled antibodies. In a test assay, a significant reduction in labeled antibody reactivity in the presence of a test antibody is indicative of a test antibody that may recognize substantially the same epitope, i.e., one that "cross-reacts" or competes with the labeled (e.g., S10-A) antibody. Any test antibody that reduces the binding of S10-A (or, e.g., S10-B or S10-C) to Siglec-10 antigens by at least about 50%, such as at least about 60%, or more preferably at least about 80% or 90% (e.g., about 65-100%), at any ratio of anti-Siglec-10 antibody:test antibody between about 1:10 and about 1:100 is considered to be an antibody that competes with S10-A (or the respective S10-B or S10-C). Preferably, such test antibody will reduce the binding of S10-A (or, e.g., S10-B or S10-C) to the Siglec-10 antigen by at least about 90% (e.g., about 95%).

Competition can also be assessed by, for example, a flow cytometry test. In such a test, cells bearing a given Siglec-10 polypeptide can be incubated first with S10-A, for example, and then with the test antibody labeled with a fluorochrome or biotin. The antibody is said to compete with S10-A if the binding obtained upon preincubation with a saturating amount of S10-A is about 80%, preferably about 50%, about 40% or less (e.g., about 30%, 20% or 10%) of the binding (as measured by mean of fluorescence) obtained by the antibody without preincubation with S10-A. Alternatively, an antibody is said to compete with S10-A if the binding obtained with a labelled S10-A antibody (by a fluorochrome or biotin) on cells preincubated with a saturating amount of test antibody is about 80%, preferably about 50%, about 40%, or less (e.g., about 30%, 20% or 10%) of the binding obtained without preincubation with the test antibody.

A simple competition assay in which a test antibody is pre-adsorbed and applied at saturating concentration to a surface onto which a Siglec-10 antigen is immobilized may also be employed. The surface in the simple competition assay is preferably a BIACORE chip (or other media suitable for surface plasmon resonance (SPR Biacore) analysis). The control antibody (e.g., S10-A) is then brought into contact with the surface at a Siglec-10-saturating concentration and the Siglec-10 and surface binding of the control antibody is measured. This binding of the control antibody is compared with the binding of the control antibody to the Siglec-10-containing surface in the absence of test antibody. In a test assay, a significant reduction in binding of the Siglec-10-containing surface by the control antibody in the presence of a test antibody can be indicative that the test antibody competes with the control antibody. Any test antibody that reduces the binding of control (such as S10-A) antibody to a Siglec-10 antigen by at least about 30% or more, preferably about 40%, can be considered to be an antibody that competes for binding to Siglec-10 with a control (e.g., S10-A). Preferably, such a test antibody will reduce the binding of the control antibody (e.g., S10-A) to the Siglec-10 antigen by at least about 50% (e.g., at least about 60%, at least about 70%, or more). It will be appreciated that the order of control and test antibodies can be reversed: that is, the control antibody can be first bound to the surface and the test antibody is brought into contact with the surface thereafter in a competition assay. Preferably, the antibody having higher affinity for the Siglec-10 antigen is bound to the surface first, as it will be expected that the decrease in binding seen for the second antibody (assuming the antibodies are cross-reacting) will be of greater magnitude. Further examples of such assays are provided in, e.g., Saunal (1995) J. Immunol. Methods 183: 33-41, the disclosure of which is incorporated herein by reference.

The antibodies will bind to Siglec-10-expressing NK and/or T cells from an individual, i.e. an individual that is a candidate for treatment with one of the herein-described methods using an anti-Siglec-10 antibody. Accordingly, once an antibody that specifically recognizes Siglec-10 on cells is obtained, it can optionally be tested for its ability to bind to Siglec10-positive cells (e.g. NK and/or T cells). In particular, prior to treating a patient with one of the present antibodies, one may optionally test the ability of the antibody to bind cells taken from the patient, e.g. in a blood sample or tumor biopsy, to maximize the likelihood that the therapy will be beneficial in the patient.

Antibodies can be used for diagnostic purposes to determine the presence or level of Siglec-10 expressing cells in a patient, for example as a biomarker to assess whether a patient is suitable for treatment with an anti-Siglec-10 agent, or for use in the herein-described therapeutic methods. To assess the binding of the antibodies to the cells, the antibodies can either be directly or indirectly labelled. When indirectly labelled, a secondary, labeled antibody is typically added.

Determination of whether an antibody binds within an epitope region can be carried out in ways known to the person skilled in the art. As one example of such mapping/characterization methods, an epitope region for an anti-Siglec-10 antibody may be determined by epitope "foot-printing" using chemical modification of the exposed amines/carboxyls in the Siglec-10 protein. One specific example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions can be identified at this point by peptic proteolysis, fast microbore high-performance liquid chromatography separation, and/or electrospray ionization mass spectrometry. See, e.g., Ehring H, Analytical Biochemistry, Vol. 267 (2) pp. 252-259 (1999) Engen, J. R. and Smith, D. L. (2001) Anal. Chem. 73, 256A-265A. Another example of a suitable epitope identification technique is nuclear magnetic resonance epitope mapping (NMR), where typically the position of the signals in two-dimensional NMR spectra of the free antigen and the antigen complexed with the antigen binding peptide, such as an antibody, are compared. The antigen typically is selectively isotopically labeled with 15N so that only signals corresponding to the antigen and no signals from the antigen binding peptide are seen in the NMR-spectrum. Antigen signals originating from amino acids involved in the interaction with the antigen binding peptide typically will shift position in the spectrum of the complex compared to the spectrum of the free antigen, and the amino acids involved in the binding can be identified that way. See, e.g., Ernst Schering Res Found Workshop. 2004; (44): 149-67; Huang et al., Journal of Molecular Biology, Vol. 281 (1) pp. 61-67 (1998); and Saito and Patterson, Methods. 1996 June; 9 (3): 516-24.

Epitope mapping/characterization also can be performed using mass spectrometry methods. See, e.g., Downard, J Mass Spectrom. 2000 April; 35 (4): 493-503 and Kiselar and Downard, Anal Chem. 1999 May 1; 71 (9): 1792-1801. Protease digestion techniques also can be useful in the context of epitope mapping and identification. Antigenic determinant-relevant regions/sequences can be determined by protease digestion, e.g. by using trypsin in a ratio of about 1:50 to Siglec-10 or o/n digestion at and pH 7-8, followed by mass spectrometry (MS) analysis for peptide identification. The peptides protected from trypsin cleavage by the anti-Siglec-10 binder can subsequently be identified by comparison of samples subjected to trypsin digestion and samples incubated with antibody and then subjected to digestion by e.g. trypsin (thereby revealing a footprint for the binder). Other enzymes like chymotrypsin, pepsin, etc., also or alternatively can be used in similar epitope characterization methods. Moreover, enzymatic digestion can provide a quick method for analyzing whether a potential antigenic determinant sequence is within a region of the Siglec-10 polypeptide that is not surface exposed and, accordingly, most likely not relevant in terms of immunogenicity/antigenicity.

Site-directed mutagenesis is another technique useful for elucidation of a binding epitope. For example, in "alanine-scanning", each residue within a protein segment is replaced with an alanine residue, and the consequences for binding affinity measured. If the mutation leads to a significant reduction in binding affinity, it is most likely involved in binding. Monoclonal antibodies specific for structural epitopes (i.e., antibodies which do not bind the unfolded protein) can be used to verify that the alanine-replacement does not influence overall fold of the protein. See, e.g., Clackson and Wells, Science 1995; 267:383-386; and Wells, Proc Natl Acad Sci USA 1996; 93:1-6.

Electron microscopy can also be used for epitope "footprinting". For example, Wang et al., Nature 1992; 355:275-278 used coordinated application of cryoelectron microscopy, three-dimensional image reconstruction, and X-ray crystallography to determine the physical footprint of a Fab-fragment on the capsid surface of native cowpea mosaic virus.

Other forms of "label-free" assay for epitope evaluation include surface plasmon resonance (SPR, BIACORE) and reflectometric interference spectroscopy (RifS). See, e.g., Fägerstam et al., Journal Of Molecular Recognition 1990; 3:208-14; Nice et al., J. Chromatogr. 1993; 646:159-168; Leipert et al., Angew. Chem. Int. Ed. 1998; 37:3308-3311; Kroger et al., Biosensors and Bioelectronics 2002; 17:937-944.

It should also be noted that an antibody binding the same or substantially the same epitope as an antibody can be identified in one or more of the exemplary competition assays described herein.

Once an antigen-binding compound having the desired binding for Siglec-10 is obtained it may be assessed for its ability to inhibit the interaction between a Siglec-10 polypeptide (e.g. a soluble Siglec-10 Fc polypeptide) and a sialic acid-bearing cell. The sialic acid-bearing cell can be for example a tumor cell, optionally a carcinoma tumor cell, a carcinoma cell, a breast carcinoma cell, a colorectal carcinoma cell, a malignant melanoma cell, a MDA-MB-231 cell (breast adenocarcinoma; ATCC® HTB-26™), an A375 cell (malignant melanoma; ATCC® CRL-1619™), an HCT 116 cell (colon carcinoma; ATCC® CCL-247™), and/or a WiDr cell (colorectal adenocarcinoma; ATCC® CCL-218™). This can be evaluated by a typical flow cytometry assay, examples of which are described herein.

Once an antigen-binding compound having the desired binding for Siglec-10 is obtained it may be assessed for its ability to inhibit Siglec-10. For example, if an anti-Siglec-10 antibody reduces or blocks Siglec-10 activation induced by a sialic acid ligand (e.g. as present on a cell, on a tumor cell, optionally a carcinoma tumor cell, a carcinoma cell, a breast carcinoma cell, a colorectal carcinoma cell, a malignant melanoma cell, a MDA-MB-231 cell, an A375 cell, an HCT 116 cell, and/or a WiDr cell, it can increase the activity (e.g. production of pro-inflammatory molecules, cytotoxicity) of Siglec-restricted lymphocytes. This can be evaluated by a typical cytotoxicity assay, examples of which are described below.

The inhibitory activity (i.e. cytotoxicity enhancing potential) of an antibody can also be assessed in any of a number of ways, e.g., by its effect on intracellular free calcium as described, e.g., in Sivori et al., J. Exp. Med. 1997; 186: 1129-1136, the disclosure of which is herein incorporated by reference, or by the effect on markers of NK cell cytotoxicity activation, such as degranulation marker CD107 or CD137 expression. NK or T cell activity for example can also be assessed using any cell based cytotoxicity assays, e.g., measuring any other parameter to assess the ability of the antibody to stimulate NK cells to kill target cells. The target cells can for example be any suitable cancer cell that expresses significant amount of sialic acid ligands of Siglec-10, for example carcinoma cells, breast carcinoma cells, colorectal carcinoma cells or malignant melanoma cells, optionally a cell line selected from the group consisting of MDA-MB-231 cells, A375 cells, HCT 116 cells, and WiDr cells. For examples of protocols for cytotoxicity assays, see, e.g., Sivori et al., J. Exp. Med. 1997; 186:1129-1136; Vitale et al., J. Exp. Med. 1998; 187:2065-2072; Pessino et al. J. Exp. Med. 1998; 188:953-960; Neri et al. Clin. Diag. Lab. Immun. 2001; 8:1131-1135; Pende et al. J. Exp. Med. 1999; 190:1505-1516, the entire disclosures of each of which are herein incorporated by reference).

In one embodiment, an antibody preparation causes at least a 10% augmentation in the cytotoxicity of a Siglec-10-restricted lymphocyte, preferably at least a 40% or 50% augmentation in cytotoxicity, or more preferably at least a 70% augmentation in cytotoxicity.

The activity of a cytotoxic lymphocyte can for example also be addressed using a cytokine-release assay, for example wherein lymphocytes (e.g. NK cells) are incubated with the antibody to stimulate the cytokine production of the cells (for example IFN-γ and TNF-α production). In an exemplary protocol for NK cell stimulation, IFN-γ production from PBMC is assessed by cell surface and intracytoplasmic staining and analysis by flow cytometry after 4 days in culture. Briefly, Brefeldin A (Sigma Aldrich) is added at a final concentration of 5 µg/ml for the last 4 hours of culture. The cells are then incubated with anti-CD3 and anti-CD56 mAb prior to permeabilization (IntraPrep™; Beckman Coulter) and staining with PE-anti-IFN-γ or PE-IgG1 (Pharmingen). GM-CSF and IFN-γ production from polyclonal activated NK cells are measured in supernatants using ELISA (GM-CSF: DuoSet Elisa, R&D Systems, Minneapolis, Minn., IFN-γ: OptEIA set, Pharmingen).

Antibody CDR Sequences

Antibody S10-A

The amino acid sequence of the heavy chain variable region of antibody S10-A is listed as SEQ ID NO: 12 (see also Table A), the amino acid sequence of the light chain variable region is listed as SEQ ID NO: 13 (see also Table A). In a specific embodiment, provided is an antibody that binds essentially the same epitope or determinant as monoclonal antibodies S10-A; optionally the antibody comprises the hypervariable region of antibody S10-A. In any of the embodiments herein, antibody S10-A can be characterized by the amino acid sequences and/or nucleic acid sequences encoding it. In one embodiment, the monoclonal antibody comprises the Fab or F(ab')$_2$ portion of S10-A. Also provided is a monoclonal antibody that comprises the heavy chain variable region of S10-A. According to one embodiment, the monoclonal antibody comprises the three CDRs of the heavy chain variable region of S10-A Also provided is a monoclonal antibody that further comprises the variable light chain variable region of S10-A or one, two or three of the CDRs of the light chain variable region of S10-A. The HCDR1, 2, 3 and LCDR1, 2, 3 sequences can optionally be specified as all (or each, independently) being those of the Kabat numbering system, those of the Chotia numbering system, those of the IMGT numbering, or any other suitable numbering system. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody S10-A are fused to an immunoglobulin constant region of the human IgG type, optionally a human constant region, optionally a human IgG1, IgG2, IgG3 or IgG4 isotype, optionally further comprising an amino acid substitution to reduce effector function (binding to human Fcγ receptors).

In another aspect, provided is an antibody, wherein the antibody comprises: a HCDR1 region of S10-A comprising an amino acid sequence SYWMH (SEQ ID NO: 14), or a sequence of at least 3, 4 or 5 contiguous amino acids thereof, optionally wherein one or more of these amino acids may be substituted by a different amino acid; a HCDR2 region of S10-A comprising an amino acid sequence YINPDTDSTEYNQKFRD (SEQ ID NO: 15), or a sequence of at least 4, 5, 6, 7, 8, 9 or 10 contiguous amino acids thereof, optionally wherein one or more of these amino acids may be substituted by a different amino acid; a HCDR3 region of S10-A comprising an amino acid sequence PYYRYAGYAMDY (SEQ ID NO: 16), or a sequence of at least 4, 5, 6, 7, 8, 9 or 10 contiguous amino acids thereof, optionally wherein one or more of these amino acids may be substituted by a different amino acid; a LCDR1 region of S10-A comprising an amino acid sequence KASQDINSYLS (SEQ ID NO: 17), or a sequence of at least 4, 5, 6, 7, 8, 9 or 10 contiguous amino acids thereof, optionally wherein one or more of these amino acids may be substituted by a different amino acid; a LCDR2 region of S10-A comprising an amino acid sequence RANRLVD (SEQ ID NO: 18), or a sequence of at least 4, 5, or 6 contiguous amino acids thereof, optionally wherein one or more of these amino acids may be substituted by a different amino acid; a LCDR3 region of S10-A comprising an amino acid sequence LQYDEFPWT (SEQ ID NO: 19), or a sequence of at least 4, 5, 6, 7, or 8 contiguous amino acids thereof, optionally wherein one or more of these amino acids may be deleted or substituted by a different amino acid.

Antibody S10-B

The amino acid sequence of the heavy chain variable region of antibody S10-B is listed as SEQ ID NO: 20 (see also Table A), the amino acid sequence of the light chain variable region is listed as SEQ ID NO: 21 (see also Table A). In a specific embodiment, provided is an antibody that binds essentially the same epitope or determinant as monoclonal antibodies S10-B; optionally the antibody comprises the hypervariable region of antibody S10-B. In any of the embodiments herein, antibody S10-B can be characterized by the amino acid sequences and/or nucleic acid sequences encoding it. In one embodiment, the monoclonal antibody comprises the Fab or F(ab')$_2$ portion of S10-B. Also provided is a monoclonal antibody that comprises the heavy chain variable region of S10-B. According to one embodiment, the monoclonal antibody comprises the three CDRs of the heavy chain variable region of S10-B Also provided is a monoclonal antibody that further comprises the variable light chain variable region of S10-B or one, two or three of the CDRs of the light chain variable region of S10-B. The HCDR1, 2, 3 and LCDR1, 2, 3 sequences can optionally be specified as all (or each, independently) being those of the Kabat numbering system, those of the Chotia numbering system, those of the IMGT numbering, or any other suitable numbering system. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody S10-B are fused to an immunoglobulin constant region of the human IgG type, optionally a human constant region, optionally a human IgG1, IgG2, IgG3 or IgG4 isotype, optionally further comprising an amino acid substitution to reduce effector function (binding to human Fcγ receptors).

In another aspect, provided is an antibody, wherein the antibody comprises: a HCDR1 region of S10-B comprising an amino acid sequence DYDVN (SEQ ID NO: 22), or a sequence of at least 3 or 4 contiguous amino acids thereof, optionally wherein one or more of these amino acids may be substituted by a different amino acid; a HCDR2 region of S10-B comprising an amino acid sequence MIWGDGITDYNSALKS (SEQ ID NO: 23), or a sequence of at least 4, 5, 6, 7, 8, 9 or 10 contiguous amino acids thereof, optionally wherein one or more of these amino acids may be substituted by a different amino acid; a HCDR3 region of S10-B comprising an amino acid sequence GGIYYFGNTYGYWFFDV (SEQ ID NO: 24), or a sequence of at least 4, 5, 6, 7, 8, 9 or 10 contiguous amino acids thereof, optionally wherein one or more of these amino acids may be substituted by a different amino acid; a LCDR1 region of S10-B comprising an amino acid sequence KSSQSLLNSR-TRKNYLA (SEQ ID NO: 25), or a sequence of at least 4, 5, 6, 7, 8, 9 or 10 contiguous amino acids thereof, optionally wherein one or more of these amino acids may be substituted by a different amino acid; a LCDR2 region of S10-B comprising an amino acid sequence WASTRES (SEQ ID NO: 26), or a sequence of at least 4, 5 or 6 10 contiguous amino acids thereof, optionally wherein one or more of these amino acids may be substituted by a different amino acid; a LCDR3 region of S10-B comprising an amino acid sequence QSYNLRT (SEQ ID NO: 27), or a sequence of at least 4, 5, 6 or 7 contiguous amino acids thereof, optionally wherein one or more of these amino acids may be deleted or substituted by a different amino acid.

Antibody S10-C

The amino acid sequence of the heavy chain variable region of antibody S10-C is listed as SEQ ID NO: 28 (see also Table A), the amino acid sequence of the light chain variable region is listed as SEQ ID NO: 29 (see also Table A). In a specific embodiment, provided is an antibody that binds essentially the same epitope or determinant as monoclonal antibodies 510-C; optionally the antibody comprises the hypervariable region of antibody S10-C. In any of the embodiments herein, antibody S10-C can be characterized by the amino acid sequences and/or nucleic acid sequences encoding it. In one embodiment, the monoclonal antibody comprises the Fab or F(ab')$_2$ portion of S10-C. Also provided is a monoclonal antibody that comprises the heavy chain variable region of S10-C. According to one embodiment, the monoclonal antibody comprises the three CDRs of the heavy chain variable region of S10-C Also provided is a monoclonal antibody that further comprises the variable light chain variable region of S10-C or one, two or three of the CDRs of the light chain variable region of S10-C. The HCDR1, 2, 3 and LCDR1, 2, 3 sequences can optionally be specified as all (or each, independently) being those of the Kabat numbering system, those of the Chotia numbering, those of the IMGT numbering, or any other suitable numbering system. Optionally any one or more of said light or heavy chain CDRs may contain one, two, three, four or five or more amino acid modifications (e.g. substitutions, insertions or deletions). Optionally, provided is an antibody where any of the light and/or heavy chain variable regions comprising part or all of an antigen binding region of antibody S10-C are fused to an immunoglobulin constant region of the human IgG type, optionally a human constant region, optionally a human IgG1, IgG2, IgG3 or IgG4 isotype, optionally further comprising an amino acid substitution to reduce effector function (binding to human Fcγ receptors).

In another aspect, provided is an antibody, wherein the antibody comprises: a HCDR1 region of S10-C comprising an amino acid sequence DYDVN (SEQ ID NO: 30), or a sequence of at least 3 or 4 contiguous amino acids thereof, optionally wherein one or more of these amino acids may be substituted by a different amino acid; a HCDR2 region of S10-C comprising an amino acid sequence MIWGDGIT-DYNSALKS (SEQ ID NO: 31), or a sequence of at least 4, 5, 6, 7, 8, 9 or 10 contiguous amino acids thereof, optionally wherein one or more of these amino acids may be substituted by a different amino acid; a HCDR3 region of S10-C comprising an amino acid sequence GGIYYFGN-TYGYWFFDV (SEQ ID NO: 32), or a sequence of at least 4, 5, 6, 7, 8, 9 or 10 contiguous amino acids thereof, optionally wherein one or more of these amino acids may be substituted by a different amino acid; a LCDR1 region of S10-C comprising an amino acid sequence KSSQSLLNSR-TRKNYLA (SEQ ID NO: 33), or a sequence of at least 4, 5, 6, 7, 8, 9 or 10 contiguous amino acids thereof, optionally wherein one or more of these amino acids may be substituted by a different amino acid; a LCDR2 region of S10-C comprising an amino acid sequence WASTRES (SEQ ID NO: 34), or a sequence of at least 4, 5 or 6 contiguous amino acids thereof, optionally wherein one or more of these amino acids may be substituted by a different amino acid; a LCDR3 region of S10-C comprising an amino acid sequence KQSYNLRT (SEQ ID NO: 35), or a sequence of at least 4, 5, 6 or 7 contiguous amino acids thereof, optionally wherein one or more of these amino acids may be deleted or substituted by a different amino acid.

In another aspect of any of the embodiments herein, any of the CDRs 1, 2 and 3 of the heavy and light chains of S10-A, S10-B or S10-C may be characterized by a sequence of at least 4, 5, 6, 7, 8, 9 or 10 contiguous amino acids thereof, and/or as having an amino acid sequence that shares at least 50%, 60%, 70%, 80%, 85%, 90% or 95% sequence identity with the particular CDR or set of CDRs listed in the corresponding SEQ ID NO.

In any of the antibodies, e.g., S10-A, S10-B or S10-C, the specified variable region and CDR sequences may comprise sequence modifications, e.g. a substitution (1, 2, 3, 4, 5, 6, 7, 8 or more sequence modifications). In one embodiment, a CDRs 1, 2 and/or 3 of the heavy and light chains comprises one, two, three or more amino acid substitutions, where the residue substituted is a residue present in a sequence of human origin. In one embodiment the substitution is a conservative modification. A conservative sequence modification refers to an amino acid modification that does not significantly affect or alter the binding characteristics of the antibody containing the amino acid sequence. Such conservative modifications include amino acid substitutions, additions and deletions. Modifications can be introduced into an antibody by standard techniques known in the art, such as site-directed mutagenesis and PCR-mediated mutagenesis. Conservative amino acid substitutions are typically those in which an amino acid residue is replaced with an amino acid residue having a side chain with similar physicochemical properties. Specified variable region and CDR sequences may comprise one, two, three, four or more amino acid insertions, deletions or substitutions. Where substitutions are made, preferred substitutions will be conservative modifications. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g. glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g. threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for retained function (i.e., the properties set forth herein) using the assays described herein.

TABLE A

| Antibody domain | SEQ ID NO: | Amino Acid Sequence |
|---|---|---|
| S10-A VH | 12 | QIQLQQSGAELEKPGASVKMSCK-ASGYTFTSYWMHWVKQRPGQGLEWIGYINPDTDSTEYNQKFRDKATLTAD-KSSSTAYMQLSSLTSEDSAVYYCAR-PYYRYAGYAMDYWGQGTSVTVSSASTKGP |
| S10-A VL | 13 | DIKMTQSPSSMYASLGERVTITCKASQDINSYLSWFQQKPGKSPKTLI-YRANRLVDGVPSRFSGSGSGQVYSLTISSLEYEDLGIY-YCLQYDEFPWTFGGGTKLEIKRTVAAP |
| S10-B VH | 20 | QVQLKESGPGLVAPSQSLSITCTVSGFSLTDYDVNWVRQPPGKGLEWLG-MIWGDGITDYNSALKSRLSISKDNSKSQVFLEMNSLQTDDTARYYCARG-GIYYFGNTYGYWFFDVWGAGTTVTVSSASTKGP |
| S10-B VL | 21 | DIVMTQSPSSLAVSTGEKVTMSCKSSQSLLNSRTRKNYL-AWYQQKPGQSPKLLIYWASTRESGVPDRFTGSGSGTDFTLTISSVQAED-LAVYYCKQSYNLRTFGGGTKLEIKRTVAAP |
| S10-C VH | 28 | QVQLKESGPGLVAPSQSLSITCTVSGFSLTDYDVNWVRQPPGKGLEWLG-MIWGDGITDYNSALKSRLSISKDNSKSQVFLEMNSLQTDDTARYYCARG-GIYYFGNTYGYWFFDVWGAGTTVTVSSASTKGP |
| S10-C VL | 29 | EILLTQSPSSLAVSTGEKVTMSCKSSQSLLNSRTRKNYL-AWYQQKPGQSPKLLIYWASTRESGVPDRFTGSGSGTDFTLTISSVQAED-LAVYYCKQSYNLRTFGGGTKLEIKRTVAAP |

Fragments and derivatives of antibodies (which are encompassed by the term "antibody" or "antibodies" as used in this application, unless otherwise stated or clearly contradicted by context) can be produced by techniques that are known in the art. "Fragments" comprise a portion of the intact antibody, generally the antigen binding site or variable region. Examples of antibody fragments include Fab, Fab', Fab'-SH, F (ab') 2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific (e.g. bispecific) antibodies formed from antibody fragments. Included, inter alia, are a nanobody, domain antibody, single domain antibody or a "dAb".

In certain embodiments, the DNA of a hybridoma producing an antibody, can be modified prior to insertion into an expression vector, for example, by substituting the coding sequence for human heavy- and light-chain constant domains in place of the homologous non-human sequences (e.g., Morrison et al., PNAS pp. 6851 (1984)), or by covalently joining to the immunoglobulin coding sequence all or part of the coding sequence for a non-immunoglobulin polypeptide. In that manner, "chimeric" or "hybrid" antibodies are prepared that have the binding specificity of the original antibody. Typically, such non-immunoglobulin polypeptides are substituted for the constant domains of an antibody.

The anti-Siglec-10 antibodies can be prepared such that they do not have substantial specific binding to human Fcγ receptors, e.g., any one or more of CD16A, CD16B, CD32A, CD32B and/or CD64). Such antibodies may comprise human constant regions of various heavy chains that have reduced binding to human Fcγ receptor such as CD16. One such example is a wild type human IgG4 constant region (IgG4 have minimal Fcγ receptor binding). A human IgG4 constant region can further comprise a stabilizing S228P (S241P) substitution) to retain bivalent binding ability in vivo by preventing Fab arm exchange. Alternatively, antibody fragments that do not comprise (or comprise portions of) constant regions, such as F(ab')2 fragments, can be used to avoid Fc receptor binding. Fc receptor binding can be assessed according to methods known in the art, including for example testing binding of an antibody to Fc receptor protein in a BIACORE assay. Also, generally any antibody IgG isotype can be used in which the Fc portion is modified (e.g., by introducing 1, 2, 3, 4, 5 or more amino acid substitutions) to minimize or eliminate binding to Fc receptors (see, e.g., WO 03/101485, the disclosure of which is herein incorporated by reference).

In one embodiment, the antibody can comprise one or more specific mutations in the Fc region that result in "Fc silent" antibodies that have minimal interaction with effector cells. Silenced effector functions can be obtained by mutation in the Fc region of the antibodies and have been described in the art: N297A mutation, the LALA mutations, (Strohl, W., 2009, Curr. Opin. Biotechnol. vol. 20(6):685-691); and D265A (Baudino et al., 2008, J. Immunol. 181: 6664-69) see also Heusser et al., WO2012/065950, the disclosures of which are incorporated herein by reference. In one embodiment, an antibody comprises one, two, three or more amino acid substitutions in the hinge region. In one embodiment, the antibody is an IgG1 or IgG2 and comprises one, two or three substitutions at residues 233-236, optionally 233-238 (EU numbering). In one embodiment, the antibody is an IgG4 and comprises one, two or three substitutions at residues 327, 330 and/or 331 (EU numbering). Examples of silent Fc IgG1 antibodies are the LALA mutant comprising L234A and L235A mutation in the IgG1 Fc amino acid sequence. Another example of an Fc silent mutation is a mutation at residue D265, or at D265 and P329 for example as used in an IgG1 antibody as the DAPA (D265A, P329A) mutation (U.S. Pat. No. 6,737,056). Another silent IgG1 antibody comprises a mutation at residue N297 (e.g. N297A, N297S mutation), which results in aglycosylated/nonglycosylated antibodies. Other silent mutations include: substitutions at residues L234 and G237 (L234A/G237A); substitutions at residues S228, L235 and R409 (S228P/L235E/R409K,T,M,L); substitutions at residues H268, V309, A330 and A331 (H268Q/V309L/A330S/A331S); substitutions at residues C220, C226, C229 and P238 (C220S/C226S/C229S/P238S); substitutions at residues C226, C229, E233, L234 and L235 (C226S/C229S/E233P/L234V/L235A; substitutions at residues K322, L235 and L235 (K322A/L234A/L235A); substitutions at residues L234, L235 and P331 (L234F/L235E/P331S); substitutions at residues 234, 235 and 297; substitutions at residues E318, K320 and K322 (L235E/E318A/K320A/K322A); substitutions at residues (V234A, G237A, P238S); substitutions at residues 243 and 264; substitutions at residues 297 and 299; substitutions such that residues 233, 234, 235, 237, and 238 defined by the EU numbering system, comprise a sequence selected from PAAAP, PAAAS and SAAAS (see WO2011/066501).

Fc silent antibodies result in no or low ADCC activity, meaning that an Fc silent antibody exhibits an ADCC activity that is below 50% specific cell lysis. Preferably an antibody substantially lacks ADCC activity, e.g., the Fc silent antibody exhibits an ADCC activity (specific cell lysis) that is below 5% or below 1%. Fc silent antibodies can also result in lack of FcγR-mediated cross-linking of Siglec-10 at the surface of a Siglec-10-expressing cell.

In one embodiment, the antibody has a substitution in a heavy chain constant region at any one, two, three, four, five or more of residues selected from the group consisting of: 220, 226, 229, 233, 234, 235, 236, 237, 238, 243, 264, 268, 297, 298, 299, 309, 310, 318, 320, 322, 327, 330, 331 and 409 (numbering of residues in the heavy chain constant region is according to EU numbering according to Kabat). In one embodiment, the antibody comprises a substitution at residues 234, 235 and 322. In one embodiment, the antibody has a substitution at residues 234, 235 and 331.

In one embodiment, the Fc silent antibody comprises an Fc domain comprising an amino acid substitution at residues 234, 235 and 331, for example the "TM" mutation having substitutions L234F, L235E and P331S. In one embodiment, the antibody comprises an Fc domain comprising an amino acid substitution at residues 234, 235 and 322, or at residues 234, 235 and 331, described in US Patent publication no. US2015/0125444, wherein residue 234 is F (phenylalanine); residue 235 is Alanine (A), Asparagine (N), Phenylalanine (F), Glutamine (Q), or Valine (V); residue 322 is Alanine (A), Aspartic acid (D), Glutamic acid (E), Histidine (H), Asparagine (N), or Glutamine (Q); and residue 331 is Alanine (A) or Glycine (G). Amino acid residues are indicated according to EU numbering according to Kabat.

While antibodies that are used as pure blockers will preferably have reduced binding to human Fc receptors, it will be appreciated that in certain embodiments, antibodies of the disclosure can be configured to possess agonist activity. Such antibodies can be useful for example to treat or prevent an inflammatory or autoimmune disorder (e.g. GvHD, sepsis, multiple sclerosis). This in one embodiment, an anti-Siglec-10 antibody of the disclosure has agonist activity; in such embodiments, the antibodies can comprise an Fc domain capable of being bound (e.g. with high affinity, affinity comparable to a wild-type human IgG1 or IgG3 Fc domain) by the human FcγR (e.g. CD16A, CD16B, CD32A, CD32B and/or CD64). In one embodiment, the antibody comprises a human IgG1 Fc domain.

In one embodiment, the antibody comprises an Fc domain comprising an amino acid substitution that increases binding to human FcRn polypeptides in order to increase the in vivo half-life of the antibody. Exemplary mutations are described in Strohl, W., 2009, Curr. Opin. Biotechnol. vol. 20(6):685-691, the disclosure of which is incorporated herein by reference. Examples of substitutions used in antibodies of human IgG1 isotype are substitutions at residues M252, S254 and T256; substitutions at residues T250 and M428; substitutions at residue N434; substitutions at residues H433 and N434; substitutions at residues T307, E380 and N434; substitutions at residues T307, E380, and N434; substitutions at residues M252, S254, T256, H433, N434 and 436; substitutions at residue 1253; substitutions at residues P257, N434, D376 and N434.

In one embodiment, the antibody comprises an Fc domain comprising an amino acid substitution that confers decreased sensitivity to cleavage by proteases. Matrix metalloproteinases (MMPs) represent the most prominent family of proteinases associated with tumorigenesis. While cancer cells can express MMPs, the bulk of the extracellular MMP is provided by different types of stromal cells that infiltrate the tumor and each produce a specific set of proteinases and proteinase inhibitors, which are released into the extracellular space and specifically alter the milieu around the tumor. The MMPs present in the tumor microenvironment can cleave antibodies within the hinge region and may thus lead to the inactivation of therapeutic antibodies that are designed to function within the tumor site. In one embodiment, the Fc domain comprising an amino acid substitution has decreased sensitivity to cleavage by any one, two, three or more (or all of) of the proteases selected from the group consisting of: GluV8, IdeS, gelatinase A (MMP2), gelatinase B (MMP-9), matrix metalloproteinase-7 (MMP-7), stromelysin (MMP-3), and macrophage elastase (MMP-12). In one embodiment, the antibody decreased sensitivity to cleavage comprises an Fc domain comprising an amino acid substitution at residues E233-L234 and/or L235. In one embodiment, the antibody comprises an Fc domain comprising an amino acid substitution at residues E233, L234, L235 and G236. In one embodiment, the antibody comprises an Fc domain comprising an amino acid substitution at one or more residues 233-238, e.g., such that E233-L234-L235-G236 sequence is replaced by P233-V234-A235 (G236 is deleted). See, e.g., WO99/58572 and WO2012087746, the disclosures of which are incorporated herein by reference.

Optionally an antibody is humanized. "Humanized" forms of antibodies are specific chimeric immunoglobulins, immunoglobulin chains or fragments thereof (such as Fv, Fab, Fab', F (ab') 2, or other antigen-binding subsequences of antibodies) which contain minimal sequence derived from the murine immunoglobulin. For the most part, humanized antibodies are human immunoglobulins (recipient antibody) in which residues from a complementary-determining region (CDR) of the recipient are replaced by residues from a CDR of the original antibody (donor antibody) while maintaining the desired specificity, affinity, and capacity of the original antibody.

In some instances, Fv framework residues of the human immunoglobulin may be replaced by corresponding non-human residues. Furthermore, humanized antibodies can comprise residues that are not found in either the recipient antibody or in the imported CDR or framework sequences. These modifications are made to further refine and optimize antibody performance. In general, the humanized antibody will comprise substantially all of at least one, and typically two, variable domains, in which all or substantially all of the CDR regions correspond to those of the original antibody and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., Nature, 321, pp. 522 (1986); Reichmann et al, Nature, 332, pp. 323 (1988); Presta, Curr. Op. Struct. Biol., 2, pp. 593 (1992); Verhoeyen et Science, 239, pp. 1534; and U.S. Pat. No. 4,816,567, the entire disclosures of which are herein incorporated by reference.) Methods for humanizing the antibodies are well known in the art.

The choice of human variable domains, both light and heavy, to be used in making the humanized antibodies is very important to reduce antigenicity. According to the so-called "best-fit" method, the sequence of the variable domain of an antibody is screened against the entire library of known human variable-domain sequences. The human sequence which is closest to that of the mouse is then accepted as the human framework (FR) for the humanized antibody (Sims et al., J. Immunol. 151, pp. 2296 (1993); Chothia and Lesk, J. Mol. 196, 1987, pp. 901). Another method uses a particular framework from the consensus sequence of all human antibodies of a particular subgroup of light or heavy chains. The same framework can be used for several different humanized antibodies (Carter et al., PNAS 89, pp. 4285 (1992); Presta et al., J. Immunol., 151, p. 2623 (1993)).

It is further important that antibodies be humanized with retention of high affinity for Siglec receptors and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen (s), is achieved. In general, the CDR residues are directly and most substantially involved in influencing antigen binding.

Another method of making "humanized" monoclonal antibodies is to use a XenoMouse (Abgenix, Fremont, Calif.) as the mouse used for immunization. A XenoMouse is a murine host according that has had its immunoglobulin genes replaced by functional human immunoglobulin genes. Thus, antibodies produced by this mouse or in hybridomas made from the B cells of this mouse, are already humanized (they can also be referred to as "human" antibodies). The XenoMouse is described in U.S. Pat. No. 6,162,963, which is herein incorporated in its entirety by reference. Human antibodies may generally be produced according to various other techniques, such as by using, for immunization, other transgenic animals that have been engineered to express a human antibody repertoire (Jakobovitz et al., Nature 362 (1993) 255), or by selection of antibody repertoires using phage display methods. Such techniques are known to the skilled person and can be implemented starting from monoclonal antibodies as disclosed in the present application.

An anti-Siglec antibody can be incorporated in a pharmaceutical formulation comprising in a concentration from 1 mg/ml to 500 mg/ml, wherein said formulation has a pH from 2.0 to 10.0. The formulation may further comprise a buffer system, preservative(s), tonicity agent(s), chelating agent(s), stabilizers and surfactants. In one embodiment, the pharmaceutical formulation is an aqueous formulation, i.e., formulation comprising water. Such formulation is typically a solution or a suspension. In a further embodiment, the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, whereto the physician or the patient adds solvents and/or diluents prior to use.

In another embodiment, the pharmaceutical formulation is a dried formulation (e.g. freeze-dried or spray-dried) ready for use without any prior dissolution.

In a further aspect, the pharmaceutical formulation comprises an aqueous solution of such an antibody, and a buffer, wherein the antibody is present in a concentration from 1 mg/ml or above, and wherein said formulation has a pH from about 2.0 to about 10.0.

In a another embodiment, the pH of the formulation is in the range selected from the list consisting of from about 2.0 to about 10.0, about 3.0 to about 9.0, about 4.0 to about 8.5, about 5.0 to about 8.0, and about 5.5 to about 7.5.

In a further embodiment, the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment.

In a further embodiment, the formulation further comprises a pharmaceutically acceptable preservative. In a further embodiment, the formulation further comprises an isotonic agent. In a further embodiment, the formulation also comprises a chelating agent. In a further embodiment the formulation further comprises a stabilizer. In a further embodiment, the formulation further comprises a surfactant. For convenience reference is made to Remington: The Science and Practice of Pharmacy, 19$^{th}$ edition, 1995.

It is possible that other ingredients may be present in the peptide pharmaceutical formulation. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation.

Pharmaceutical compositions containing an antibody may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen. Administration of pharmaceutical compositions may be through several routes of administration, for example, subcutaneous, intramuscular, intraperitoneal, intravenous, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Suitable antibody formulations can also be determined by examining experiences with other already developed therapeutic monoclonal antibodies. Several monoclonal antibodies have been shown to be efficient in clinical situations, such as RITUXAN (Rituximab), HERCEPTIN (Trastuzumab), XOLAIR (Omalizumab), BEXXAR (Tositumomab), CAMPATH (Alemtuzumab), ZEVALIN, ONCOLYM and similar formulations may be used with the antibodies. For example, a monoclonal antibody can be supplied at a concentration of 10 mg/mL in either 100 mg (10 mL) or 500 mg (50 mL) single-use vials, formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5. In another embodiment, the antibody is supplied in a formulation comprising about 20 mM Na-Citrate, about 150 mM NaCl, at pH of about 6.0.

Diagnosis and Treatment of Malignancies

Methods of treating an individual, notably a human patient, using an anti-Siglec antibody as described herein are also provided for. In one embodiment, provided is for the use of an antibody as described herein in the preparation of a pharmaceutical composition for administration to a human patient. Typically, the patient suffers from, or is at risk for, cancer or infectious disease, e.g. a bacterial or a viral disease.

For example, in one aspect, provided is a method of potentiating the activity of Siglec-10-restricted leukocytes in a patient in need thereof, comprising the step of administering a neutralizing anti-Siglec-10 antibody to said patient. The antibody can be for example a human or humanized anti-Siglec-10 antibody, which antibody reduces or prevents sialic acid-mediated activation of the Siglec-10 protein. In one embodiment, the method directed at increasing the activity of such leukocytes in patients having a disease in which increased leukocyte (e.g. B, NK and/or T cell) activity is beneficial, which involves, affects or is caused by cells susceptible to lysis by B, NK or T cells, or which is caused or characterized by insufficient B, NK or T cell activity, such as a cancer or an infectious disease.

More specifically, the methods and compositions are utilized for the treatment of a variety of cancers and other proliferative diseases. Because these methods operate by enhancing an immune response via blockade of inhibitory receptors on lymphocytes, they are applicable to a broad range of cancers. In one embodiment, a human patient treated with an anti-Siglec-10 antibody has liver cancer, bone cancer, pancreatic cancer, skin cancer, cancer of the head or neck, breast cancer, lung cancer, non-small cell lung cancer (NSCLC), castrate resistant prostate cancer (CRPC), melanoma, uterine cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers. The present antibodies are also useful for treatment of metastatic cancers. Patients can be tested or selected for one or more of the above described clinical attributes prior to, during or after treatment.

The anti-Siglec-10 antibody based treatment can also be used to treat or prevent infectious diseases, including preferably any infections caused by infection by viruses, bacteria, protozoa, molds or fungi.

The antibody compositions may be used in as monotherapy or combined treatments with one or more other therapeutic agents, including agents normally utilized for the particular therapeutic purpose for which the antibody is being administered. The additional therapeutic agent will normally be administered in amounts and treatment regimens typically used for that agent in a monotherapy for the particular disease or condition being treated. Such therapeutic agents include, but are not limited to anti-cancer agents and chemotherapeutic agents.

In one embodiment, the anti-Siglec-10 neutralizing antibodies lack binding to human CD16 yet potentiate the activity of CD16-expressing effector cells (e.g. NK or effector T cells). Accordingly, in one embodiment, the second or additional second therapeutic agent is an antibody or other Fc domain-containing protein capable of inducing ADCC toward a cell to which it is bound, e.g. via CD16 expressed by an NK cell. Typically, such antibody or other protein will comprise a domain that binds to an antigen of interest, e.g. an antigen present on a tumor cell (tumor antigen), and an Fc domain or portion thereof, and will exhibit binding to the antigen via the antigen binding domain and to Fcγ receptors (e.g. CD16) via the Fc domain. In one embodiment, its ADCC activity will be mediated at least in part by CD16. In one embodiment, the additional therapeutic agent is an antibody having a native or modified human Fc domain, for example a Fc domain from a human IgG1 or IgG3 antibody. The term "antibody-dependent cell-mediated cytotoxicity" or "ADCC" is a term well understood in the art, and refers to a cell-mediated reaction in which non-specific cytotoxic cells that express Fc receptors (FcRs) recognize bound antibody on a target cell and subsequently cause lysis of the target cell. Non-specific cytotoxic cells that mediate ADCC include natural killer (NK) cells, macrophages, monocytes, neutrophils, and eosinophils. The term "ADCC-inducing antibody" refers to an antibody that demonstrates ADCC as measured by assay(s) known to those of skill in the art. Such activity is typically characterized by the binding of the Fc region with various FcRs. Without being limited by any particular mechanism, those of skill in the art will recognize that the ability of an antibody to demonstrate ADCC can be, for example, by virtue of it subclass (such as IgG1 or IgG3), by mutations introduced into the Fc region, or by virtue of modifications to the carbohydrate patterns in the Fc region of the antibody. Examples of antibodies that induce ADCC include rituximab (for the treatment of lymphomas, CLL, trastuzumab (for the treatment of breast cancer), alemtuzumab (for the treatment of chronic lymphocytic leukemia) and cetuximab (for the treatment of colorectal cancer, head and neck squamous cell carcinoma). Examples of ADCC-enhanced antibodies include but are not limited to: GA-101 (hypofucosylated anti-CD20), margetuximab (Fc enhanced anti-HER2), mepolizumab, MEDI-551 (Fc engineered anti-CD19), obinutuzumab (glycoengineered/hypofucosuylated anti-CD20), ocaratuzumab (Fc engineered anti-CD20), XmAb® 5574/MOR208 (Fc engineered anti-CD19).

In one embodiment, the anti-Siglec-10 neutralizing antibodies augments the efficacy of agents that neutralizes the inhibitory activity of human PD-1, e.g. that inhibits the interaction between PD-1 and PD-L1, notably in individuals who are poor responders to (or not sensitive to) treatment with agent that neutralizes the inhibitory activity of human PD-1. Accordingly, in one embodiment, the second or additional second therapeutic agent is an antibody or other agent that neutralizes the inhibitory activity of human PD-1.

Programmed Death 1 (PD-1) (also referred to as "Programmed Cell Death 1") is an inhibitory member of the CD28 family of receptors. The complete human PD-1 sequence can be found under GenBank Accession No. U64863. Inhibition or neutralization the inhibitory activity of PD-1 can involve use of a polypeptide agent (e.g., an antibody, a polypeptide fused to an Fc domain, an immunoadhesin, etc.) that prevents PD-L1-induced PD-1 signalling. There are currently at least six agents blocking the PD-1/PD-L1 pathway that are marketed or in clinical evaluation. One agent is BMS-936558 (Nivolumab/ONO-4538, Bristol-Myers Squibb; formerly MDX-1106). Nivolumab, (Trade name Opdivo®) is an FDA-approved fully human IgG4 anti-PD-L1 mAb that inhibits the binding of the PD-L1 ligand to both PD-1 and CD80 and is described as antibody 5C4 in WO 2006/121168, the disclosure of which is incorporated herein by reference. For melanoma patients, the most significant OR was observed at a dose of 3 mg/kg, while for other cancer types it was at 10 mg/kg. Nivolumab is generally dosed at 10 mg/kg every 3 weeks until cancer progression. The terms "reduces the inhibitory activity of human PD-1", "neutralizes PD-1" or "neutralizes the inhibitory activity of human PD-1" refers to a process in which PD-1 is inhibited in its signal transduction capacity resulting from the interaction of PD-1 with one or more of its binding partners, such as PD-L1 or PD-L2. An agent that neutralizes the inhibitory activity of PD-1 decreases, blocks, inhibits, abrogates or interferes with signal transduction resulting from the interaction of PD-1 with one or more of its binding partners, such as PD-L1, PD-L2. Such an agent can thereby reduce the negative co-stimulatory signal mediated by or through cell surface proteins expressed on T lymphocytes, so as to enhance T-cell effector functions such as proliferation, cytokine production and/or cytotoxicity.

MK-3475 (human IgG4 anti-PD1 mAb from Merck), also referred to as lambrolizumab or pembrolizumab (Trade name Keytruda®) has been approved by the FDA for the treatment of melanoma and is being tested in other cancers. Pembrolizumab was tested at 2 mg/kg or 10 mg/kg every 2 or 3 weeks until disease progression. DNA constructs encoding the variable regions of the heavy and light chains of the humanized antibodies h409. All have been deposited with the American Type Culture Collection Patent Depository (10801 University Blvd., Manassas, Va.). The plasmid containing the DNA encoding the heavy chain of h409A-I 1 was deposited on Jun. 9, 2008 and identified as 081469_SPD-H and the plasmid containing the DNA encoding the light chain of h409AI 1 was deposited on Jun. 9, 2008 and identified as 0801470SPD-L-I 1. MK-3475, also known as Merck 3745 or SCH-900475, is also described in WO2009/114335.

MPDL3280A/RG7446 (anti-PD-L1 from Roche/Genentech) is a human anti-PD-L1 mAb that contains an engineered Fc domain designed to optimize efficacy and safety by minimizing FcγR binding and consequential antibody-dependent cellular cytotoxicity (ADCC). Doses of ≤1, 10, 15, and 25 mg/kg MPDL3280A were administered every 3 weeks for up to 1 year. In phase 3 trial, MPDL3280A is administered at 1200 mg by intravenous infusion every three weeks in NSCLC.

AMP-224 (Amplimmune and GSK) is an immunoadhesin comprising a PD-L2 extra-cellular domain fused to an Fc domain. Other examples of agents that neutralize PD-1 may include an antibody that binds PD-L2 (an anti-PD-L2 antibody) and blocks the interaction between PD-1 and PD-L2.

Pidlizumab (CT-011; CureTech) (humanized IgG1 anti-PD1 mAb from CureTech/Teva), Pidlizumab (CT-011; CureTech) (see e.g., WO2009/101611) is another example; the agent was tested in thirty patients with rituximab-sensitive relapsed FL were treated with 3 mg/kg intravenous CT-011 every 4 weeks for 4 infusions in combination with rituximab dosed at 375 mg/m2 weekly for 4 weeks, starting 2 weeks after the first infusion of CT-011.

Further known PD-1 antibodies and other PD-1 inhibitors include AMP-224 (a B7-DC/IgG1 fusion protein licensed to GSK), AMP-514 described in WO 2012/145493, antibody MEDI-4736 (an anti-PD-L1 developed by AstraZeneca/Medimmune) described in WO2011/066389 and US2013/034559, antibody YW243.55.S70 (an anti-PD-L1) described in WO2010/077634, MDX-1105, also known as BMS-936559, is an anti-PD-L1 antibody developed by Bristol-Myers Squibb described in WO2007/005874, and antibodies and inhibitors described in WO2006/121168, WO2009/014708, WO2009/114335 and WO2013/019906, the disclosures of which are hereby incorporated by reference. Further examples of anti-PD1 antibodies are disclosed in WO2015/085847 (Shanghai Hengrui Pharmaceutical Co. Ltd.), for example antibodies having light chain variable domain CDR1, 2 and 3 of SEQ ID NO: 6, SEQ ID NO: 7 and/or SEQ ID NO: 8, respectively, and antibody heavy chain variable domain CDR1, 2 and 3 of SEQ ID NO: 3, SEQ ID NO: 4 or SEQ ID NO: 5, respectively, wherein the SEQ ID NO references are the numbering according to WO2015/085847, the disclosure of which is incorporated herein by reference. Antibodies that compete with any of these antibodies for binding to PD-1 or PD-L1 also can be used.

An exemplary anti-PD-1 antibody is pembrolizumab (see, e.g., WO 2009/114335 the disclosure of which is incorporated herein by reference.). The anti-PD-1 antibody may be the antibody h409AI 1 in WO 2008/156712, comprising heavy chain variable regions encoded by the DNA deposited at the ATCC as 081469_SPD-H and light chain variable regions encoded by the DNA deposited at the ATCC as0801470_SPD-L-I 1. In other embodiments, the antibody comprises the heavy and light chain CDRs or variable regions of pembrolizumab. Accordingly, in one embodiment, the antibody comprises the CDR1, CDR2, and CDR3 domains of the VH of pembrolizumab encoded by the DNA deposited at the ATCC as 081469_SPD-H, and the CDR1, CDR2 and CDR3 domains of the VL of pembrolizumab encoded by the DNA deposited at the ATCC as 0801470_SPD-L-I 1.

In some embodiments, the PD-1 neutralizing agent is an anti-PD-L1 mAb that inhibits the binding of PD-L1 to PD-1. In some embodiments, the PD-1 neutralizing agent is an anti-PD1 mAb that inhibits the binding of PD-1 to PD-L1. In some embodiments, the PD-1 neutralizing agent is an immunoadhesin (e.g., an immunoadhesin comprising an extracellular or PD-1 binding portion of PD-L1 or PD-L2 fused to a constant region (e.g., an Fc region of an immunoglobulin sequence).

In the treatment methods, the anti-Siglec10 antibody and the second therapeutic agent can be administered separately, together or sequentially, or in a cocktail. In some embodiments, the antigen-binding compound is administered prior to the administration of the second therapeutic agent. For example, the anti-Siglec10 antibody can be administered approximately 0 to 30 days prior to the administration of the second therapeutic agent. In some embodiments, a Siglec-binding compound is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days prior to the administration of the second therapeutic agent. In some embodiments, an anti-Siglec10 antibody is administered concurrently with the administration of the therapeutic agents. In some embodiments, an anti-Siglec10 antibody is administered after the administration of the second therapeutic agent. For example, an anti-Siglec10 antibody can be administered approximately 0 to 30 days after the administration of the second therapeutic agent. In some embodiments, an anti-Siglec10 antibody is administered from about 30 minutes to about 2 weeks, from about 30 minutes to about 1 week, from about 1 hour to about 2 hours, from about 2 hours to about 4 hours, from about 4 hours to about 6 hours, from about 6 hours to about 8 hours, from about 8 hours to 1 day, or from about 1 to 5 days after the administration of the second therapeutic agent.

In other aspects, methods are provided for identifying Siglec-10-expressing NK cells, B cells and/or T cells. Assessing the co-expression of Siglec-10 on NK cells, B cells and/or T cells can be used in diagnostic or prognostic methods. For example, a biological sample can be obtained from an individual (e.g. from a blood sample, from cancer or cancer-adjacent tissue obtained from a cancer patient) and analyzed for the presence of Siglec-10 on NK and/or T cells (e.g. tumor infiltrating cells). The expression of Siglec-10 on such cells can, for example, be used to identify individuals having NK and/or T cells, for example tumor infiltrating NK and/or T cells which are inhibited by Siglec-10 polypeptides. The method can, for example, be useful as a prognostic for response to treatment with an agent that neutralizes Siglec-10.

In certain optional aspects, patients can be identified for treatment with an anti-Siglec-10 antibody by assessing the presence in a tumor sample (e.g. tumor tissue and/or tumor adjacent tissue) of natural ligands for Siglec-10. In one embodiment of any of the therapeutic uses or cancer treatment or prevention methods herein, the treatment or prevention of a cancer in an individual comprises:

a) determining whether malignant cells (e.g. tumor cells) within the individual having a cancer bear a ligand of Siglec-10, and b) upon a determination that a ligand of Siglec-10 is present (e.g. on the surface of) malignant cells (e.g. tumor cells), administering to the individual an anti-Siglec-10 antibody, e.g. an antibody according to any aspect of the disclosure.

In one embodiment, a determination that a biological sample (e.g., a sample comprising tumor cells, tumor tissue and/or tumor adjacent tissue) prominently or significantly expresses a ligand of Siglec-10 indicates that the individual has a cancer that can be treated with and/or may receive benefit from an antibody that inhibits Siglec-10 polypeptide.

In one embodiment, significant expression of a ligand of Siglec-10 means that said ligand(s) are expressed in or present on a substantial number of tumor cells taken from a given individual. While not bound by a precise percentage value, in some examples a ligand can be said to be "significantly expressed" if be present on at least 30%, 40%, 50%, 60%, 70%, 80%, or more of the tumor cells taken from a patient (in a sample).

In one embodiment of any of the methods, determining whether malignant cells (e.g. tumor cells) within the individual having a cancer express a ligand of Siglec-10 comprises determining the level of expression of ligand(s) of Siglec-10 on malignant cells in a biological sample and comparing the level to a reference level (e.g. a value, weak or strong cell surface staining, etc.). The reference level may, for example, correspond to a healthy individual, to an individual deriving no/low clinical benefit from treatment with an anti-Siglec-10 antibody, or to an individual deriving substantial clinical benefit from treatment with an anti-Siglec-10 antibody. A determination that a biological sample expresses a ligand of Siglec-10 at a level that is increased (e.g. a high value, strong surface staining, a level that corresponds to that of an individual deriving substantial clinical benefit from treatment with an anti-Siglec-10 antibody, a level that is higher than that corresponding to an individual deriving no/low clinical benefit from treatment with an anti-Siglec-10 antibody, etc.) indicates that the individual has a cancer that can be treated with an anti-Siglec-10 antibody.

EXAMPLES

Example 1: Generation of Anti-Siglec-10 Antibodies

A. Immunization

To obtain anti-human Siglec-10 antibodies, Balb/c mice were immunized with human Siglec-10 Fc extracellular domain recombinant protein. Mice received one primo-immunization with an emulsion of 50 µg of Siglec-10 Fc protein and Complete Freund Adjuvant, intraperitoneally. Mice received a second and a third immunization with an emulsion of 50 µg of Siglec-10 Fc protein and Complete Freund Adjuvant, intraperitoneally. And finally, mice received a boost with 15 µg of Siglec-10 Fc protein, intravenously. Immune spleen cells were fused 3 days after the boost with X63.Ag8.653 immortalized B cells, and cultured in the presence of irradiated spleen cells. Hybridomas were plated in semi-solid methylcellulose-containing medium and growing clones were picked using a clonepix 2 apparatus (Molecular Devices).

Supernatants (SN) of growing clones were tested in a primary screen by flow cytometry using huSiglec-10-expressing CHO cell lines. The presence of reacting antibodies in supernatants was revealed by Goat anti-mouse polyclonal antibody (pAb) labeled with alexa fluor 647. 15 supernatants were found to bind to human Siglec-10. Antibodies that bind Siglec-10 were cloned and produced as recombinant chimeric human IgG1 antibodies with a heavy chain N297Q (Kabat EU numbering) mutation which results in lack of N-linked glycosylation and low or abolished binding to human Fcγ receptors CD16A, CD16B, CD32A, CD32B and CD64.

Amino acid sequences and Genbank references for Siglec-10 polypeptides used are shown below in Table 1.

TABLE 1

Siglec sequences

| Name | NCBI Reference Sequence | Sequence (AA) |
|---|---|---|
| Human Siglec-10 | NP_149121; NM_033130 | MDGRFWIRVQESVMVPEGLCISVPCSFSYPRQDWTGSTPAYGYWFKAVTETT-KGAPVATNHQSREVEMSTRGRFQLTGDPAKGNCSLVIRDAQ-MQDESQYFFRVERGSYVRYNFMNDGFFLKVTALTQKPDVYIPETLEPGQPVTVICVF NWAFEECPPPSFSWTGAALSSQGTKPTTSHFSVLSFTPRPQDHNTDLTCHV DFSRKGVSVQRTVRLRVAYAPRDLVISISRDNTPALEPQPQGNVPYLEAQKGQFLRLL-CAADSQPPATLSWVLQNRVLSSSHPWGPRPLGLELPGVKAGDSGRYTCRAENR LGSQQRALDLSVQYPPENLRVMVSQANRTVLENLGNGTSLPVLEGQSLCLVCVT HSSPPARLSWTQRGQVLSPSQPSDPGVLELPRVQVEHEGEFTCHARH PLGSQHVSLSLSVHYSPKLLGPSCSWEAEGLHCSCSSQASPAPSLRWWLGEELLE-GNSSQDSFEVTPSSAGPWANSSLSLHGGLSSGLRLRCEAWNVHGAQSG-SILQLPDKKGLISTAFSNGAFLGIGITALLFLCLALIIMKILPKRRTQTETPRPRFSRHSTIL-DYINVVPTAGPLAQKRNQKATPNSPRTPLPPGAPSPESKKNOKKQYQLPSF PEPKSSTQAPESQESQEELHYATLNFPGVRPRPEARMPKGTQADYAEVKFQ (SEQ ID NO: 1) |

Example 2: Binding to CD33-Related Siglecs

CD33-related Siglecs that share high sequence similarity to Siglec-10 are generally divided into two groups, a first subset made up of Siglec-1, -2, -4 and -15, and the CD33-related group of Siglecs which includes Siglec-3, -5, -6, -7, -8, -9, -11, -12, -14 and -16. Since other CD33-related Siglecs have different biological functions and/or may not be involved in tumor surveillance, antibodies are further screened to assess whether it is possible to obtain cross-reactive Siglec-10 antibodies that do not bind to other CD33-related Siglecs.

Cells expressing Siglec-3, -5, -6, -7, -8, -9, -11 and -12 were generated using the amino acid sequences and Genbank references for Siglec polypeptides shown below in Table 2. Anti-Siglec-10 antibodies are tested by flow cytometry for binding to the cells. Binding of antibodies on human Siglec-10 was tested by flow cytometry on CHO cells transfected with human Siglec-10, human Siglec-7 or human Siglec-11. Cells were incubated 1 h in Staining Buffer (SB) with primary antibodies at 8 ug/ml, then were washed three times with SB. Secondary Goat F(ab')2 Anti-Human IgG (Fc) PE (Beckman Coulter) was incubated for 30 min at 4° C., cells were washed twice with SB. Fluorescence was revealed with HTFC Intellicyt cytometer. The 6 antibodies bound human Siglec-10 CHO transfectants with high differential in binding affinity over the control Siglec-7 or Siglec-11 CHO transfectants (no or only low residual binding to Siglec-7 or Siglec-11). The highest MFI for Siglec-10 binding was observed with S10A (also referred to as CHS2-S10-A), followed by S10-B and S10-C (also referred to as CHS2-S10-B and CHS2-S10-C respectively) (see FIG. 1). The $EC_{50}$ as determined by flow cytometry for binding for S10-A antibody to Siglec-10 expressing CHO cells was 0.1 µg/ml.

TABLE 2

Siglec amino acid sequences

| Name | NCBI Reference Sequence | Sequence (AA) |
|---|---|---|
| Human Siglec-7 | NM_014385.3; NP_055200.1 | QKSNRKDYSLTMQSSVTVQEGMCVHVRCSFSYPVDSQTDSDPVHGYWFRAGNDIS WKAPVATNNPAWAVQEETRDRFHLLGDPQTKNCTLSIRDARMSDAGRYFFRMEKG NIKWNYKYDQLSVNVTALTHRPNILIPGTLESGCFQNLTCSVPWACEQGTPPMISWM GTSVSPLHPSTTRSSVLTLIPQPQHHGTSLTCQVTLPGAGVTTNRTIQLNVSYPPQNLT VTVFQGEGTASTALGNSSSLSVLEGQSLRLVCAVDSNPPARLSWTWRSLTLYPSQPSN PLVLELQVHLGDEGEFTCRAQNSLGSQHVSLNLSLQQEYTGKMRPVSGVLLGAVGGA GATALVFLSFCVIFIVVRSCRKKSARPAADVGDIGMKDANTIRGSASQGNLTESWADD NPRHHGLAAHSSGEEREIQYAPLSFHKGEPQDLSGQEATNNEYSEIKIPK (SEQ ID NO: 3) |
| Human Siglec-9 | NM_014441.2; NP_055256.1 | QTSKLLTMQSSVTVQEGLCVHVPCSFSYPSHGWIYPGPVVHGYWFREGANTDQAP VATNNPARAVWEETRDRFHLLGDPHTKNCTLSIRDARRSDAGRYFFRMEKGSIKWNY KHHRLSVNVTALTHRPNILIPGTLESGCPQNLTCSVPWACEQGTPPMISWIGTSVSPL DPSTTRSSVLTLIPQPQDHGTSLTCQVTFPGASVTTNKTVHLNVSYPPQNLTMTVFQG DGTVSTVLGNGSSLSLPEGQSLRLVCAVDAVDSNPPARLSLSWRGLTLCPSQPSNPGV LELPWVHLRDAAEFTCRAQNPLGSQQVYLNVSLQSKATSGVTQGVVGGAGATALVF LSFCVIFVVVRSCRKKSARPAAGVGDTGIEDANAVRGSASQGPLTEPWAEDSPPDQP PPASARSSVGEGELQYASLSFQMVKPWDSRGQEATDTEYSEIKIHR (SEQ ID NO: 4) |
| Human Siglec-3 | NM_001772.3; NP_001763.3 | DPNFWLQVQESVTVQEGLCVLVPCTFFHPIPYYDKNSPVHGYWFREGAIISGDSPVAT NKLDQEVQEETQGRFRLLGDPSRNNCSLSIVDARRRDNGSYFFRMERGSTKYSYKSPQ LSVHVTDLTHRPKILIPGTLEPGHSKNLTCSVSWACEQGTPPIFSWL |

TABLE 2-continued

Siglec amino acid sequences

| Name | NCBI Reference Sequence | Sequence (AA) |
|---|---|---|
| | | SAAPTSLGPRTTHSSVLIITPRPQDHGTNLTCQVKFAGAGVTTERTIQLNVTYV<br>PQNPTTGIFPGDGSGKQETRAGVVHGAIGGAGVTALLALCLCLIFFIVKTHRRKAARTA<br>VGRNDTHPTTGSASPKHQKKSKLHGPTETSSCSGAAPTVEMDEELHYASLNF<br>HGMNPSKDTSTEYSEVRTQ<br>(SEQ ID NO: 5) |
| Human Siglec-5 | NM_003830.3 | EKPVYELQVQKSVTVQEGLCVLVPCSFSYPWRSWYSSPPLYVYWFRDGEIPYYAEVVA<br>TNNPDRRVKPETQGRFRLLGDVQKKNCSLSIGDARMEDTGSYFFRVERGRDVKYSYQ<br>QNKLNLEVTALIEKPDIHFLEPLESGRPTRLSCSLPGSCEAGPPLTFSWTGNALSPLDPE<br>TTRSSELTLTPRPEDHGTNLTCQMKRQGAQVTTERTVQLNVSYA<br>PQTITIFRNGIALEILQNTSYLPVLEGQALRLLCDAPSNPPAHLSWFQGSPALNATPISN<br>TGILELRRVRSAEEGGFTCRAQHPLGFLQIFLNLSVYSLPQLLGPSCSWEAEGLHCRCSF<br>RARPAPSLCWRLEEKPLEGNSSQGSFKVNSSSAGPWANSSLILHGGLSSDLKVSCKAW<br>NIYGSQSGSVLLLQGRSNLGTGVVPAALGGAGVMALLCICLCLIFFLIVKARRKQAAGR<br>PEKMDDEDPIMGTITSGSRKKPWPDSPGDQASPPGDAPPLEEQKELHYASLSFSEMK<br>SREPKDQEAPSTTEYSEIKTSK<br>(SEQ ID NO: 6) |
| Human Siglec-6 | NM_198845.4 | QERRFQLEGPESLTVQEGLCVLVPCRLPTTLPASYYGYGYWFLEGADVPVATNDPDEE<br>VQEETRGRFHLLWDPRRKNCSLSIRDARRRDNAAYFFRLKSKWMKYGYTSSKLSVRV<br>MALTHRPNISIPGTLESGHPSNLTCSVPWVCEQGTPPIFSWMSAAPTSLGPRTTQSSV<br>LTITPRPQDHSTNLTCQVTFPGAGVTMERTIQLNVSSFKILQNTSSLPVLEGQALRLLC<br>DADGNPPAHLSWFQGFPALNATPISNTGVLELPQVGSAEEGDFTCRAQHPLGSLQISL<br>SLFVHWKPEGRAGGVLGAVWGASITTLVFLCVCFIFRVKTRRKKAAQPVQNTDDVNP<br>VMVSGSRGHQHQFQTGIVSDHPAEAGPISEDEQELHYAVLHFHKVQPQEPKVTDTE<br>YSEIKIHK<br>(SEQ ID NO: 7) |
| Human Siglec-8 | NM_014442.2 | MEGDRQYGDGYLLQVQELVTVQEGLCVHVPCSFSYPQDGWTDSDPVHGYWFRAG<br>DRPYQDAPVATNNPDREVQAETQGRFQLLGDIWSNDCSLSIRDARKRDKGSYFFRLE<br>RGSMKWSYKSQLNYKTKQLSVFVTALTHRPDILILGTLESGHSRNLTCSVPWACKQGT<br>PPMISWIGASVSSPGPTTARSSVLTLTPKPQDHGTSLTCQVTLPGTGVTTTSTVRLDVS<br>YPPWNLTMTVFQGDATASTALGNGSSLSVLEGQSLRLVCAVNSNPPARLSWTRGSLT<br>LCPSRSSNPGLLELPRVHVRDEGEFTCRAQNAQGSQHISLSLSLQNEGTGTSRPVSQV<br>TLAAVGGAGATALAFLSFCIIFIIVRSCRKKSARPAAGVGDTGMEDAKAIRGSASQGPL<br>TESWKDGNPLKKPPPAVAPSSGEEGELHYATLSFHKVKPQDPQGQEATDSEYSEIKIH<br>KRETAETQACLRNHNPSSKEVRG<br>(SEQ ID NO: 8) |
| Human Siglec-11 | NM_052884.2 | NKDPSYSLQVQRQVPVPEGLCVIVSCNLSYPRDGWDESTAAYGYWFKGRTSPKTGAP<br>VATNNQSREVEMSTRDRFQLTGDPGKGSCSLVIRDAQREDEAWYFFRVERGSRVRH<br>SFLSNAFFLKVTALTKKPDVYIPETLEPGQPVTVICVFNWAFKKCPAPSFSWTGAALSP<br>RRTRPSTSHFSVLSFTPSPQDHDTDLTCHVDFSRKGVSAQRTVRLRVAYAPKDLIISISH<br>DNTSALELQGNVIYLEVQKGQFLRLLCAADSQPPATLSWVLQDRVLSSSHPWGPRTL<br>GLELRGVRAGDSGRYTCRAENRLGSQQQALDLSVQYPPENLRVMVSQANRTVLENL<br>GNGTSLPVLEGQSLRLVCVTHSSPPARLSWTRWGQTVGPSQPSDPGVLELPPIQMEH<br>EGEFTCHAQHPLGSQHVSLSLSVHYPPQLLGPSCSWEAEGLHCSCSSQASPAPSLRW<br>WLGEELLEGNSSQGSFEVTPSSAGPWANSSLSLHGGLSSGLRLRCKAWNVHGAQSG<br>SVFQLLPGKLEHGGGLGLGAALGAGVAALLAFCSCLVVFRVKICRKEARKRAAAEQDV<br>PSTLGPISQGHQHECSAGSSQDHPPPGAATYTPGKGEEQELHYASLSFQGLRLWEPA<br>DQEAPSTTEYSEIKIHTGQPLRGPGFGLQLEREMSGMVPK<br>(SEQ ID NO: 9) |
| Human Siglec-12 | NM_053003.3 | KEQKDYLLTMQKSVTVQEGLCVSVLCSFSYPQNGWTASDPVHGYWFRAGDHVSRNI<br>PVATNNPARAVQEETRDRFHLLGDPQNKDCTLSIRDTRESDAGTYVFCVERGNMKW<br>NYKYDQLSVNVTASQDLLSRYRLEVPESVTVQEGLCVSVPCSVLYPHYNWTASSPVYG<br>SWFKEGADIPWDIPVATNTPSGKVQEDTHGRFLLLGDPQLTNNCSLSIRDARKGDSGK<br>YYFQVERGSRKWNYIYDKLSVHVTALTHMPTFSIPGTLESGHPRNLTCSVPWACEQG<br>TPPTITWMGASVSSSLDPTIITRSSMLSLIPQPQDHGTSLTCQVTLPGAGVTMTRAVRLN<br>ISYPPQNLTMTVFQGDGTASTTLRNGSALSVLEGQSLHLVCAVDSNPPARLSWTWGS<br>LTLSPSQSSNLGVLELPRVHVKDEGEFTCRAQNPLGSQHISLSLSLQNEYTGKMRPISG<br>VTLGAFGGAGATALVFLYFCIIFVVVRSCRKKSARPAVGVGDTGMEDANAVRGSASQ<br>GPLIESPADDSPPHHAPPALATPSPEEGEIQYASLSFHKARPQYPQEQEAIGYEYSEINIP<br>K<br>(SEQ ID NO: 10) |
| Human Siglec-16 | A6NMB1 | MLLLPLLLPVLGAGSLNKDPSYSLQVQRQVPVPEGLCVIVSCNLSYPRDG<br>WDESTAAYGYWFKGRTSPKTGAPVATNNQSREVAMSTRDRFQLTGDPGKG<br>SCSLVIRDAQREDEAWYFFRVERGSRVRHSFLSNAFFLKVTALTKKPDVYIPETLE-<br>PGQPVTVICVFNWAFKKCPAPSFSWTGAALSPRRTRPSTSHFSVLSFTPSPQDH<br>DTDLTCHVDF SRKGVSAQRT VRLRVASLELQGNVIYLEVQ KGQFLRLLCA ADSQP-<br>PATLS WVLQDRVLSS SHPWGPRTLG LELPGVKAGDSGRYTCRAEN RLGSQQRALD<br>LSVQYPPENLRVMVSQANRTVLENLRNGTSLRVLEGQSLRLVCVTHSSPP<br>ARLSWTWGEQ TVGPSQPSDP GVLQLPRVQM EHEGEFTCHA RHPLGSQRVS |

| Name | NCBI Reference Sequence | Sequence (AA) |
|---|---|---|
| | | LSFSVHCKSG PMTGVVLVAV GEVAMKILLL CLCLILLRVR SCRRKAARAA LGME-AADAVTD (SEQ ID NO: 11) |

Example 3: Siglec-10 Ligands on Human Tumor Cell Lines

In order to study the ability of anti-Siglec-10 antibodies to potentiate NK and/or T cell activity towards sialic ligand-bearing tumor cells, tumor cells were evaluated for Siglec-10 ligands at their surface. Tumor cells and cell lines can bear sialic acid ligand of Siglecs at their surface. In particular, the HT29 tumor cell line has been reported to bear sialic acid ligands of Siglec-9 (Laubli et al., (2014) J. Biol. Chem.; 289(48): 33481-33491).

HT29 cells were incubated with soluble Siglec-Fc polypeptides (Siglec-7-Fc, Siglec9-Fc and Siglec-10-Fc) and binding was assessed by flow cytometry. Results are shown in FIG. 2A. While soluble Siglec-9 and Siglec-7 bound to HT29 cells, Siglec-10 Fc proteins showed no or only minimal level of binding. Siglec-10 ligands are thus not present on these cells or are present at low levels, and their presence does not correlate with presence of Siglec-7 and/or Siglec-9 ligands.

We then sought to identify a cancer cell line bearing high levels of Siglec-10 ligands so as to provide a setting to identify an anti-Siglec-10 antibody that can block the sialic acid interaction in a setting of high expression, we screened panels of cancer cell lines to assess whether cell lines can be identified that bear Siglec-10 at their surface, and if so, whether a high-Siglec-10 line can be found. Briefly, sialic acid expressing cell lines were selected and binding of Siglec-10 Fc (as well as Siglec-7 Fc and Siglec-9 Fc) was tested by flow cytometry. Cells were incubated 1 hour in Staining Buffer (SB) with Siglec-10 Fc at 10 ug/ml, then were washed two times with SB. Secondary Goat Anti-Mouse IgG, Fcγ Fragment Specific (Jackson ImmunoResearch) was incubated for 30 min at 4° C., and then cells were washed twice with SB. Fluorescence was revealed with CANTO-II cytometer.

Of the cells tested, a wide variation of Siglec-10 binding was observed, indicating wide range of expression of Siglec-10 sialic acid ligand on tumor cells. Various tumor cell lines, illustrated by KG1, HL60 and COLO704 (FIG. 2B) showed no or low sialic acid ligand for Siglec-10. In other cases, similarly to the HT29 cell line, the CR1 tumor cell line expressed Siglec-7 and Siglec-9 ligand, however was negative for Siglec-10 ligands (FIG. 2A). On the other hand, as shown in FIG. 3, HCT 116 and WiDr tumor cells lines bear significant levels of Siglec-10 ligands, and two tumor cell lines, MDA-MB-231 (breast cancer) and A375 (melanoma) cell lines, had the highest expression of Siglec-10 ligands (about 5-fold difference compared to cells such as HL60 and COLO704). These two cell lines demonstrating the highest Siglec-10 ligand expression level were selected for antibody blocking assays (FIG. 3).

Example 4: Anti-Siglec-10 Monoclonal Antibodies can Block Siglec-10 Interaction with Human Tumor Cells The blocking activity of the anti-Siglec-10 antibodies was evaluated by flow cytometry. Siglec-10 Fc (Mouse IgFc) at 10 µg/ml was incubated 1 h in Staining Buffer (SB) with primary antibodies at 120 µg/ml and a series of dilution of 1:4. The Siglec-10Fc/antibody complexes were incubated with cell lines 1 h at 4° C. then were washed two times with SB. Secondary Goat Anti-Mouse IgG, Fcγ Fragment Specific (Jackson ImmunoResearch) was incubated 30 min at 4° C., and then cells were washed twice with SB. Fluorescence was revealed with CANTO-II cytometer.

Antibody S10-A was selected based on highest potency for blocking Siglec-10 (FIG. 4). Two further antibodies (S10-B and S10-C) retained blocking activity albeit weaker than S10-A. Other antibodies that bound to Siglec-10, however, were non-blocking (illustrated by antibody S10-D, see FIG. 4). S10A was also tested for inhibition of the Siglec-10 interaction with the HCT 116 cells (see FIG. 4).

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context herein are to be construed to cover both the singular and the plural, unless otherwise indicated herein or clearly contradicted by context.

Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The description herein of any aspect or embodiment herein using terms such as "comprising", "having," "including," or "containing" with reference to an element or elements is intended to provide support for a similar aspect or embodiment that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A method for the treatment of a colon or breast cancer in a human patient, the method comprising administering to said human patient having a colon cancer or a breast cancer expressing human Siglec-10 an effective amount of an antibody or antibody fragment that specifically binds to human Siglec-10, wherein the antibody or antibody fragment comprises:

a) a heavy chain comprising SEQ ID NO: 14 (HCDR1), SEQ ID NO: 15 (HCDR2) and SEQ ID NO: 16

(HCDR3) and a light chain comprising SEQ ID NO: 17 (LCDR1), SEQ ID NO: 18 (LCDR2) and SEQ ID NO: 19 (LCDR3);

b) a heavy chain comprising SEQ ID NO: 22 (HCDR1), SEQ ID NO: 23 (HCDR2) and SEQ ID NO: 24 (HCDR3) and a light chain comprising SEQ ID NO: 25 (LCDR1), SEQ ID NO: 26 (LCDR2) and SEQ ID NO: 27 (LCDR3); or c) a heavy chain comprising SEQ ID NO: 30 (HCDR1), SEQ ID NO: 31 and (HCDR2) SEQ ID NO: 32 (HCDR3) and a light chain comprising SEQ ID NO: 33 (LCDR1), SEQ ID NO: 34 (LCDR2) and SEQ ID NO: 35 (LCDR3).

2. The method of claim 1, wherein the cancer is a breast cancer.

3. The method of claim 1, wherein the cancer is colon cancer.

4. The method of claim 1, wherein the human patient is treated with an effective amount of an antibody or antibody fragment that comprises a heavy chain comprising SEQ ID NO: 14 (HCDR1), SEQ ID NO: 15 (HCDR2) and SEQ ID NO: 16 (HCDR3) and a light chain comprising SEQ ID NO: 17 (LCDR1), SEQ ID NO: 18 (LCDR2) and SEQ ID NO: 19 (LCDR3).

5. The method of claim 1, wherein the human patient is treated with an effective amount of an antibody or antibody fragment that comprises a heavy chain comprising SEQ ID NO: 22 (HCDR1), SEQ ID NO: 23 (HCDR2) and SEQ ID NO: 24 (HCDR3) and a light chain comprising SEQ ID NO: 25 (LCDR1), SEQ ID NO: 26 (LCDR2) and SEQ ID NO: 27 (LCDR3).

6. The method of claim 1, wherein the human patient is treated with an effective amount of an antibody or antibody fragment that comprises a heavy chain comprising SEQ ID NO: 30 (HCDR1), SEQ ID NO: 31 (HCDR2) and SEQ ID NO: 32 (HCDR3) and a light chain comprising SEQ ID NO: 33 (LCDR1), SEQ ID NO: 34 (LCDR2) and SEQ ID NO: 35 (LCDR3).

7. The method of claim 1, wherein the human patient is treated with an effective amount of an antibody or antibody fragment comprising a heavy chain comprising SEQ ID NO: 12 and a light chain comprising SEQ ID NO: 13.

8. The method of claim 1, wherein the human patient is treated with an effective amount of an antibody or antibody fragment comprising a heavy chain comprising SEQ ID NO: 20 and a light chain comprising SEQ ID NO: 21.

9. The method of claim 1, wherein the human patient is treated with an effective amount of an antibody or antibody fragment comprising a heavy chain comprising SEQ ID NO: 28 and a light chain comprising SEQ ID NO: 29.

* * * * *

UNITED STATES PATENT AND TRADEMARK OFFICE
CERTIFICATE OF CORRECTION

PATENT NO. : 11,083,785 B2
APPLICATION NO. : 15/776452
DATED : August 10, 2021
INVENTOR(S) : Stephanie Cornen et al.

Page 1 of 1

It is certified that error appears in the above-identified patent and that said Letters Patent is hereby corrected as shown below:

In the Specification

Column 29,
Line 23, "510-C;" should read --S10-C;--.

Signed and Sealed this
Thirtieth Day of November, 2021

Drew Hirshfeld
*Performing the Functions and Duties of the*
*Under Secretary of Commerce for Intellectual Property and*
*Director of the United States Patent and Trademark Office*